(12) United States Patent
Mukai et al.

(10) Patent No.: US 9,431,960 B2
(45) Date of Patent: Aug. 30, 2016

(54) SOLUTION TESTING EQUIPMENT

(71) Applicants: ROHM CO., LTD., Kyoto (JP); Kyoto University, Kyoto (JP)

(72) Inventors: Toshikazu Mukai, Kyoto (JP); Yuichi Ogawa, Kyoto (JP)

(73) Assignees: ROHM CO., LTD., Kyoto (JP); KYOTO UNIVERSITY, Kyoto (JP)

( * ) Notice: Subject to any disclaimer, the term of this patent is extended or adjusted under 35 U.S.C. 154(b) by 120 days.

(21) Appl. No.: 14/084,658

(22) Filed: Nov. 20, 2013

(65) Prior Publication Data
US 2014/0139238 A1  May 22, 2014

(30) Foreign Application Priority Data
Nov. 21, 2012  (JP) ................ 2012-254978

(51) Int. Cl.
G01R 27/04 (2006.01)
H03B 7/14 (2006.01)
G01N 22/00 (2006.01)

(52) U.S. Cl.
CPC ............. *H03B 7/14* (2013.01); *G01N 22/00* (2013.01)

(58) Field of Classification Search
CPC ............ H03B 7/00–7/146; H03B 9/00–9/148
USPC ................. 331/116 R–107 T; 324/630–648; 250/338.1–339.14, 504 R
See application file for complete search history.

(56) References Cited

U.S. PATENT DOCUMENTS

| 8,274,052 | B1* | 9/2012 | Fukuzawa et al. | ........ 250/341.1 |
| 2006/0186897 | A1* | 8/2006 | Niemann | ....... 324/633 |
| 2006/0279738 | A1* | 12/2006 | Ogawa et al. | ................ 356/445 |
| 2008/0088847 | A1* | 4/2008 | Muraishi et al. | ............. 356/446 |
| 2008/0137068 | A1* | 6/2008 | Ouchi et al. | ..................... 356/51 |
| 2010/0026401 | A1* | 2/2010 | Mukai et al. | ............. 331/107 T |
| 2010/0045995 | A1* | 2/2010 | Malic et al. | .................. 356/445 |
| 2010/0166359 | A1* | 7/2010 | Fujimaki et al. | ............... 385/12 |
| 2010/0225897 | A1* | 9/2010 | Fermann et al. | ............... 356/51 |
| 2011/0253897 | A1* | 10/2011 | Saeedkia et al. | .......... 250/358.1 |

FOREIGN PATENT DOCUMENTS

| JP | H06-018421 A | 1/1994 |
| JP | H06-066721 A | 3/1994 |
| JP | 2005-017644 A | 1/2005 |
| JP | 2007-078621 A | 3/2007 |
| JP | 2007-124250 A | 5/2007 |
| JP | 2010-057161 A | 3/2010 |
| JP | 2012-078304 A | 4/2012 |
| JP | 2012-215530 A | 11/2012 |

OTHER PUBLICATIONS

Naoyuki Orihashi et al., "Millimeter and Submillimeter Oscillators Using Resonant Tunneling Diodes with Stacked-Layer Slot Antennas" Japanese Journal of Applied Physics. vol. 43, No. 10A, 1309-1311, 2004.
Japanese Office Action with translation dated May 31, 2016.

* cited by examiner

Primary Examiner — Patrick Assouad
Assistant Examiner — Demetrius Pretlow
(74) Attorney, Agent, or Firm — Rabin & Berdo, P.C.

(57) ABSTRACT

There is provided solution testing equipment which can detect an output variation of a THz oscillation device using a THz wave (hv) by contacting a liquid or cells on an RTD oscillation device, and can reduce the size and weight thereof. The solution testing equipment includes: a THz oscillation device configured to radiate the THz wave $I_s$; a THz detection device configured to receive the THz wave $I_s$; and a solution as a test object disposed on the THz oscillation device, in which the solution is tested on the basis of output characteristics of the terahertz wave varying in response to a relative permittivity of the solution.

27 Claims, 39 Drawing Sheets

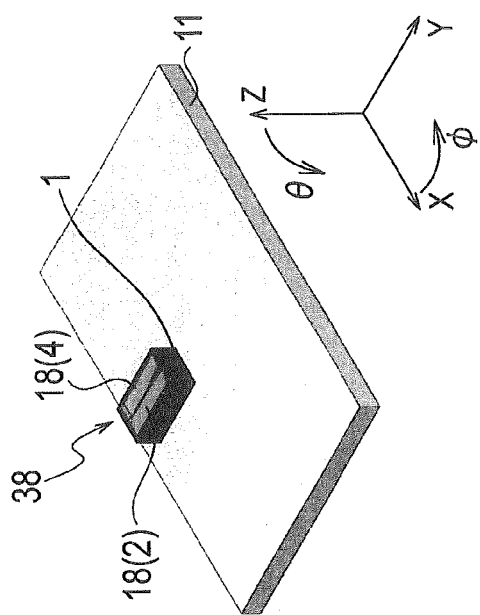
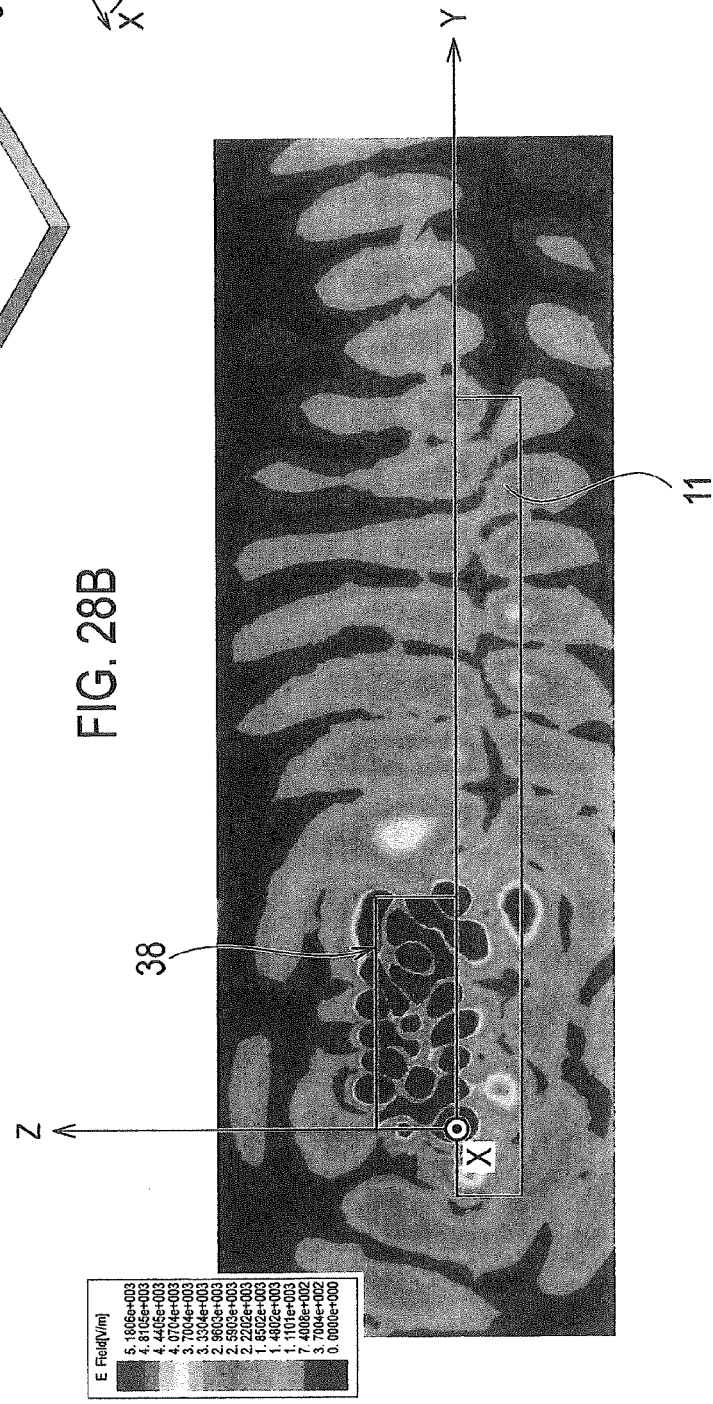

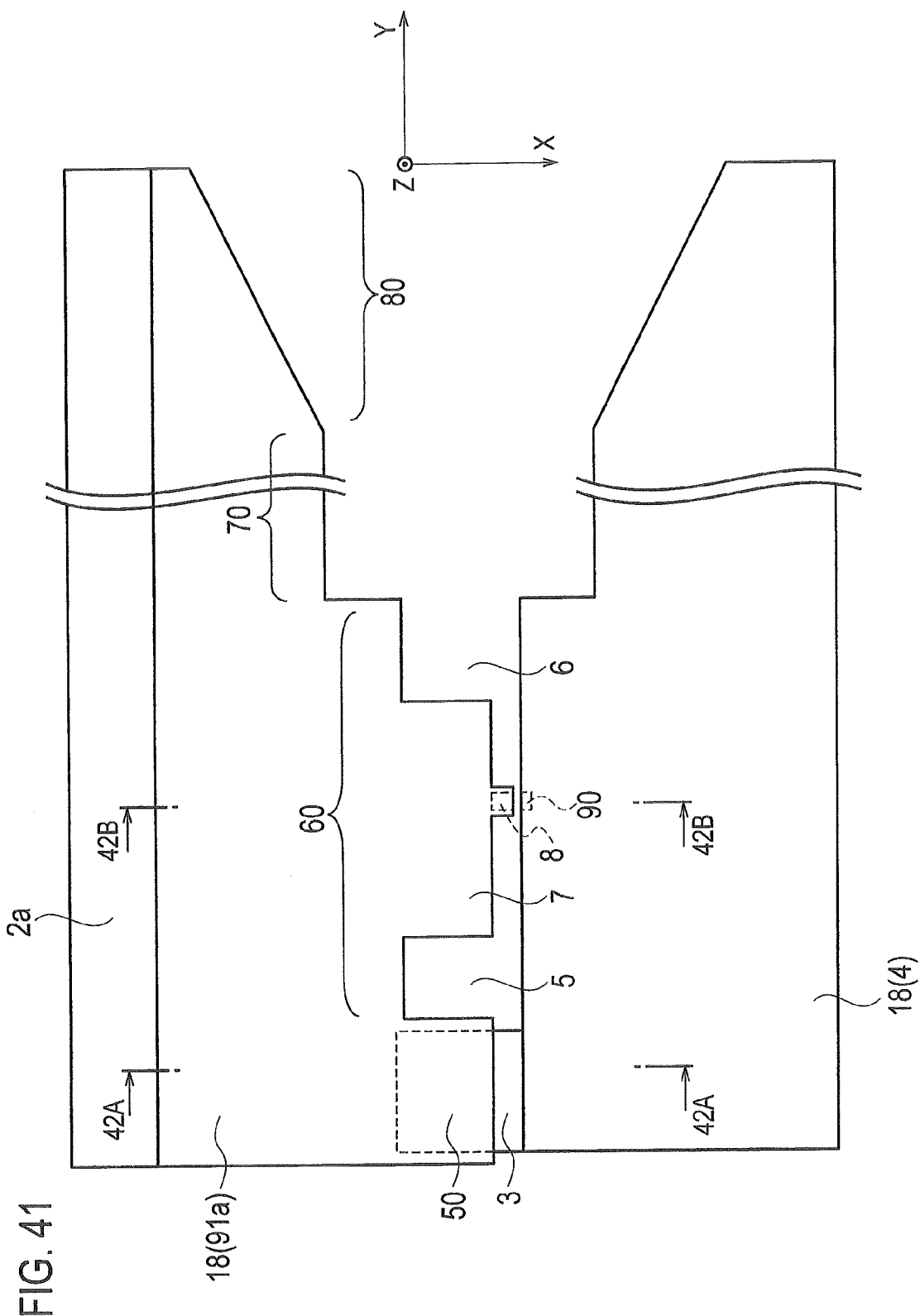

SOLUTION TESTING EQUIPMENT

CROSS REFERENCE TO RELATED APPLICATIONS AND INCORPORATION BY REFERENCE

This application is based upon and claims the benefit of priority from prior Japanese Patent Application No. P2012-254978 filed on Nov. 21, 2012, the entire contents of which are incorporated herein by reference.

TECHNICAL FIELD

In particular, the present invention relates to related solution testing equipment which can detect an output variation of a terahertz (THz) oscillation device using a THz wave (hv) by contacting a liquid or cells on a resonant tunneling diode (RTD) oscillation device.

BACKGROUND ART

In recent years, since miniaturization of electron devices, such as a transistor, progresses, and the size thereof has nano size, a new phenomenon called a quantum effect has been observed. Then, the development which aimed at achieving of ultra high-speed devices or new functional devices is advanced using such a quantum effect.

On the other hand, trials to perform large capacity communication, information processing, or imaging or measurement, etc. has been performed in such environment using the frequency region which is in particular called a THz band and of which frequency is from 0.1 THz ($10^{11}$ Hz) to 10 THz. Such a frequency region is undeveloped frequency region between light and electromagnetic waves, and if a device which operates with this frequency band is achieved, there is expected many uses, such as measurement in various fields, e.g., physical characteristics, astronomy, living things, etc. in addition to the imaging, the large capacity communication, and the information processing mentioned above.

As a device for oscillating a high frequency electromagnetic wave at a frequency of the THz band, there is known a device having a structure for integrating a minute slot antenna on active devices, such as a transistor or a diode (for example, refer to Non Patent Literature 1).

On the other hand, there is also disclosed a THz oscillation device which can eliminate a leak from a slot transmission line over the whole oscillation frequency region and can oscillate a high-efficiency and high-output electromagnetic waves, even if it is the electromagnetic waves at a frequency band with the comparatively wide bandwidth oscillated from frequency variable oscillation devices (for example, refer to Patent Literature 1).

By the way, in conventionally, surface plasmon sensors using surface plasmon resonance (SPR) is known as a sensor for testing liquids, cells, etc.

The surface plasmon sensor is a sensor for measuring a dielectric constant of materials, e.g. liquids or cells on a metallic thin film, using the SPR, and is widely used for measurement of solution concentrations, and detection of protein or polymers, etc.

CITATION LIST

Patent Literature 1: Japanese Publication of Unexamined Patent Application 2007-124250

Non-Patent Literature 1: N. Orihashi, S. Hattori, and M. Asada: "Millimeter and Submillimeter Oscillators Using Resonant Tunneling Diodes with Stacked-Layer Slot Antennas," Jpn.J.Appl.Phys. vol. 43, L1309 (2004).

SUMMARY OF THE INVENTION

Technical Problem

However, since a penetrative region of electric fields is narrow in such surface plasmon sensors, there was a difficult point that only information on the surfaces, e.g. cells, as samples, is obtained.

Accordingly, there has been developed testing equipment using THz waves (hv) with a long wavelength and comparatively large penetrative region of electric fields for testing liquids or cells.

However, there was a problem that, since conventional testing equipment using the THz wave (hv) was needed to use femtosecond lasers etc. as a luminous source, such conventional testing equipment is a large-sized and expensive equipment, and is difficult to be applied on common testing.

The purpose of the present invention is to provide solution testing equipment which can detect an output variation of a THz oscillation device using a THz wave (hv) by contacting a liquid or cells on an RTD oscillation device, and can reduce the size and weight thereof.

Solution to Problem

According to an aspect of the invention, there is provided a solution testing equipment comprising: a terahertz (THz) oscillation device configured to radiate a THz wave; a THz detection device configured to receive the terahertz wave; and a solution as a test object disposed on the THz oscillation device, wherein the solution is tested on the basis of output characteristics of the terahertz wave varying in response to a relative permittivity of the solution.

Advantageous Effects of Invention

According to the present invention, there can be provided solution testing equipment which can detect the output variation of the THz oscillation device using the THz wave (hv) by contacting the liquid or cell on the RTD oscillation device, and can reduce the size and weight thereof.

BRIEF DESCRIPTION OF DRAWINGS

FIG. 28A is a schematic bird's-eye view structure diagram showing the THz oscillation device applied to the solution testing equipment according to the first embodiment in the case of forming a 0.6-µm-thick overlay insulating film ($SiO_2$ film) on the surface thereof.

FIG. 28B shows a simulation result of the field emission pattern on the Y-Z plane in the case of radiating the THz wave (hv) from the THz oscillation device shown in FIG. 28A.

FIG. 41 is a schematic top view diagram of a radiation pattern structure of a first electrode 4, a second electrode 2a, and a semiconductor layer 91a corresponding to FIG. 40.

DESCRIPTION OF EMBODIMENTS

Figure 1:
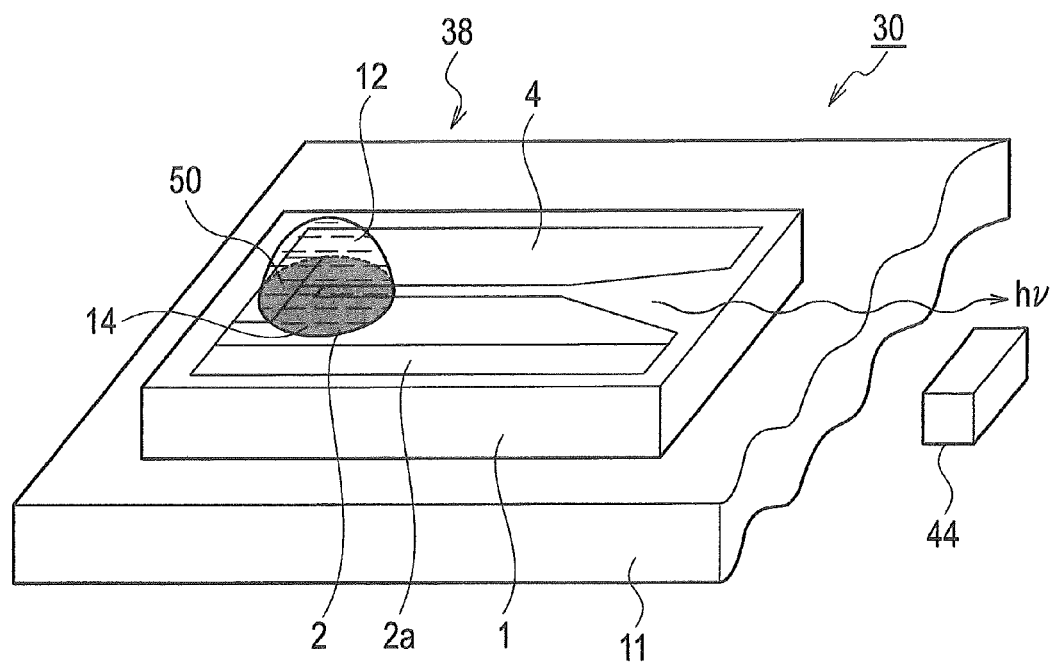
FIG. 1 is a schematic bird's-eye view structure diagram of solution testing equipment according to a first embodiment.

There will be described embodiments of the present invention, with reference to the drawings, where same blocks or elements are designated by same reference characters to eliminate redundancy and for simplicity. Drawings are schematic, not actual, and may be inconsistent in between in scale, ratio, etc.

The embodiments to be described hereinafter exemplify the apparatus and method as a technical concept or spirit of the present invention, and do not specify dispositions, etc. of each component part as examples mentioned below. The embodiments of the present invention may be changed without departing from the spirit or scope of claims.

[First Embodiment]

Figure 2:
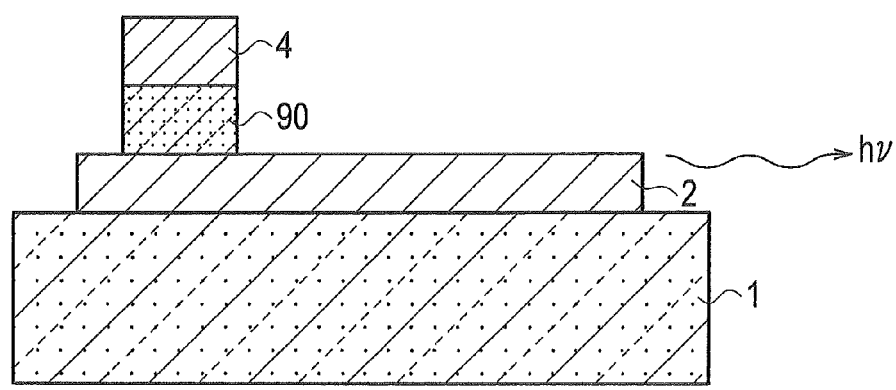
FIG. 2 is a schematic cross-sectional structure diagram of a THz oscillation device applicable to the solution testing equipment according to the first embodiment.

FIG. 1 illustrates a schematic bird's-eye view structure of solution testing equipment 30 according to a first embodiment. FIG. 2 illustrates a schematic cross-sectional structure of a THz oscillation device 38 applicable to the solution testing equipment 30 according to the first embodiment.

Figure 3:
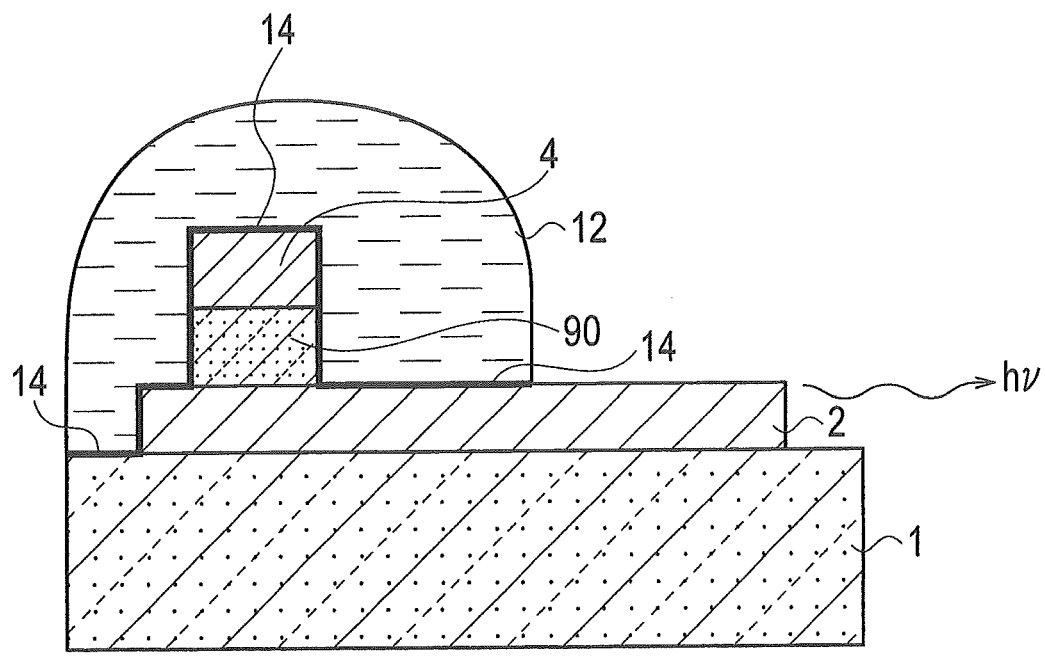
FIG. 3 is a schematic cross-sectional structure diagram in a state where a solution is contacted on the THz oscillation device applicable to the solution testing equipment according to the first embodiment.

FIG. 3 illustrates a schematic cross-sectional structure in a state where a solution is contacted on the THz oscillation device 38 applicable to the solution testing equipment 30 according to the first embodiment.

As shown in FIGS. 1-3, the solution testing equipment according to the first embodiment includes: the THz oscillation device 38 configured to radiate a THz wave (hv); a THz detection device 44 configured to receive the THz wave (hv); and a solution 12 as a test object disposed on the THz oscillation device 38. In the present embodiment, the solution 12 can be tested on the basis of output characteristics of the THz wave (hv) varying in response to a relative permittivity ∈ of the solution 12. Moreover, the output characteristics of the THz wave (hv) are radiation patterns of the THz wave.

Figure 16:
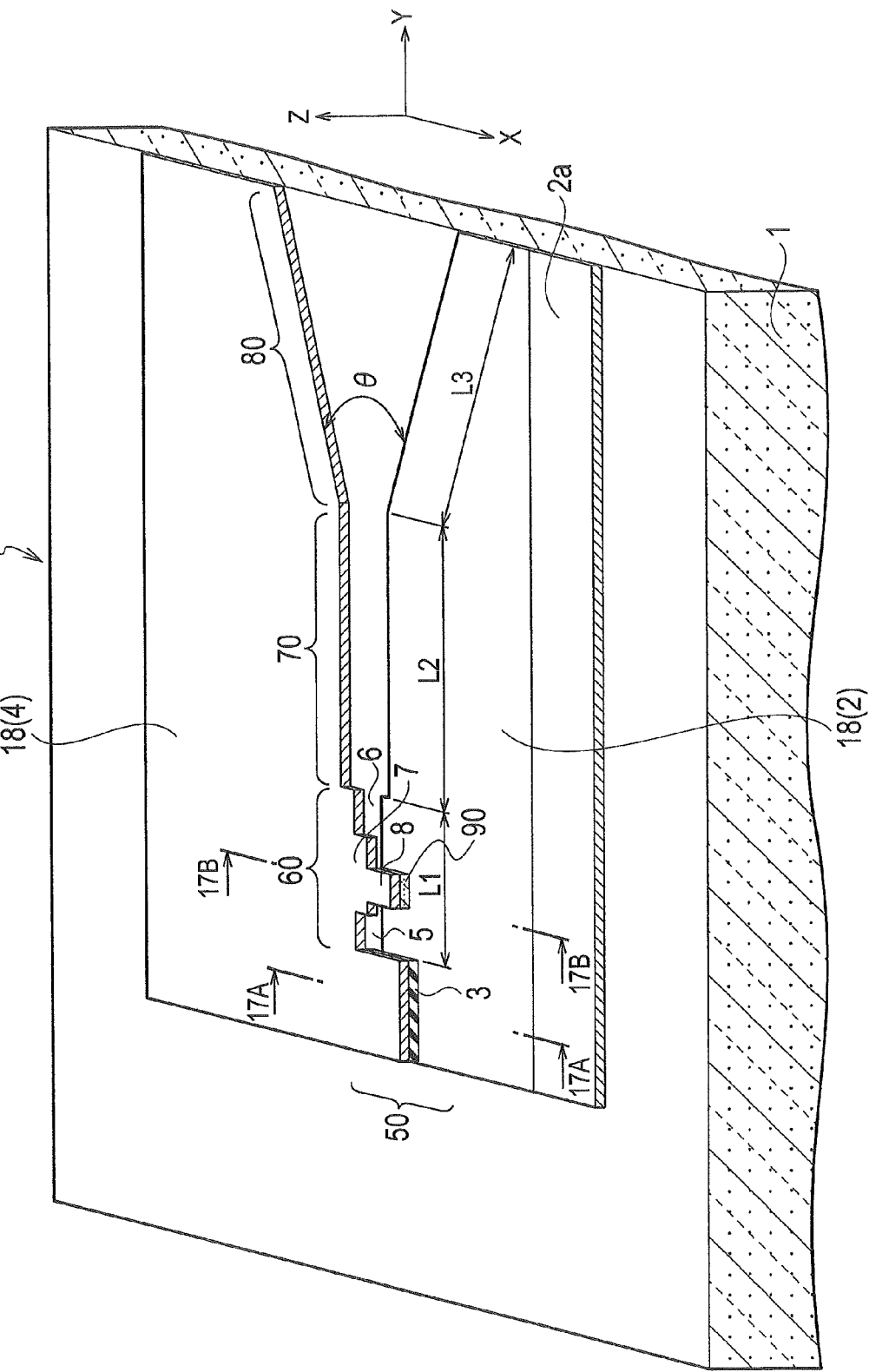
FIG. 16 is a schematic bird's-eye view of a THz oscillation device applied to the solution testing equipment according to the first embodiment.

As shown in FIGS. 1-3, the THz oscillation device 38 includes: an insulator substrate 11; a semiconductor substrate 1 disposed on the insulator substrate 11; second electrodes 2, 2a disposed on the semiconductor substrate 1; a first electrode 4 disposed on the semiconductor substrate 1 so as to be opposite to the second electrode 2; an active element 90 disposed between the first electrode 4 and the second electrode 2; and a MIM reflector 50 disposed so as to be adjacent to the active element 90 at an opposite side of a radiation direction of the THz wave (hv), the MIM reflector 50 formed between the first electrode 4 and the second electrode 2. The detailed structure of the THz oscillation device 38 is shown in FIG. 16.

As shown in FIG. 3, the solution 12 as a test object is contacted with a contact region 14 so as to directly cover a part of the second electrode 2, the active element 90, and the first electrode 4.

Thereby, a radiation pattern of the THz wave (hv) varies in response to the relative permittivity ∈ of the solution 12 as a test object (there will be illustrative examples of the variations in the radiation pattern described below).

Then, ingredient variation etc. in the solution can be tested by comparing the aspect of variation.

The THz oscillation device 38 radiates a THz wave (hv). At this time, the solution 12 is contacted on the active element 90, the first electrode 4, and the second electrode 2 on the surface side of the semiconductor substrate 1 of the THz oscillation device 38, and thereby the radiation pattern of the THz oscillation device 38 varies. Such a solution can be analyzed using the above-mentioned structure.

The active element 90 operates as an oscillation device at a first operational point indicating negative differential resistance. The active element 90 can operate also as a detection device at a second operational point indicating nonlinear characteristics which is not negative resistance region.

The RTD is typical as the active element 90. However, the active element 90 can be composed also from diodes or transistors except for the RTD. There are also applicable, for example, a tunnel transit time (TUNNETT) diode, an impact ionization avalanche transit time (IMPATT) diode, a GaAs based field effect transistor (FET), a GaN based FET, a high electron mobility transistor (HEMT), a heterojunction bipolar transistor (HBT), etc., as other active elements.

The THz oscillation device with such structure generates the THz wave (hv) through an amplitude transition modulation having the first operational point in the negative differential resistance region.

In the aspect to directly contact the solution 12 with the THz oscillation device 38 as shown in FIG. 3, there is the case that the active element 90, the first electrode 4, and the second electrode 2 are etched due to ingredients of the solution.

Figure 4:
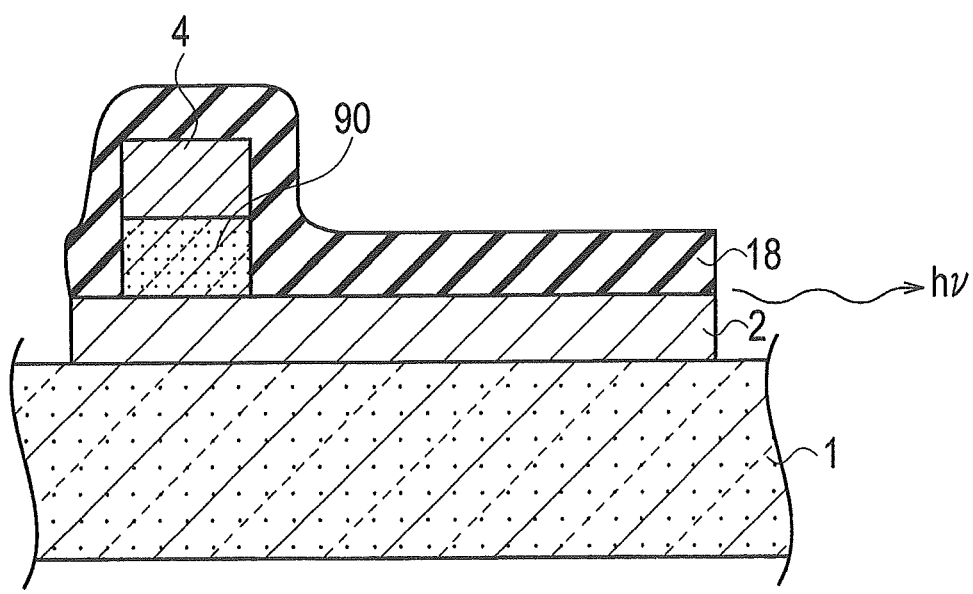
FIG. 4 is a schematic cross-sectional structure diagram in a state where an overlay insulating film is formed on the whole surface of the THz oscillation device applicable to the solution testing equipment according to the first embodiment.

FIG. 4 illustrates a schematic cross-sectional structure in a state where an overlay insulating film 18 is formed all over the THz oscillation device 38, in the THz oscillation device 38 applicable to the solution testing equipment 30 according to the first embodiment.

More specifically, the overlay insulating film 18 may be formed on the active element 90, the first electrode 4, and the second electrode 2, as shown in FIG. 4. The overlay insulating film 18 may be composed of an $SiO_2$ film ranging from 0.1 µm to 10 µm in thickness.

In the present embodiment, the contact region 14 includes a position where the active element 90, the first electrode 4, and the second electrode 2 covered with the overlay insulating film 18 have a place threat.

Figure 5:
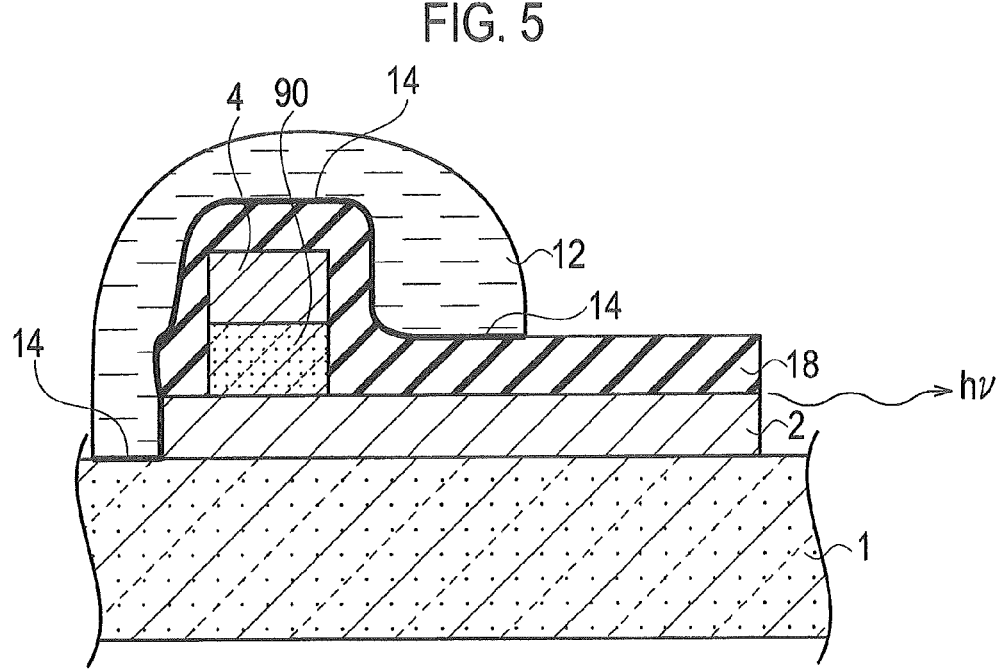
FIG. 5 is a schematic cross-sectional structure diagram in a state where a solution is contacted on the THz oscillation device in the structure shown in FIG. 4.

Furthermore, FIG. 5 illustrates a schematic cross-sectional structure in a state where the solution 12 is contacted on the THz oscillation device 38, in the structure shown in FIG. 4.

More specifically, as shown in FIG. 5, the solution 12 as a test object is contacted on the overlay insulating film 18 covering the position where the active element 90, the first electrode 4, and the second electrode 2 have a place therein.

Thereby, the variation in the ingredient of the solution etc. can be tested by comparing aspects of the variation in the radiation pattern of the THz wave (hv) with one other, in the same manner as the case of FIG. 3.

In the first embodiment, since the overlay insulating film 18 is formed on the active element 90, the first electrode 4, and the second electrode 2 at the surface side of the semiconductor substrate 1, a degree of the variation in the radiation pattern in the THz oscillation device 38 becomes larger, thereby achieving improvement in sensitivity.

In the first embodiment, since the RTD is used for the active element 90 of the THz oscillation device 38, it becomes possible to provide simplified solution testing equipment 30 achieving reduction in size and weight.

Moreover, the active element 90, the first electrode 4, and the second electrode 2 are protected with the overlay insulating film 18, thereby avoiding a situation in which the active element 90, the first electrode 4, and the second electrode 2 are etched due to an ingredient of the solution, and improving durability of the THz oscillation device 38.

Figure 6:
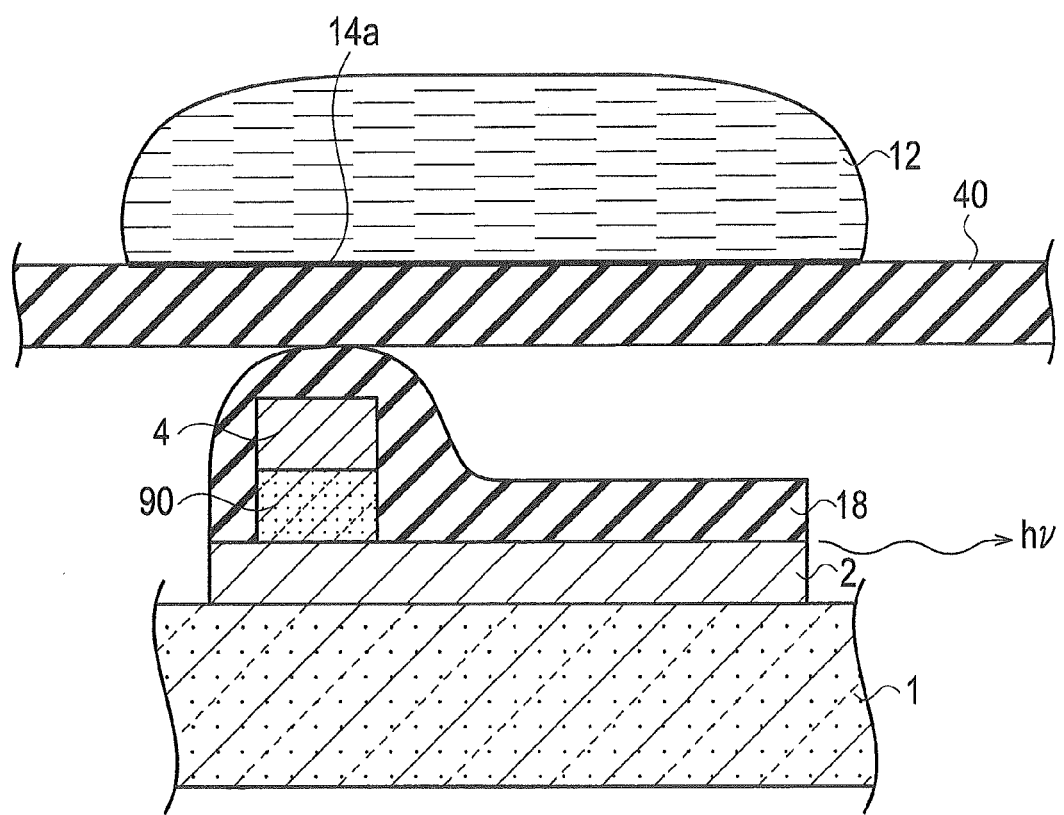
FIG. 6 is a schematic cross-sectional structure diagram in a state where the solution is contacted on the THz oscillation device through a glass plate, in the structure shown in FIG. 4.

FIG. 6 illustrates a schematic cross-sectional structure in a state where the solution 12 is contacted on the THz oscillation device 38 through a glass plate (slide glass) 40.

More specifically, as shown in FIG. 6, the solution testing equipment 30 according to the first embodiment may include the glass plate 40 disposed on the upper side of the overlay insulating film 18, and the solution 12 may be disposed on the THz oscillation device 38 through the glass plate 40. In the present embodiment, the solution 12 is disposed on a contact region 14a on the glass plate 40.

Thereby, the variation in the ingredient of the solution etc. can be tested by comparing aspects of the variation in the radiation pattern of the THz wave with one other, in the same manner as the case of FIG. 3.

According to the structure shown in FIG. 6, since the THz oscillation device 38 is protected with the overlay insulating film 18 and the glass plate 40, the solution 12 as a test object having high reactivity, e.g. strong acid or strong alkali, can also be tested without etching the active element 90, the first electrode 4, and the second electrode 2.

Figure 7A:
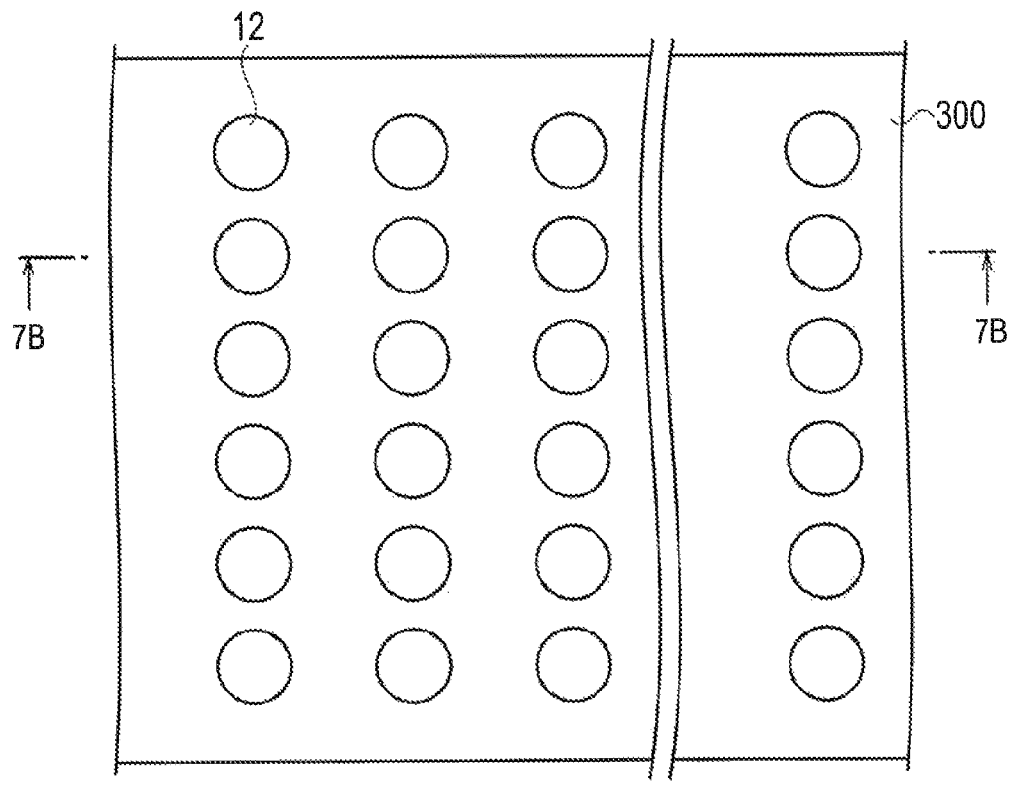
FIG. 7A is a schematic planar pattern configuration diagram of a jig on which a plurality of solution can be loaded, applicable to the solution testing equipment according to the first embodiment.
Figure 7B:
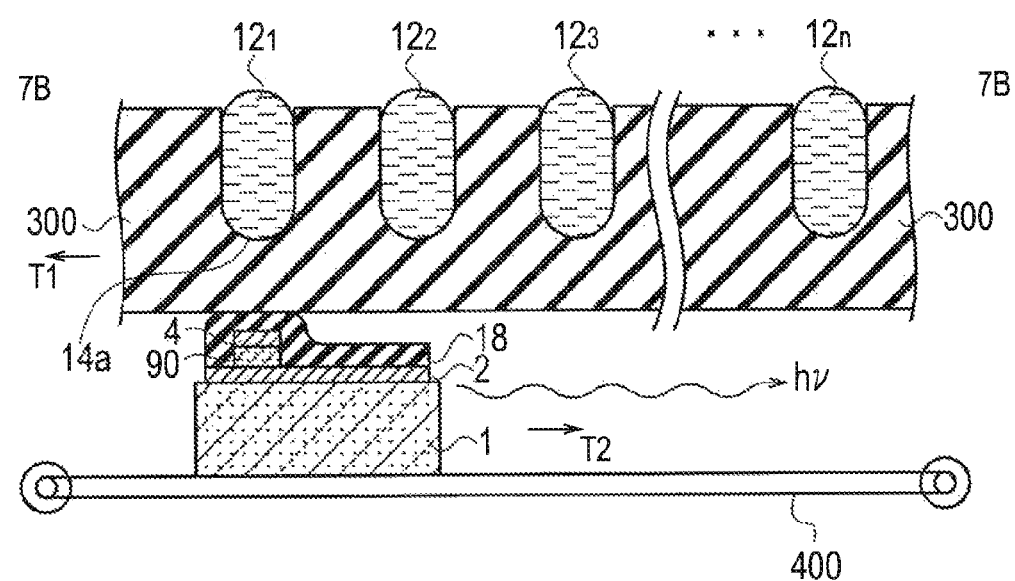
FIG. 7B is a schematic cross-sectional structure diagram taken in the line 7A-7A of FIG. 7A.

FIG. 7A illustrates a schematic planar pattern configuration of a jig 300 on which a plurality of the solutions $12_1$, $12_2$, $12_3$, ..., $12_n$ can be loaded, applicable to the solution testing equipment 30 according to the first embodiment. FIG. 7B illustrates a schematic cross-sectional structure taken in the line 7B-7B of FIG. 7A.

More specifically, in the solution testing equipment according to the first embodiment, as shown in FIG. 7A and FIG. 7B, a plurality of recesses for accommodating the solutions $12_1$, $12_2$, $12_3$, ..., $12_n$ as test objects may be formed on the surface side of the jig 300. In the present embodiment, each recess has a contact region 14a, as shown in FIG. 7B.

A moving unit 400 for moving the jig 300 or the solution testing equipment 30 itself in a horizontal direction may be included in the present embodiment so that each recess having the contact region 14a may be positioned on the upper side of the overlay insulating film 18.

The jig 300 can be composed of a slide glass, a polypropylene plate, etc. Since such a jig 300 is applied thereto, the solutions 121, 122, 123, ..., 12n as test objects can be analyzed without directly contacting the solutions $12_1$, $12_2$, $12_3$, ..., $12_n$ with the THz oscillation device 38.

In addition, as shown in FIG. 7B, each solution $12_1$, $12_2$, $12_3$, ..., $12_n$ can be tested one after another by providing such moving unit 400 for moving the jig 300 in a T1 direction or moving the solution testing equipment in a T2 direction.

Figure 8A:
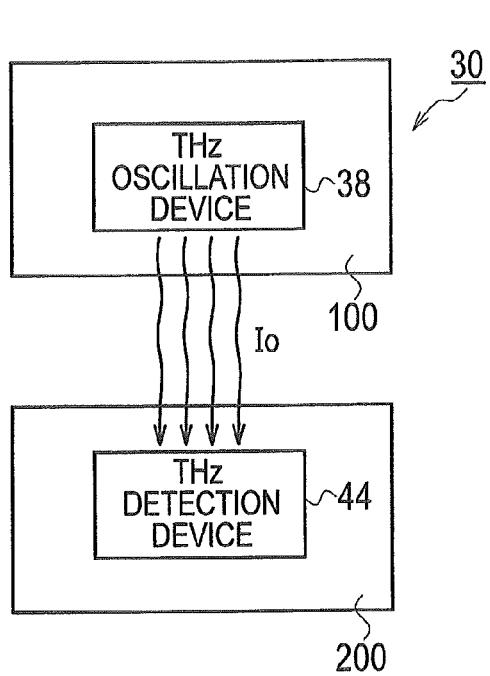
FIG. 8A is a schematic block configuration diagram of solution testing equipment, which is the solution testing equipment according to the first embodiment, in a state where no solution is contacted on the THz oscillation device.
Figure 8B:
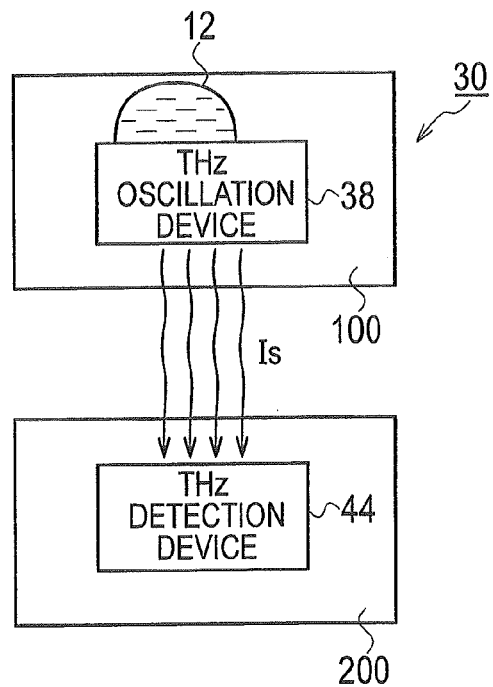
FIG. 8B is a schematic block configuration diagram of solution testing equipment, which is the solution testing equipment according to the first embodiment, in a state where the solution is contacted on the THz oscillation device.

FIG. 8A illustrates a schematic block configuration of the solution testing equipment 30 according to the first embodiment in a state where no solution is contacted thereon. The THz oscillation device 38 and the THz detection device 44 are applied to the solution testing equipment 30. FIG. 8B illustrates a schematic block configuration of the solution testing equipment 30 in a state where the solution 12 is contacted on the THz oscillation device 38.

The THz detection device 44 may include a Schottky barrier diode, in the solution testing equipment 30 according to the first embodiment.

Moreover, the THz detection device 44 may include the RTD in the solution testing equipment 30 according to the first embodiment. In the present embodiment, the THz detection device 44 can detect the variation in the amount of current value in an operational point indicating a negative differential resistance of the RTD, thereby detecting a radiation pattern of the THz wave radiated in response to the relative permittivity of the solution.

Moreover, the THz detection device 44 may have the same structure as that of the THz oscillation device 38.

Figure 9:
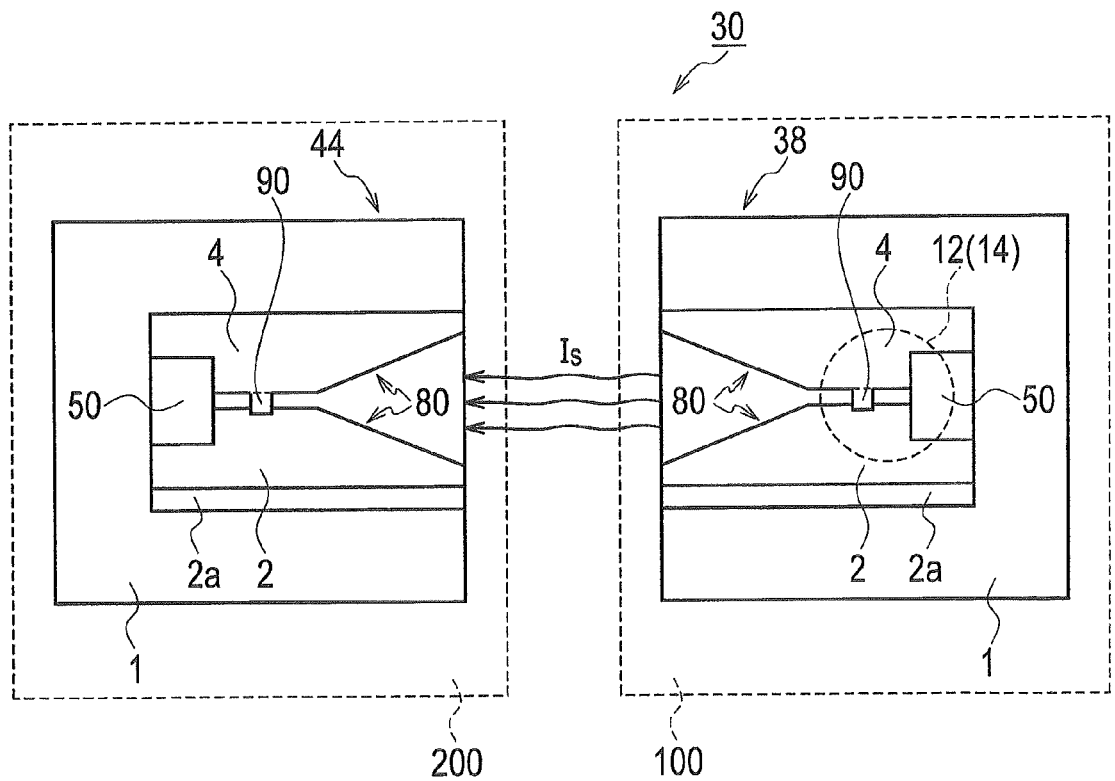
FIG. 9 is a schematic planar pattern configuration diagram of the solution testing equipment according to the first embodiment.

FIG. 9 illustrates a schematic planar pattern configuration of the solution testing equipment 30 according to the first embodiment to which the THz oscillation device 38 and the THz detection device 44 are applied.

In FIG. 9, a THz detection device (i.e., RTD) having the same configuration as the THz oscillation device (i.e., RTD) shown in FIG. 16 is used for each of the THz oscillation device 38 and the THz detection device 44. Accordingly, there can be used the THz oscillation device 38 and the THz detection device 44 each fabricated at the same processing step.

Thus, each structure of the THz transmitter 100 and the THz receiver 200 can be simplified, thereby providing the solution testing equipment 30 which can achieve the oscillation and the detection of the THz electromagnetic wave with high sensitivity and low noise.

As shown in FIG. 9, the solution testing equipment 30 according to the first embodiment includes: a THz transmitter 100 including a THz oscillation device 38; and a THz receiver 200 including a THz detection device 44, in which the THz oscillation device 38 generates THz wave $I_s$ with an amplitude transition modulation having a first operational point in a negative differential resistance region, and the THz detection device 44 detects the THz wave $I_s$ generated from the THz oscillation device 38 by having a second operational point in a non-linearity region which is not the negative resistance characteristics.

In addition, a horn apertural area 80 is formed to be adjacent to an active element 90 in each of the THz transmitter 100 and the THz receiver 200.

Moreover, the solution 12 as a test object is contacted so as to cover the active element 90 at the THz transmitter 100 side.

Accordingly, since the radiation pattern of the THz wave $I_s$ varies in response to the relative permittivity $\in$ of the solution 12 as a test object, the variation in the ingredient of solution etc. can be tested by comparing the aspect of variation.

More specifically, in the solution testing equipment 30 according to the first embodiment, the radiation patterns of the THz wave $I_s$ corresponding to the various solutions 12 is previously obtained to be recorded as reference radiation patterns, and then the radiation pattern obtained from the solution 12 is matched with the reference radiation patterns, thereby identifying the solution 12.

Figure 10:
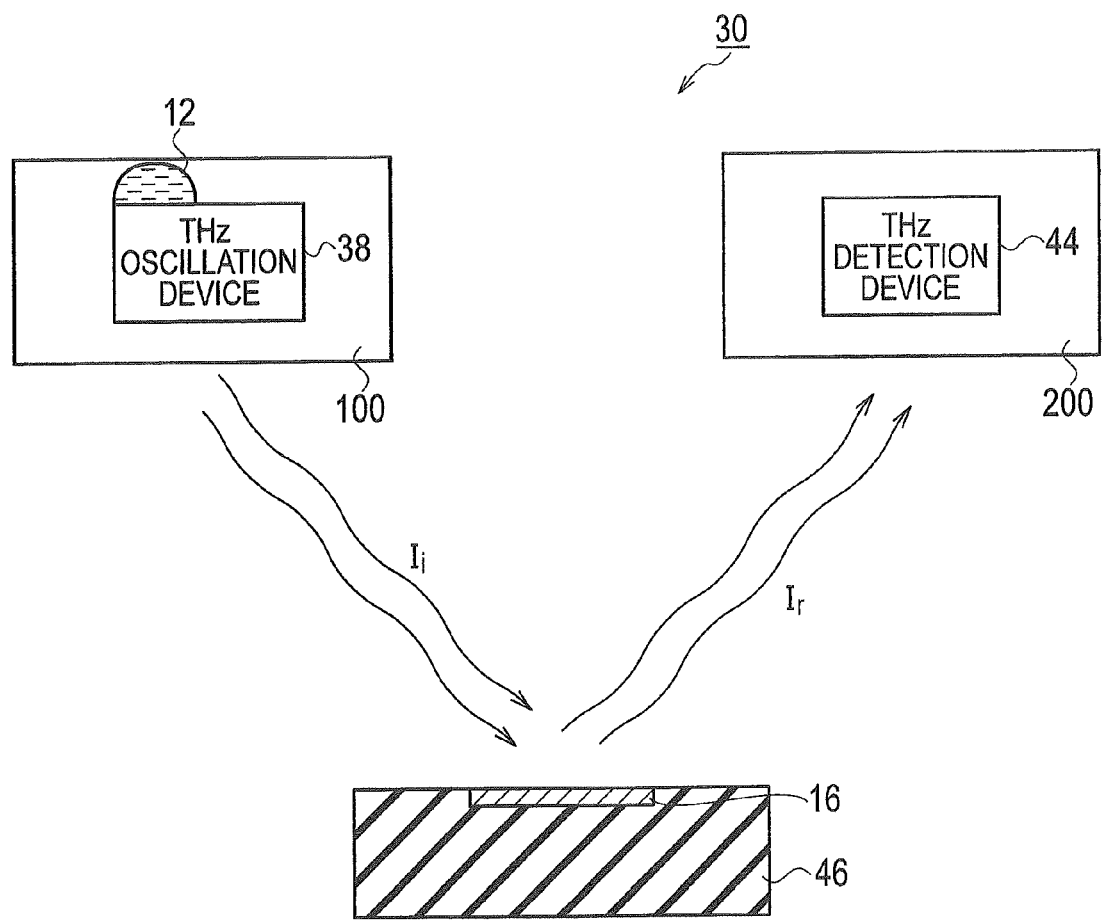
FIG. 10 is a schematic diagram for explaining an aspect that a THz wave $I_i$ output from the THz oscillation device is input to a reflector disposed on a glass substrate, and then the THz wave $I_r$ reflected from the reflector is detected by the THz detection device.

FIG. 10 schematically illustrates an aspect that the THz wave $I_i$ output from the THz oscillation device 38 is input into a reflector 16 disposed on the glass substrate 46, and then the THz wave $I_r$ reflected from the reflector 16 is detected with the THz detection device 44. Moreover, the specific structure thereof is illustrated as shown in FIG. 11.

Figure 11:
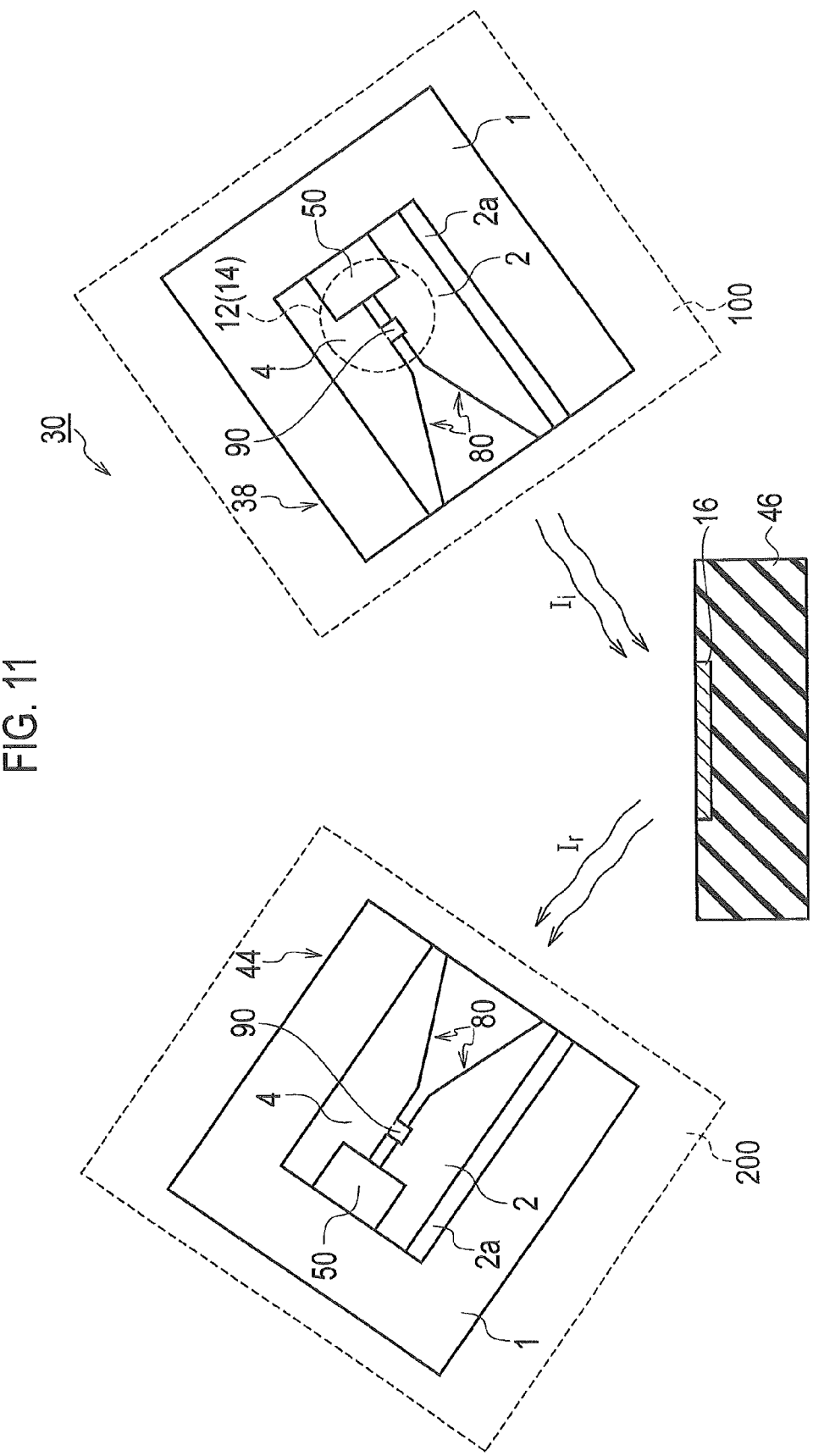
FIG. 11 is a specific configuration diagram of FIG. 10.

More specifically, as shown in FIGS. 10 and 11, the solution testing equipment 30 according to the first embodiment includes the reflector 16 may be configured to reflect the THz wave $I_i$ oscillated from the THz oscillation device 38, and the THz detection device 44 may be configured to receive the THz wave $I_r$ reflected through the reflector 16.

Thus, it becomes unnecessary to dispose the THz transmitter 100 and the THz receiver 200 to be opposite to each other, thereby improving convenience of the solution test.

Figure 12:
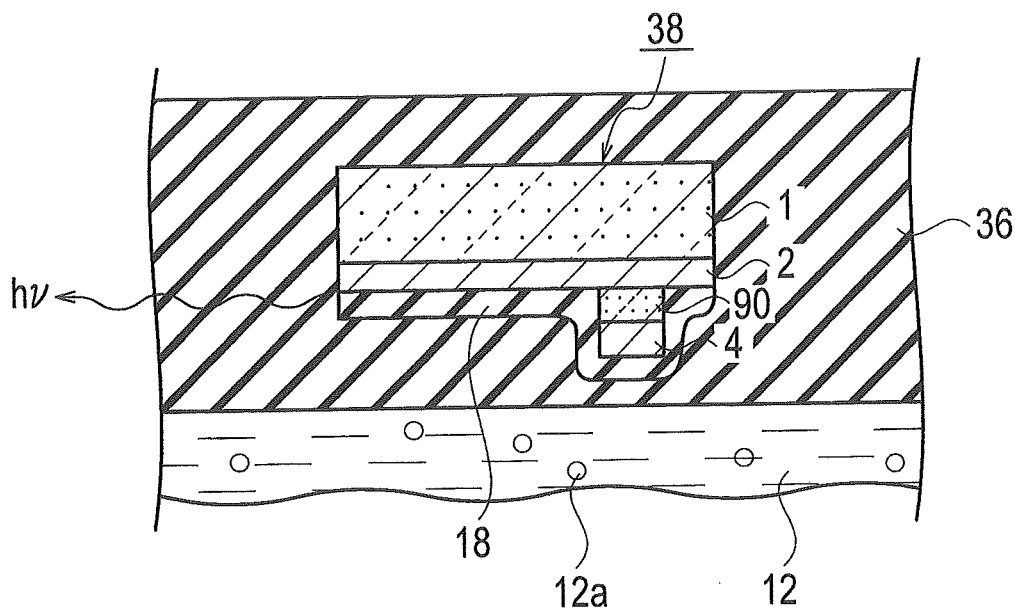
FIG. 12 is a schematic diagram for explaining an example in which the solution testing equipment according to the first embodiment is molded with a resin layer, and then is contacted with a solution containing cells.

FIG. 12 illustrates a schematic diagram for explaining an example in which the solution testing equipment according to the first embodiment is molded with a resin layer, and then is contacted with a solution containing cells.

More specifically, the THz oscillation device 38 may be provided with a resin layer 36 configured to seal the whole of the THz oscillation device 38, in the solution testing equipment according to the first embodiment.

Moreover, the solution 12 may contain a predetermined solvent, and predetermined cells 12a diffused into the predetermined solvent.

As shown in FIG. 12, the solution testing equipment is used so as to contact a side provided with the active element 90 etc. with the solution 12 into which the predetermined cells 12a are diffused.

The solution testing equipment according to the first embodiment can obtain information on cells ranging from approximately 30 µm to approximately 50 µm in width and approximately 2 µm to approximately 3 µm in height by using the THz wave, for example.

Figure 13:
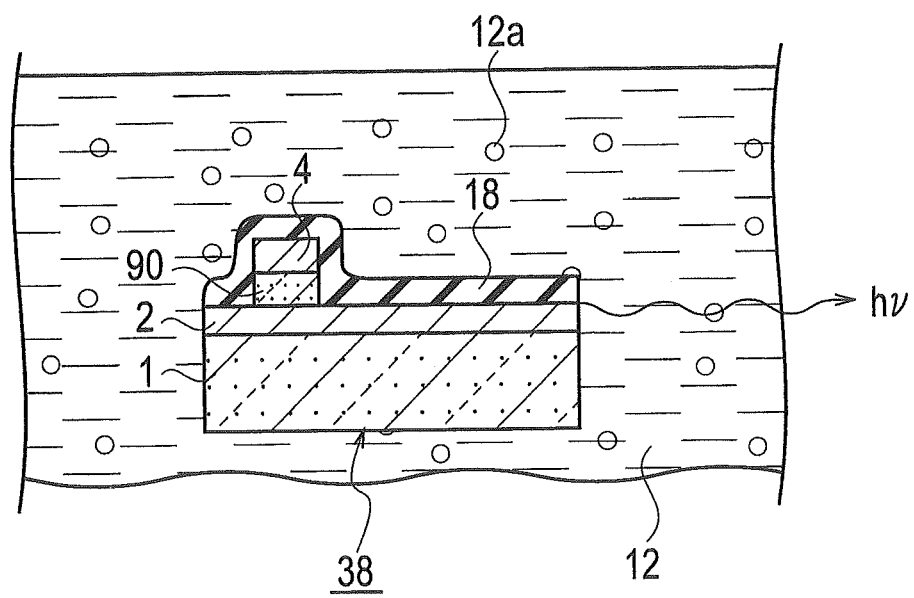
FIG. 13 is a schematic diagram for explaining an example in which the solution testing equipment according to the first embodiment is immersed in the solution containing cells.

Moreover, FIG. 13 illustrates a schematic diagram for explaining an example in which the solution testing equipment according to the first embodiment is immersed in the solution 12 containing cells 12a.

Accordingly, since the radiation pattern of the THz wave varies in response to the relative permittivity ∈ of the solution 12 into which the cells 12a are diffused as a test object, the variation of the cell 12a in the solution 12, etc. can be tested by comparing the aspect of variation.

In connection with the example shown in FIG. 13, if the solution testing equipment is encapsulated in a capsule measuring approximately 1 cm in outside diameter and approximately 2 cm in full length, the encapsulated solution testing equipment is administered orally into the human body as a capsule endoscope, and thereby a state in alimentary canals, e.g. the stomach, the small intestine, and the large intestine, can also be tested using the THz wave. If the solution testing equipment is used as medical applications, e.g. a microcapsule, a detection system for the THz wave may also be included therein. For example, since the transmission distance of the THz wave in the water is approximately 200 µm, the detection system of the THz wave may also be disposed within the range of approximately 200 µm. Moreover, since the THz wave can be transmitted if the liquid is ethanol, usage as shown in FIG. 13 is adoptable.

Figure 14:
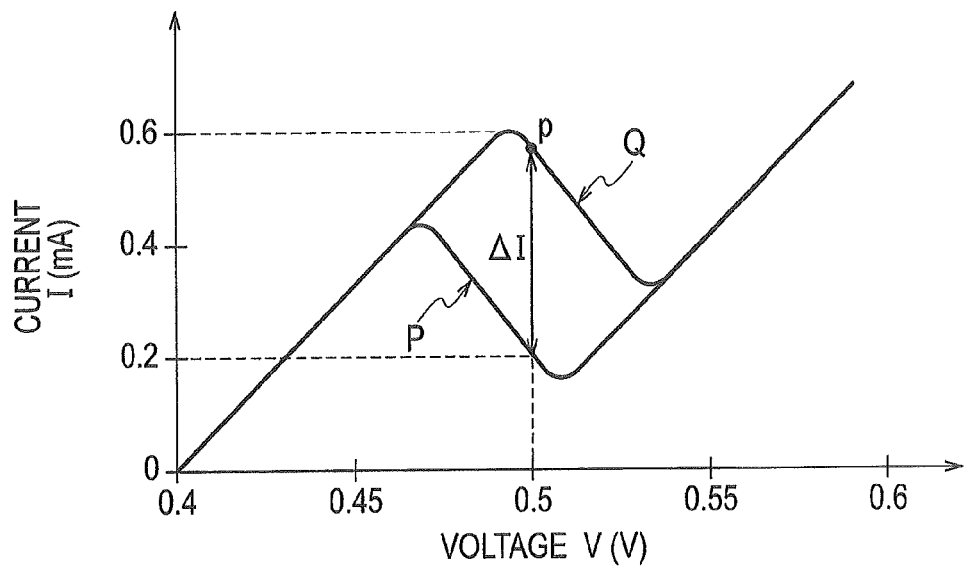
FIG. 14 is a diagram for explaining a variation of forward current-voltage characteristics before and after irradiating the THz wave of the THz detection device applied to the solution testing equipment according to the first embodiment.

FIG. 14 illustrates a diagram for explaining a variation of forward current-voltage characteristics before and after irradiating the THz wave of the THz detection device applied to the solution testing equipment according to the first embodiment.

More specifically, FIG. 14 illustrates characteristic variations at the time of irradiating of the THz wave (P) and at the time of unirradiating of the THz wave (Q) under room-temperature operation, which is an example of current/voltage characteristics of the THz detection device (RTD) 44 applied to the solution testing equipment 30 according to the first embodiment.

As shown in FIG. 14, it is and the THz electromagnetic wave under the room-temperature operation can be detected with excellent sensitivity by setting bias voltage as 0.5V. If the bias voltage is set to 0.5V, it is biased to the point p at the time of unirradiating of the THz wave (Q); but the current varies more greatly at the time of irradiating of the THz wave (P) and the amount of current variation ΔI is approximately 0.4 mA.

Figure 15:
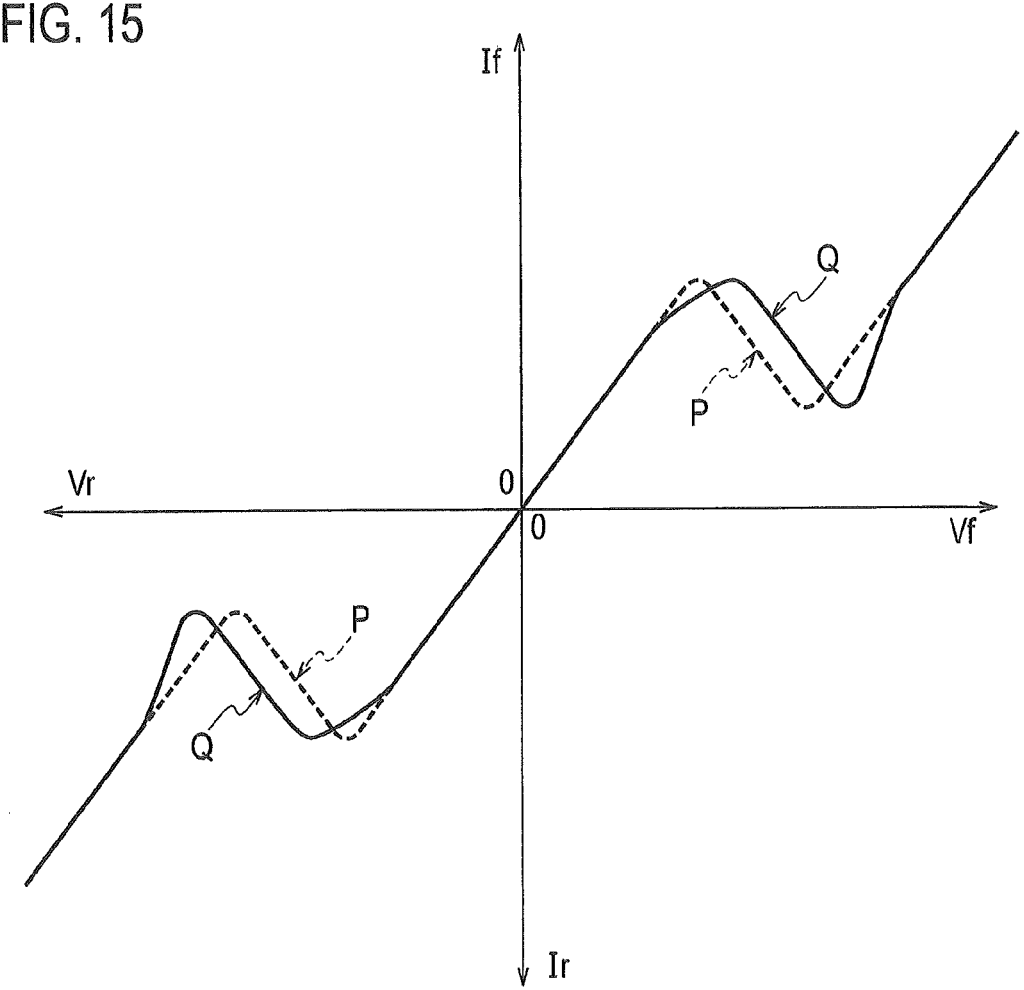
FIG. 15 is a diagram for explaining variations in forward and reverse current voltage characteristics before and after irradiating the THz wave of the THz detection device applied to the solution testing equipment according to the first embodiment.

FIG. 15 illustrates schematically variations of the forward and reverse current voltage characteristics at the time of irradiating of the THz wave (P) and at the time of the unirradiating of the THz wave (Q), under the room-temperature operation of the THz detection device 44 applied to the solution testing equipment 30 according to the first embodiment.

Note that designations of the forward and reverse are expediencies. If one is determined as forward, the other will be determined as reverse. The reason is that the RTD has two-terminal structure and has negative resistance regions in both of the forward current voltage characteristics and the reverse current voltage characteristics.

Figure 17A:
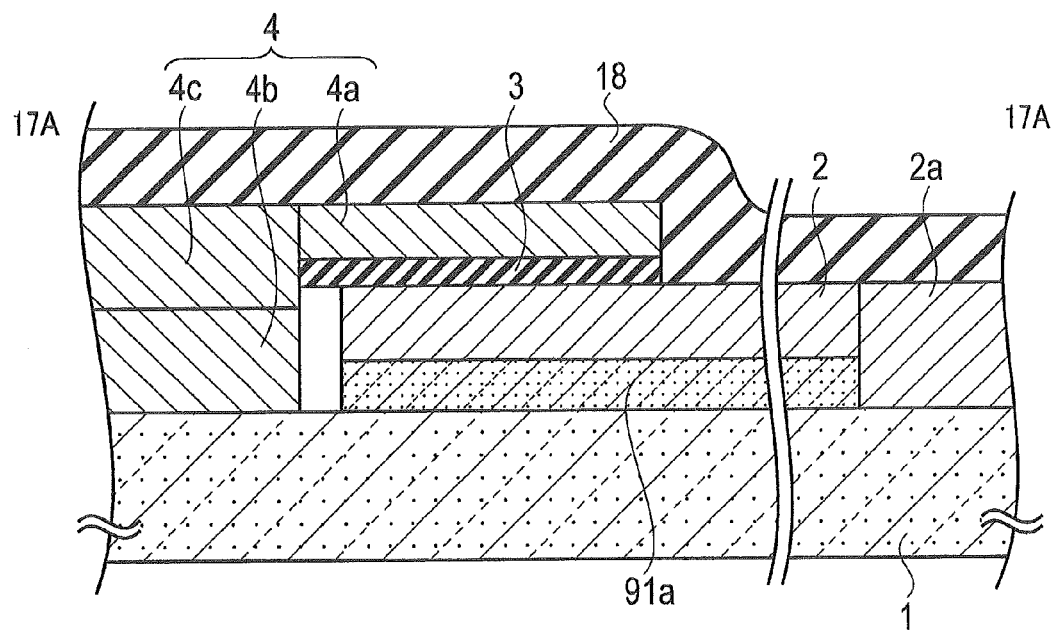
FIG. 17A is a schematic cross-sectional structure diagram taken in the line 17A-17A of FIG. 16.

FIG. 16 illustrates a schematic bird's-eye view structure of the THz oscillation device 38 applied to the solution testing equipment 30 according to the first embodiment. FIG. 17A illustrates a schematic cross-sectional structure taken in the line 17A-17A of FIG. 16, and FIG. 17B illustrates a schematic cross-sectional structure taken in the line 17B-17B of FIG. 16.

The THz oscillation device 38 applied to the solution testing equipment 30 according to the first embodiment includes an active element 90 having asymmetrical forward and reverse current voltage characteristics. Such a THz oscillation device 38 can operate as an oscillation device at a first operational point indicating negative differential resistance, and can operate as a detection device at a second operational point indicating nonlinear characteristics which are not negative resistance regions.

Figure 17B:
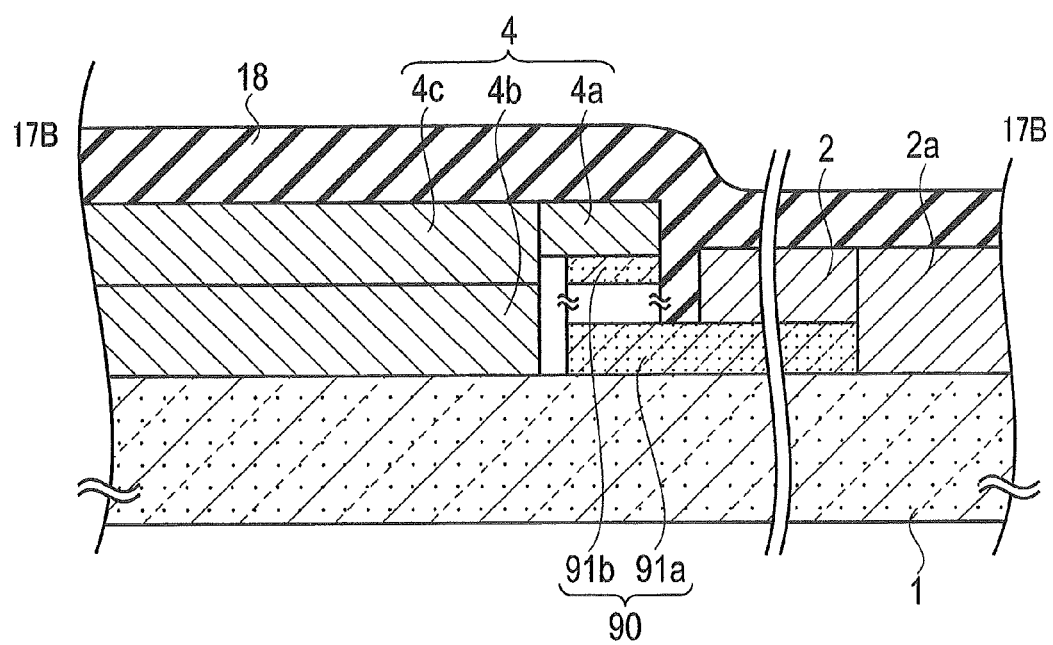
FIG. 17B is a schematic cross-sectional structure diagram taken in the line 17B-17B of FIG. 16.

As shown in FIGS. 16, 17A and 17B, the schematic bird's-eye view structure of the THz oscillation device 38 applied to the solution testing equipment 30 according to the first embodiment includes: a semiconductor substrate 1; second electrodes 2, 2a disposed on the semiconductor substrate 1; an inter-electrode insulating layer 3 disposed on the second electrode 2; a first electrode 4 (4a, 4b, 4c) disposed via the inter-electrode insulating layer 3 toward the second electrode 2, the first electrode 4 disposed to be opposite to the second electrode 2 on the semiconductor substrate 1; an MIM reflector 50 formed between the first electrode 4a and the second electrode 2 so that the inter-electrode insulating layer 3 is sandwiched therebetween; a resonator 60 disposed between the first electrode 4 and the second electrode 2 opposite to each other on the semiconductor substrate 1, the resonator 60 adjacent to the MIM reflector 50; a waveguide 70 disposed between the first electrode 4 and the second electrode 2 opposite to each other on the semiconductor substrate 1, the waveguide 70 adjacent to the resonator 60; and a horn apertural area 80 disposed between the first electrode 4 and the second electrode 2 opposite to each other on the semiconductor substrate 1, the horn apertural area 80 adjacent to the waveguide 70, in which the active element 90 is disposed at a substantially central part of the resonator 60.

As shown in FIGS. 16, 17A and 17B, an overlay insulating film 18 is formed on the first electrode 4 (4a, 4b, 4c) and the second electrode 2, 2a. For example, the overlay insulating film 18 is composed of an $SiO_2$ film ranging from approximately 0.1 µm to approximately 10 µm in thickness. The overlay insulating film 18 is preferably formed ranging from approximately 0.6 µm to approximately 5 µm in thickness.

The horn apertural area 80 is composed of an aperture horn antenna. The angular aperture θ of the horn apertural area is preferable to set as equal to or less than approximately 10 degrees, for example, from the viewpoint of giving the directional characteristics in the radiation direction of the THz wave (hv). The length L3 of the horn apertural area 80 is equal to or less than approximately 700 µm, for example. The aperture width in the tip region of the horn apertural area 80 is approximately 160 µm, for example.

The waveguide 70 is disposed at the apertural area of the resonator 60. The length L2 of the waveguide 70 is equal to or less than approximately 700 µm, for example. The distance between the first electrode 4 and the second electrode 2 in the waveguide 70 is approximately 24 µm, for example.

The horn shape of the horn apertural area 80 is a structure required in order to extract the THz wave (hv) in the air. Depending on the horn shape, the THz wave (hv) can be efficiently extracted with sufficient impedance matching property in the air. In addition, the shape of the horn may be not only a linearity shape, but also a nonlinear shape, a curve profile, a secondary curve profile, a parabola shape, a stair-like shape, etc.

Two recessed regions 5, 6 are formed, and a protruded region 7 is inserted between the two recessed regions 5, 6, in the resonator 60. A salient region 8 is formed at the substantially central part of the protruded region 7 of the first electrode 4, and the active element 90 is disposed at an under side of the salient region 8 so as to be inserted between the salient region 8 and the second electrode 2.

The length L1 of the resonator 60 is equal to or less than approximately 30 µm, for example. The length of the salient region 8 is equal to or less than approximately 6 µm, for example. The width of the recessed regions 5, 6 (distance between the first electrode 4 and the second electrode 2) is approximately 4 µm, for example. The size of the active element 90 is approximately 1.4 µm$^2$, for example. However, the size of the active element 90 is not be limited to such a value, and may be equal to or less than approximately 5.3 µm$^2$, for example. The detailed structure of the active element 90 will be described later. The size of each part in the resonator 60 is not limited to the aforementioned size, and may be appropriately designed in accordance with the frequency of the THz wave (hv) to be radiated.

As shown in FIG. 16, the distance between the first electrode 4 and the second electrode 2 of the part on which the resonator 60 is formed is narrower compared with the distance between the first electrode 4 and the second electrode 2 in the waveguide 70.

The MIM reflector 50 is disposed at the closed area in the opposite side of the apertural area of the resonator 60. Because of the layered structure of the MIM reflector 50 composed of metal/insulator/metal, the first electrode 4 and the second electrode 2 are short-circuited in terms of high frequency. Moreover, the MIM reflector 50 produces an effect to reflect high-frequency waves as it is open in terms of direct current.

Each of the first electrode 4 (4a, 4b, 4c) and the second electrodes 2, 2a is composed of metal layered structure, e.g., Au/Pd/Ti, and the Ti layer is a buffer layer for excellent contact condition with the semiconductor substrate 1 composed of a semi insulating InP substrate described below. The thickness of each part of the first electrode 4 (4a, 4b, 4c) and the second electrodes 2, 2a is approximately hundreds of nanometers, for example, and the layered-structure planarized as a whole as shown in FIGS. 17A and 17B is achieved. Each of the first electrode 4 (4a, 4b, 4c) and the second electrodes 2, 2a can be formed with a vacuum deposition method or a sputtering technique.

More particularly, the first electrode 4a and the first electrode 4c are composed of Au/Pd/Ti, for example, and the first electrode 4b is composed of Au/Ti, for example. The second electrode 2 is composed of Au/Pd/Ti, for example, and the second electrode 2a is composed of Au/Ti, for example.

Note that when an extraction electrode is formed from a bonding wire (not shown), the Ti layer which forms a surface layer of the first electrode 4b is preferable to be removed in order to reduce contact resistance. Similarly, when an extraction electrode is formed from a bonding wire (not shown), the Ti layer which forms a surface layer of the second electrode 2a is preferable to be removed in order to reduce contact resistance.

The inter-electrode insulating layer 3 can be formed of an $SiO_2$ film, for example. Other films, e.g. an $Si_3N_4$ film, a SiON film, an $HfO_2$ film, an $Al_2O_2$ film, etc. are also applicable to the inter-electrode insulating layer 3.

The thickness of the inter-electrode insulating layer 3 can be determined in consideration of the geometric plane size of the MIM reflector 50 and the required capacitor value on circuit characteristics, for example, and may be tens to hundreds of nanometers. The inter-electrode insulating layer 3 can be formed by using the chemical vapor deposition (CVD) method or the spattering technique.

As shown in FIGS. 16, 17A and 17B, the THz oscillation device 38 applied to the solution testing equipment 30 according to the first embodiment includes: an inter-electrode insulating layer 3 disposed on a second electrode 2; a first electrode 4 (4a, 4b, 4c) disposed via the inter-electrode insulating layer 3 toward the second electrode 2, the first electrode 4 disposed to be opposite to the second electrode 2 on the semiconductor substrate 1; an MIM reflector 50 formed between the first electrode 4a and the second electrode 2 so that the inter-electrode insulating layer 3 is sandwiched therebetween; a resonator 60 disposed between the first electrode 4 and the second electrode 2 opposite to each other on the semiconductor substrate 1, the resonator 60 adjacent to the MIM reflector 50; a waveguide 70 disposed between the first electrode 4 and the second electrode 2 opposite to each other on the semiconductor substrate 1, the waveguide 70 adjacent to the resonator 60; and a horn apertural area 80 disposed between the first electrode 4 and the second electrode 2 opposite to each other on the semiconductor substrate 1, the horn apertural area 80 adjacent to the waveguide 70, in which the active element 90 is disposed at a substantially central part of the resonator 60.

Figure 18A:
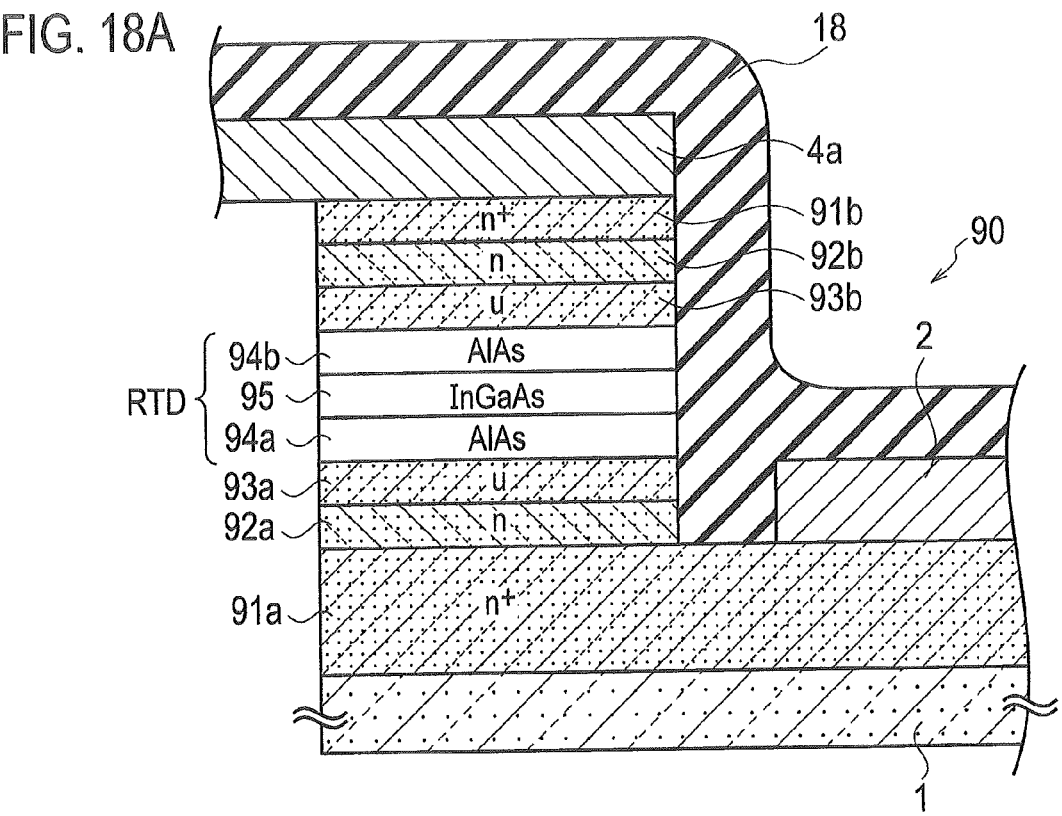
FIG. 18A is a schematic cross-sectional structure diagram of RTD applied to the solution testing equipment according to the first embodiment.
Figure 18B:
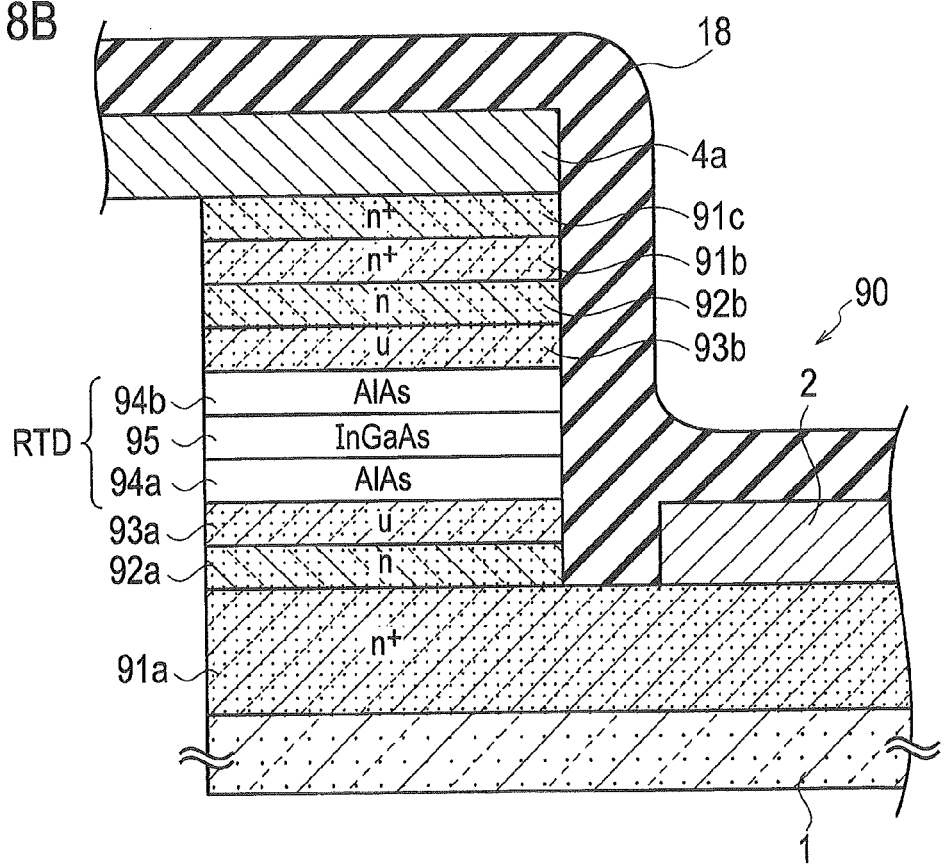
FIG. 18B is a schematic cross-sectional structure diagram of a modified example of FIG. 18A.

FIG. 18A illustrates a schematic cross-sectional structure of the RTD applied to the solution testing equipment 30 according to the first embodiment, and FIG. 18B illustrates a schematic cross-sectional structure of a modified example thereof.

As shown in FIG. 18A, a constructional example of the RTD as the active element 90 applied to the solution testing equipment 30 according to the first embodiment includes: an n$^+$ InGaAs layer 91a disposed on the semiconductor substrate 1 composed of a semi insulating InP substrate, the n$^+$ InGaAs layer 91a highly doped with an n type impurity; an n-InGaAs layer 92a disposed on the n$^+$ InGaAs layer 91a, the n-InGaAs layer 92a doped with an n type impurity; an undoped InGaAs layer 93b disposed on the n-InGaAs layer 92a; an RTD portion disposed on the InGaAs layer 93b, the RTD portion composed of an undoped AlAs layer 94a/an undoped InGaAs layer 95/an undoped AlAs layer 94b; an undoped InGaAs layer 93b disposed on the undoped AlAs layer 94b; an n-InGaAs layer 92b disposed on the undoped InGaAs layer 93b, the n-InGaAs layer 92b doped with an n type impurity; an n$^+$ InGaAs layer 91b disposed on the n-InGaAs layer 92b, the n$^+$ InGaAs layer 91b highly doped with an n type impurity; a first electrode 4a disposed on the n$^+$ InGaAs layer 91b; and a second electrode 2 disposed on the n$^+$ GaInAs layer 91a.

According to the modified example, as shown in FIG. 18B, an n$^+$ GaInAs layer 91c highly doped with the n type impurity is further disposed on the n$^+$ GaInAs layer 91b highly doped with the n type impurity, thereby making excellent contact with the first electrode 4a.

As shown in FIGS. 18A and 18B, the RTD portion is formed so that the undoped InGaAs layer 95 is sandwiched between the undoped AlAs layers 94a and 94b. The RTD portion layered in this way is structured to be ohmic-connected to the second electrode 2 and the first electrode 4 via the n-InGaAs layers 92a, 92b and the n$^+$ InGaAs layers 91a, 91b or 91a, 91b 91c, inserting the respective undoped InGaAs layers 93a, 93b used as a spacer therebetween.

In the structure shown in FIGS. 18A and 18B, an undoped $In_{0.53}Ga_{0.47}As$ layer may be further inserted between the semiconductor substrate 1 composed of the semi insulating InP substrate and the n$^+$ InGaAs layers 91a highly doped with the n type impurity.

In this case, the thickness of each layer is as follows, for example.

The thicknesses of the n$^+$ InGaAs layers 91a, 91b, 91c are respectively approximately 400 nm, approximately 15 nm, and approximately 8 nm, for example. The thicknesses of the n-GaInAs layers 92a, 92b are substantially equivalent to each other, and are respectively approximately 25 nm, for example. The thicknesses of the undoped InGaAs layers 93a, 93b are respectively approximately 2 nm, and approximately 20 nm, for example. The thicknesses of the undoped AlAs layers 94a, 94b are equivalent to each other, and are respectively approximately 1.1 nm, for example. The thickness of the undoped GaInAs layer 95 is approximately 4.5 nm, for example.

In the schematic cross-sectional structure of the RTD applied to the solution testing equipment 30 according to the first embodiment, the thickness of the undoped InGaAs layer 93a is set to approximately 2 nm and the thickness of the undoped InGaAs layer 93b is asymmetrically set to approximately 20 nm, in which the undoped InGaAs layer 93a, 93b sandwich the RTD portion composed of the undoped AlAs layer 94a/undoped InGaAs layer 95/undoped AlAs layer 94b, and thereby the forward and reverse current-voltage (I-V) characteristics can be made asymmetry.

In the schematic cross-sectional structure of the RTD applied to the solution testing equipment 30 according to the first embodiment, the asymmetric epitaxial structure is adapted, and thereby the forward I-V characteristics and the reverse I-V characteristics become asymmetrical. Accordingly, it becomes possible to use the oscillation device and the detection device properly by changing the applied voltage.

As the THz detection device 44, the sensitivity of the detection using diode becomes higher as the nonlinearity of the I-V characteristics are larger. However, the RTD can be used as a highly sensitivity detector since the RTD exhibits negative resistance, and is larger in nonlinearity.

In the present embodiment, the composition ratio x of In of each layer composed of $In_xGa_{1-x}As$ is as follows, for example.

The composition ratio: x=0.53 in the n$^+$ InGaAs layers 91a, 91b; x=0.7 in the n$^+$ InGaAs layer 91c; x=0.53 in the n-GaInAs layers 92a, 92b; x=0.53 in the undoped InGaAs layer 93b; and x=0.8 in the undoped GaInAs layer 95.

In the present embodiment, the doping level of each layer is as follows, for example.

The doping level of the n$^+$ InGaAs layers 91a, 91b is approximately 2.00E+19 (cm$^{-3}$); the doping level of the n$^+$ InGaAs layer 91c is approximately 2.00E+19 (cm$^{-3}$); and the doping level of the n-GaInAs layers 92a, 92b is approximately 3.00E+18 (cm$^{-3}$), silicon (Si) can be applied to the dopant in each case, for example.

In addition, in the layered structure shown in FIGS. 18A and 18B, an overlay insulating film 18 is formed on the first electrode 4a and the second electrode 2. The overlay insulating film 18 can be formed of an $SiO_2$ film, an $Si_3N_4$ film, an SiON film, an $HfO_2$ film, and an $Al_2O_3$ film, etc. or a multilayer film composed thereof, and then can be deposited on a sidewall part of the layered structure shown in FIGS. 18A and 18B.

The inter-electrode insulating layer 3 can be formed by using the CVD method or the spattering technique.

The size of the RTD composing the active element 90 is equal to or less than approximately 1.4 µm$^2$, for example. For example, the oscillation frequency observed at a room temperature is approximately 300 GHz. For example, the current density Jp of the device at the time of oscillation is approximately 7 mA/µm$^2$.

—Circuit Configuration—

Figure 19A:
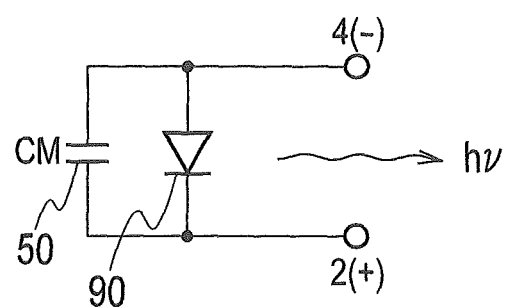
FIG. 19A is a schematic circuit configuration diagram of the THz oscillation device applied to the solution testing equipment according to the first embodiment.

A schematic circuit configuration of the THz oscillation device 38 applied to the solution testing equipment 30 according to the first embodiment is illustrated with the RTD composing the active element 90, and a parallel circuit of capacitor CM composing the MIM reflector 50, as shown in FIG. 19A. The cathode of the RTD is connected to the first electrode 4, and the anode of the RTD is connected to the second electrode 2. Accordingly, the positive voltage is applied to the first electrode 4, and the negative voltage is applied to the second electrode 2. In an oscillation state, the THz waves (hv) spread with sufficient directivity to the Y axial direction which is the aperture opening direction of the horn apertural area.

Figure 19B:
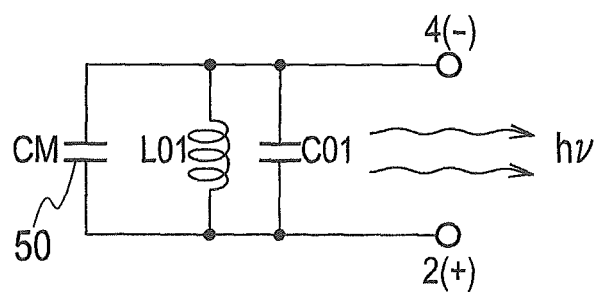
FIG. 19B is a simplified equivalent circuit configuration diagram of the THz oscillation device according to the first embodiment.

FIG. 19B shows a simplified equivalent circuit structure corresponding to the structure shown in FIG. 19A. The RTD composing the active element 90 can be indicated with the parallel circuit composed of the capacitor C01 and the inductor L01. Since the capacitor CM of the MIM reflector 50 is further connected thereto in parallel, the oscillation frequency f of the THz wave (hv) is indicated with the following equation:

$$f=1/[2\pi(L01(C01+CM)^{1/2}])$$

Figure 20A:
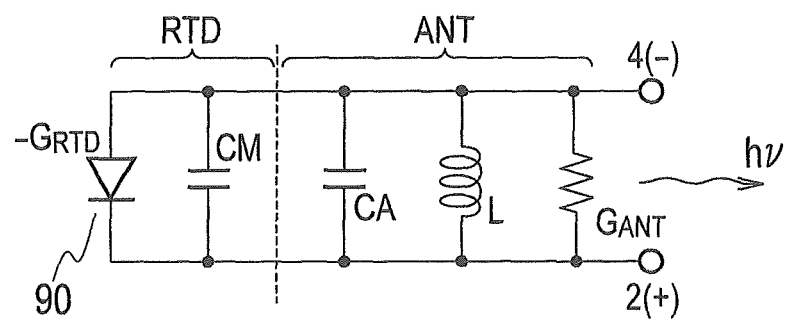
FIG. 20A is a schematic equivalent circuit configuration diagram also including an antenna system of the THz oscillation device applied to the solution testing equipment according to the first embodiment.

In a schematic equivalent circuit structure also including an antenna system of the THz oscillation device 38 applied to the solution testing equipment 30 according to the first embodiment, as shown in FIG. 20A, a parallel circuit composed of an antenna inductor L, an antenna capacitor CA, and an antenna radiation resistance $G_{ANT}$ indicating an antenna (ANT) system is connected in parallel to the parallel circuit composed of the active element 90 and the capacitor CM indicating a diode (RTD) system.

Figure 20B:
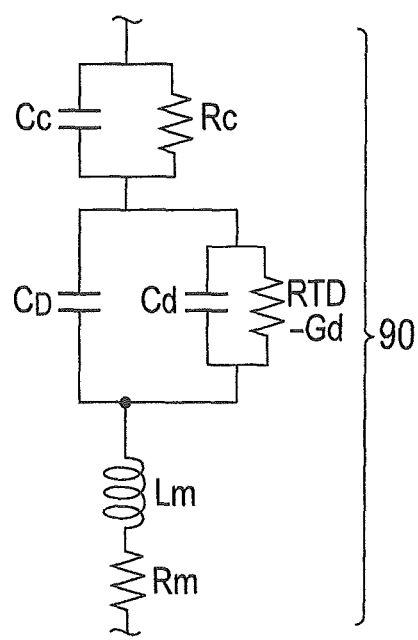
FIG. 20B is an equivalent circuit configuration diagram of the RTD shown in FIG. 20A.

As shown in FIG. 20B, the equivalent circuit structure of the RTD composing the active element 90 shown in FIG. 20A is structured so that a parallel circuit of a contact portion; a parallel circuit of a diode portion; and a series circuit of a mesa portion are connected in series on another. The parallel circuit of the contact portion is composed of a contact resistance Rc and a contact capacitor Cc. The parallel circuit of the diode portion is composed of an external diode capacitor CD, an internal diode capacitor Cd, and a diode negative resistance (−Gd). The series circuit of the mesa portion is composed of an inductor Lm and a resistance Rm.

In the present embodiment, admittance Y of the whole equivalent circuit also including the antenna system of the THz oscillation device 38 applied to the solution testing equipment 30 according to the first embodiment is expressed with the following equation:

$$Y=Yd+Yc\cdot Ya\cdot Ym/(Yc\cdot Ya+Ya\cdot Ym+Yc\cdot Ym),$$

where Yd=−Gd+jωCd, Yc=1/Rc+jωCc, Ym=1/(Rm+jωLm), Ya denotes the admittance of the antenna system, and ω denotes angular oscillation frequency. Each parameter can be calculated from a physical property value of the diode (RTD) composing the active element 90. Moreover, an oscillation frequency and an oscillation output are obtained by solving oscillating conditions Re(Y)<=0 and Im(Y)=0.

Figure 21A:
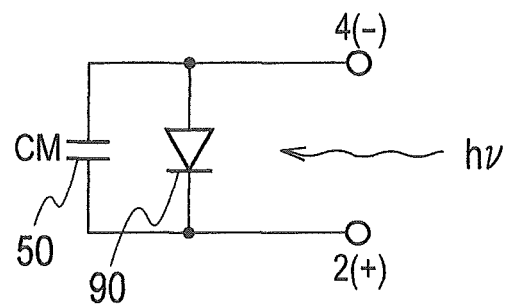
FIG. 21A is a schematic circuit configuration diagram of a THz detection device applied to the solution testing equipment according to the first embodiment.

A schematic circuit configuration of the THz detection device 44 applied to the solution testing equipment 30 according to the first embodiment is illustrated with a parallel circuit composed of the RTD composing the active element 90, and a capacitor CM composing the MIM reflector 50, as shown in FIG. 21A. The anode of the RTD is connected to the first electrode 4, and the cathode of the RTD is connected to the second electrode 2. Accordingly, the positive voltage is applied to the first electrode 4, and the negative voltage is applied to the second electrode 2. In the detecting state, an electromagnetic wave (hv) from the Y axial direction which is the aperture direction of the horn apertural area is detected with sufficient directivity.

The RTD composing the active element 90 can be indicated with a parallel circuit composed of a capacitor C01 and an inductor L01, and the capacitor CM of the MIM reflector 50 is further connected thereto in parallel.

Figure 22:
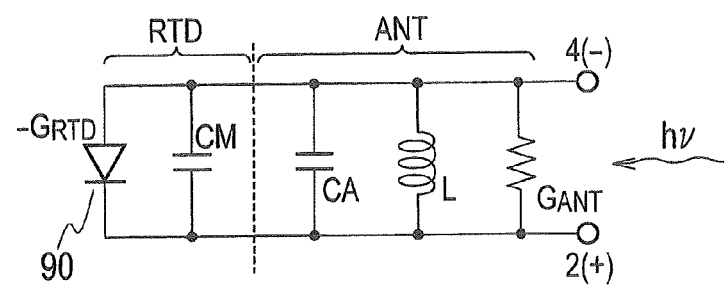
FIG. 22 is a schematic equivalent circuit configuration diagram also including the antenna system of the THz detection device applied to the solution testing equipment according to the first embodiment.

In a schematic equivalent circuit structure also including an antenna system of the THz detection device 44 applied to the solution testing equipment 30 according to the first embodiment, as shown in FIG. 22, a parallel circuit composed of an antenna inductor L, an antenna capacitor CA, and an antenna radiation resistance $G_{ANT}$ indicating an antenna (ANT) system is connected in parallel to the parallel circuit composed of the active element 90 and the capacitor CM indicating a diode (RTD) system.

An equivalent circuit structure of the RTD composing the active element 90 shown in FIG. 22 is similarly illustrated as that of FIG. 20B.

Figure 23:
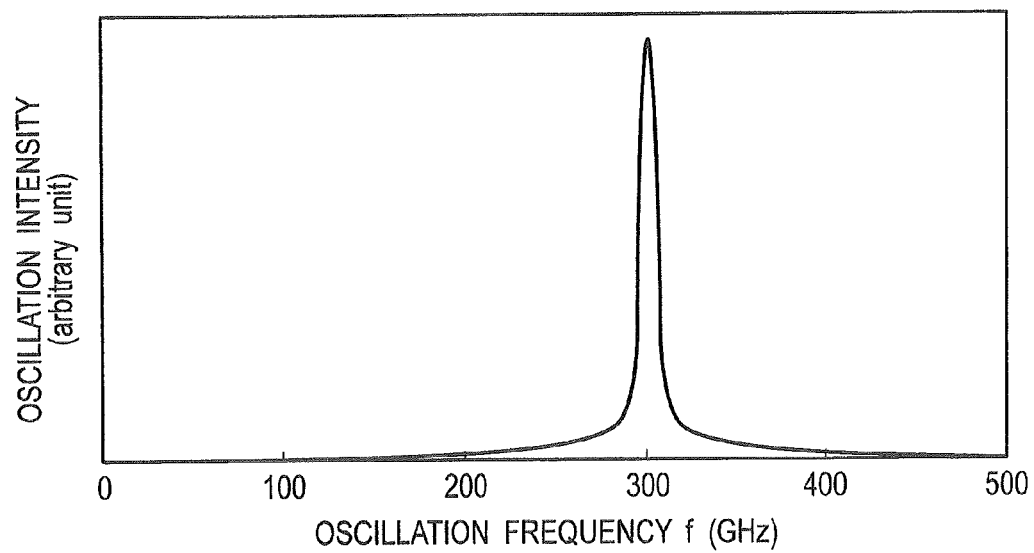
FIG. 23 is a diagram showing an example of a relationship between oscillation intensity and oscillation frequency f in an operation of the THz oscillation device applied to the solution testing equipment related to a first embodiment.

FIG. 23 illustrates an example of a relationship between the oscillation intensity and the oscillation frequency f, in the THz oscillation device 38 applied to the solution testing equipment 30 according to the first embodiment. The oscillation frequency f of approximately 300 GHz is achieved at room temperature. The value of the oscillation frequency f can be changed by adjusting the structure of each layer, the size of the mesa region, and/or the antenna structure, etc., shown in FIG. 18.

(Simulation Result of Radiation Pattern)

The solution 12 contacted thereto is water in a simulation. The relative permittivity ∈ of the water is 79.87 (20 degrees C.).

Figure 24A:
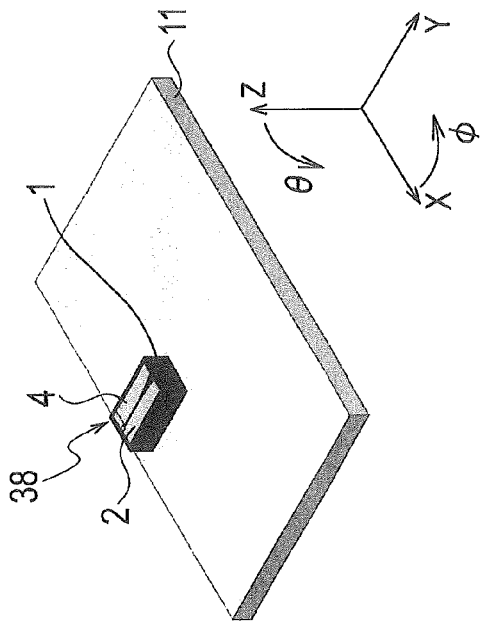
FIG. 24A is a schematic bird's-eye view structure diagram of a THz oscillation device applied to the solution testing equipment according to the first embodiment in the case of not forming an overlay insulating film on the surface thereof.
Figure 24B:
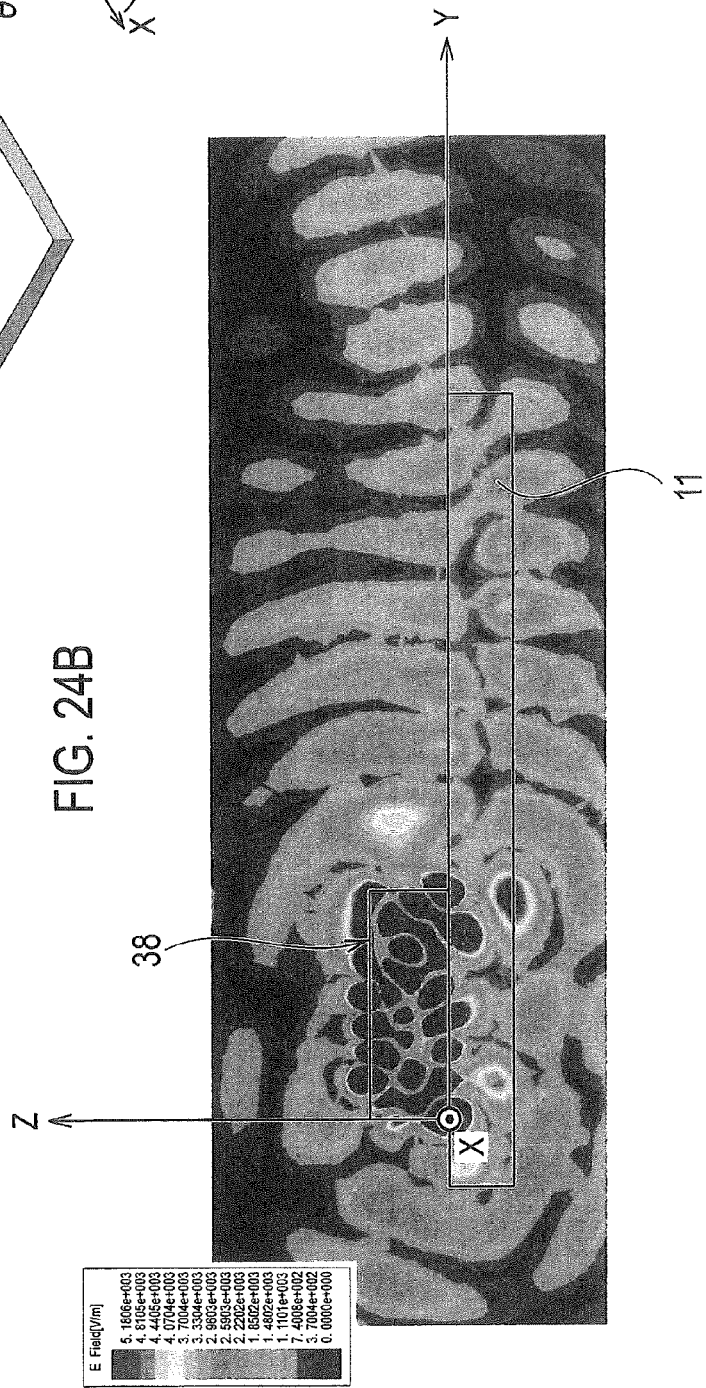
FIG. 24B shows a simulation result of a field emission pattern on the Y-Z plane in the case of radiating a THz wave from the THz oscillation device shown in FIG. 24A.

FIG. 24A illustrates a schematic bird's-eye view structure of the THz oscillation device 38 applied to the solution testing equipment 30 according to the first embodiment in the case of not providing the overlay insulating film 18 on the surface thereof. FIG. 24B illustrates a simulation result of a field emission pattern on the Y-Z plane in the case of radiating the THz wave from the THz oscillation device 38 shown in FIG. 24A.

As shown in FIG. 24B, the THz wave radiated from the THz oscillation device 38 comparatively strongly propagates particularly in the Y direction through the insulator substrate 11.

Figure 25A:
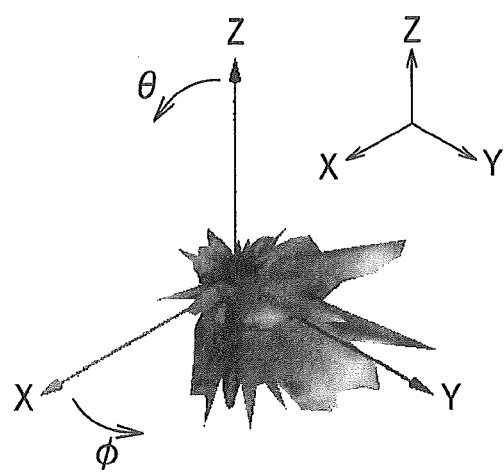
FIG. 25A shows a three-dimensional radiation pattern diagram on the X-Y-Z plane, in the electromagnetic field simulation result in the case of radiating the THz wave (hv) from the THz oscillation device shown in FIG. 24A.
Figure 25B:
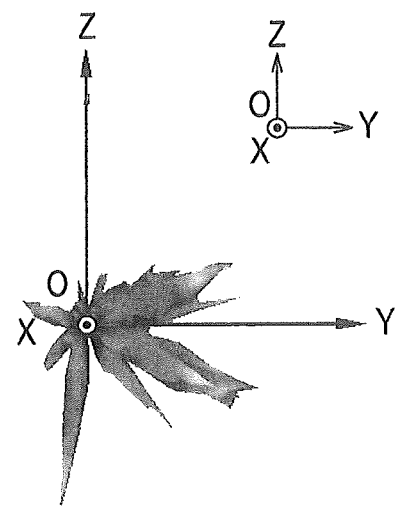
FIG. 25B shows a two-dimensional radiation pattern diagram on the X-Z plane, in the electromagnetic field simulation result in the case of radiating the THz wave (hv) from the THz oscillation device shown in FIG. 24A.
Figure 25C:
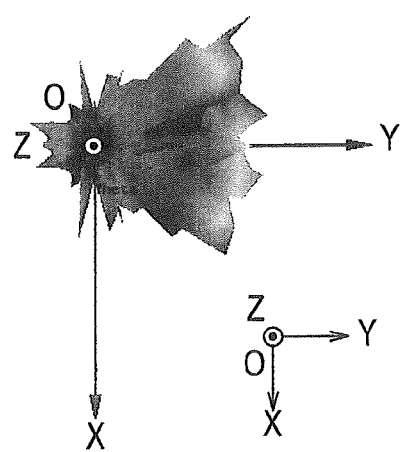
FIG. 25C shows a two-dimensional radiation pattern diagram on the X-Y plane, in the electromagnetic field simulation result in the case of radiating the THz wave (hv) from the THz oscillation device shown in FIG. 24A.
Figure 25D:
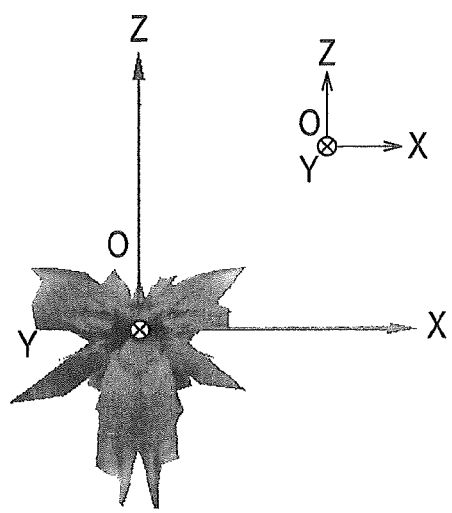
FIG. 25D shows a two-dimensional radiation pattern diagram on the X-Z plane, in the electromagnetic field simulation result in the case of radiating the THz wave (hv) from the THz oscillation device shown in FIG. 24A.

In an electromagnetic field simulation result in the case of radiating the THz wave from the THz oscillation device 38 shown in FIG. 24A, FIG. 25A illustrates a three-dimensional radiation pattern on the X-Y-Z plane, FIG. 25B illustrates a two-dimensional radiation pattern on the Y-Z plane, FIG. 25C illustrates a two-dimensional radiation pattern on the X-Y plane, and FIG. 25D illustrates a two-dimensional radiation pattern on the X-Z plane.

According to the radiation patterns shown in FIGS. 25A, 25B, 25C and 25D, the THz wave (hv) is comparatively strongly radiated in the Y direction.

Figure 26A:
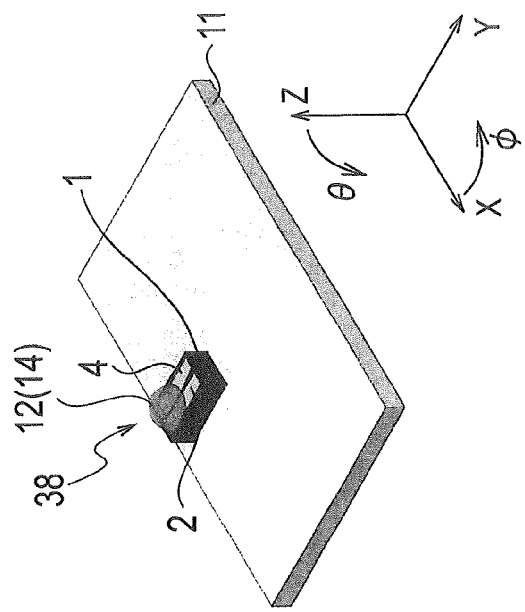
FIG. 26A is a schematic bird's-eye view structure diagram showing a state where water is contacted with the THz oscillation device applied to the solution testing equipment according to the first embodiment in the case of not forming an overlay insulating film on the surface thereof.
Figure 26B:
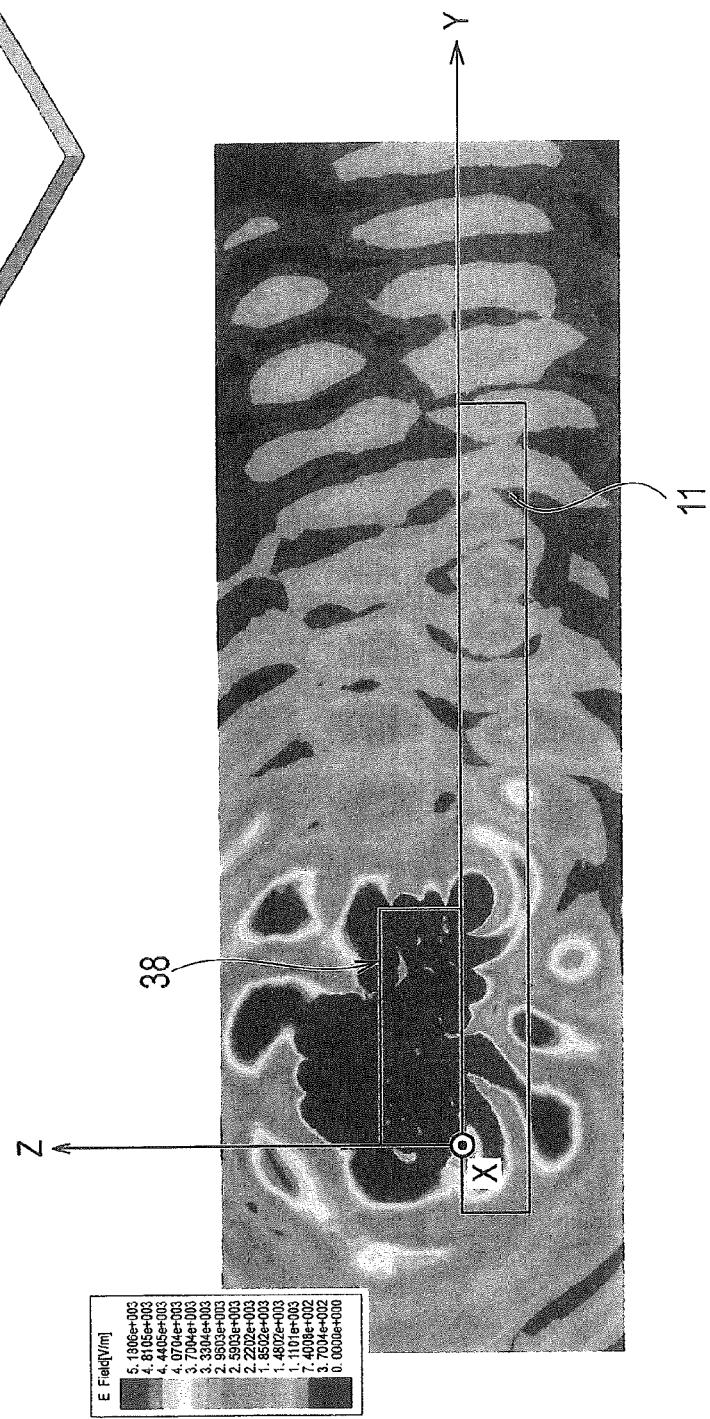
FIG. 26B shows a simulation result of a field emission pattern on the Y-Z plane in the case of testing water with the THz oscillation device shown in FIG. 26A.

FIG. 26A illustrates a schematic bird's-eye view structure showing a state where water 12 is contacted with the THz oscillation device 38 applied to the solution testing equipment 30 according to the first embodiment in the case of not forming the overlay insulating film 18 on the surface thereof. FIG. 26B illustrates a simulation result of a field emission pattern on the Y-Z plane in the case of testing the water 12 with the THz oscillation device 38 shown in FIG. 26A. In the present embodiment, the diameter of the waterdrop is approximately 1 mm. The thickness of the InP substrate (semiconductor substrate 1) is 600 μm, and the thickness of the Teflon (registered trademark) substrate 11 is 500 μm.

As shown in FIG. 26B, the THz wave (hv) radiated from the THz oscillation device 38 comparatively strongly propagates particularly in the Y direction through the insulator substrate 11, and the THz wave is radiated more strongly as compared with the simulation result of FIG. 24B.

Figure 27A:
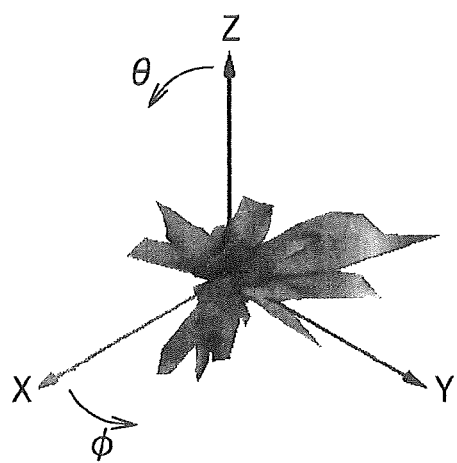
FIG. 27A is a three-dimensional radiation pattern diagram on the X-Y-Z plane, in the electromagnetic field simulation result in the case of testing the water with the THz oscillation device shown in FIG. 26A.
Figure 27B:
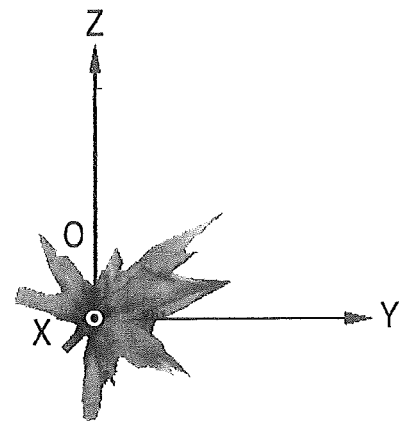
FIG. 27B is a two-dimensional radiation pattern diagram on the Y-Z plane, in the electromagnetic field simulation result in the case of testing the water with the THz oscillation device shown in FIG. 26A.
Figure 27C:
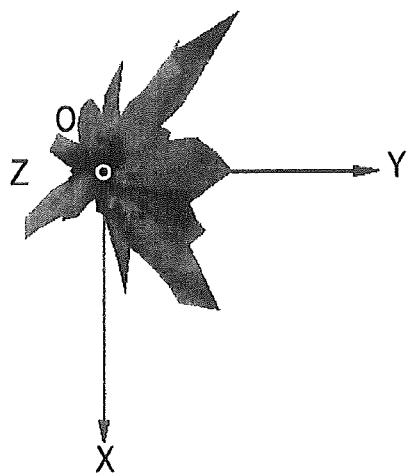
FIG. 27C is a two-dimensional radiation pattern diagram on the X-Y plane, in the electromagnetic field simulation result in the case of testing the water with the THz oscillation device shown in FIG. 26A.
Figure 27D:
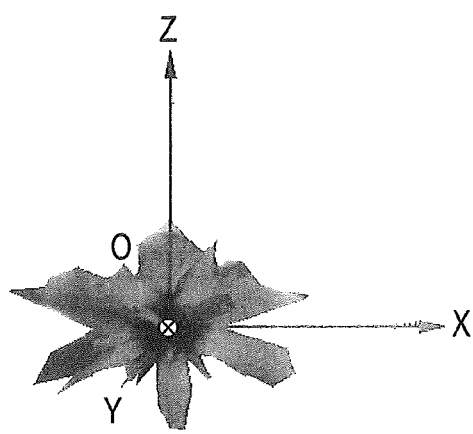
FIG. 27D is a two-dimensional radiation pattern diagram on the X-X plane, in the electromagnetic field simulation result in the case of testing the water with the THz oscillation device shown in FIG. 26A.

In an electromagnetic field simulation result in the case of testing the water with the THz oscillation device 38 shown in FIG. 26A, FIG. 27A illustrates a three-dimensional radiation pattern on an X-Y-Z plane, FIG. 27B illustrates a two-dimensional radiation pattern on the Y-Z plane, FIG. 27C illustrates a two-dimensional radiation pattern on the X-Y plane, and FIG. 27D illustrates a two-dimensional radiation pattern on the X-Z plane.

According to the radiation patterns shown in FIGS. 27A, 27B, 27C and 27D, the THz wave is comparatively strongly radiated in the Y direction.

Then, the field emission pattern shown in FIG. 26B and the electromagnetic field radiation patterns shown in FIGS. 27A, 27B, 27C and 27D are obtained previously, and the radiation pattern of the solution is matched (pattern matching) with the field emission patterns or the electromagnetic field radiation patterns obtained from the solution testing equipment 30 according to the first embodiment, thereby determining that the test object is "water", for example.

More specifically, according to the solution testing equipment 30 according to the first embodiment, the field emission patterns and the electromagnetic field radiation patterns determined in response to the relative permittivity ∈ are output, in which the relative permittivity ∈ varies in accordance with the test object. Accordingly, it becomes possible to identify the kind of the solution as the test object by matching (pattern matching) the radiation pattern of the solution with the previously obtained field emission patterns stored in a storage device.

(Simulation Result)

FIG. 28A illustrates a schematic bird's-eye view structure of the THz oscillation device 38 applied to the solution testing equipment 30 according to the first embodiment in the case of forming a 0.6-micrometer-thick overlay insulating film ($SiO_2$ film) 18 on the surface thereof. FIG. 28B illustrates a simulation result of a field emission pattern on the Y-Z plane in the case of radiating the THz wave from the THz oscillation device 38 shown in FIG. 28A.

Figure 29A:
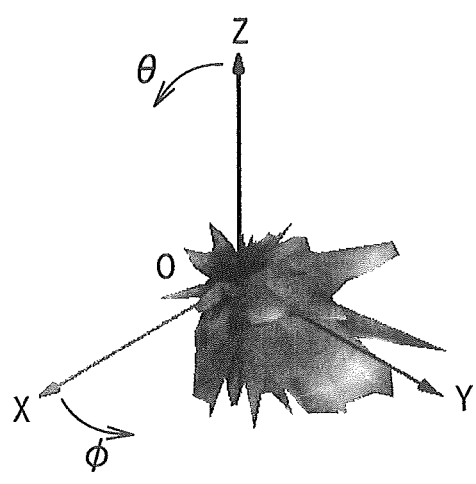
FIG. 29A shows a three-dimensional radiation pattern diagram on the X-Y-Z plane, in the electromagnetic field simulation result in the case of radiating the THz wave (hv) from the THz oscillation device shown in FIG. 28A.
Figure 29B:
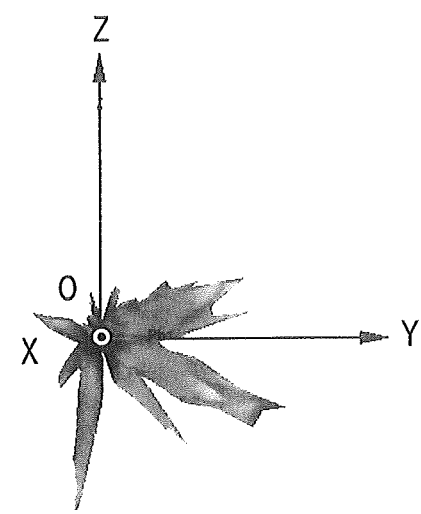
FIG. 29B shows a two-dimensional radiation pattern diagram on the X-Z plane, in the electromagnetic field simulation result in the case of radiating the THz wave (hv) from the THz oscillation device shown in FIG. 28A.
Figure 29C:
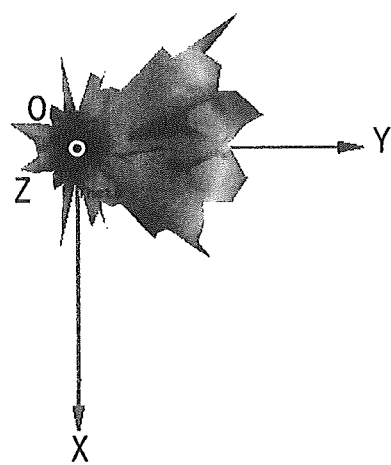
FIG. 29C shows a two-dimensional radiation pattern diagram on the X-Y plane, in the electromagnetic field simulation result in the case of radiating the THz wave (hv) from the THz oscillation device shown in FIG. 28A.
Figure 29D:
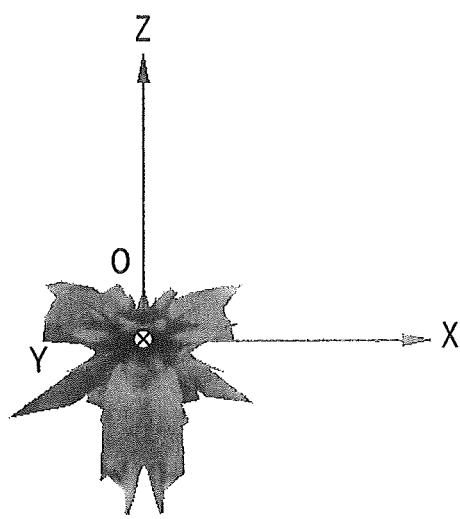
FIG. 29D shows a two-dimensional radiation pattern diagram on the X-Z plane, in the electromagnetic field simulation result in the case of radiating the THz wave (hv) from the THz oscillation device shown in FIG. 28A.

In an electromagnetic field simulation result in the case of radiating the THz wave from the THz oscillation device 38 shown in FIG. 28A, FIG. 29A illustrates a three-dimensional radiation pattern on the X-Y-Z plane, FIG. 29B illustrates a two-dimensional radiation pattern on the Y-Z plane, FIG. 29C illustrates a two-dimensional radiation pattern on the X-Y plane, and FIG. 29D illustrates a two-dimensional radiation pattern on the X-Z plane.

As shown in FIG. 28B, the THz wave radiated from the THz oscillation device 38 comparatively strongly propagates particularly in the Y direction through the insulator substrate 11.

As compared with the simulation result of FIG. 24B in the case of not providing the $SiO_2$ film, the radiation pattern shown in FIG. 28B is substantially equivalent thereto.

According to the radiation patterns shown in FIGS. 29A, 29B, 29C and 29D, the THz wave is comparatively strongly radiated in the Y direction. As compared with the electromagnetic field simulation result of FIGS. 25A, 25B, 25C and 25D in the case of not providing the $SiO_2$ film, the radiation patterns shown in FIGS. 29A, 29B, 29C and 29D are substantially equivalent thereto.

Figure 30A:
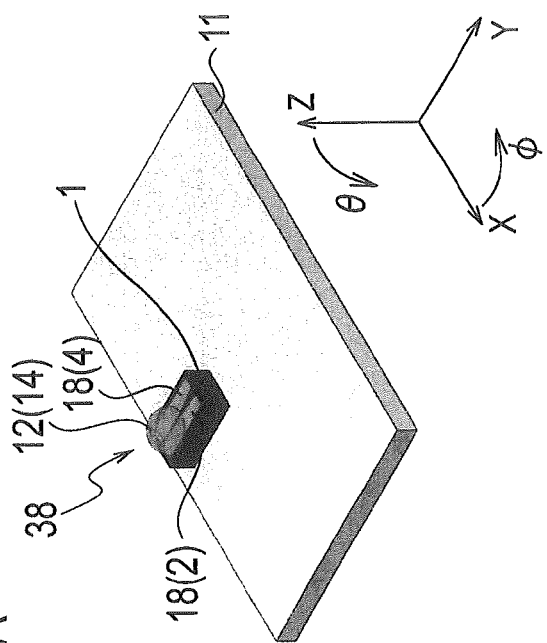
FIG. 30A is a schematic bird's-eye view structure diagram showing a state where the water is contacted with the THz oscillation device applied to the solution testing equipment according to the first embodiment in the case of forming a 0.6-µm-thick overlay insulating film ($SiO_2$ film) on the surface thereof.
Figure 30B:
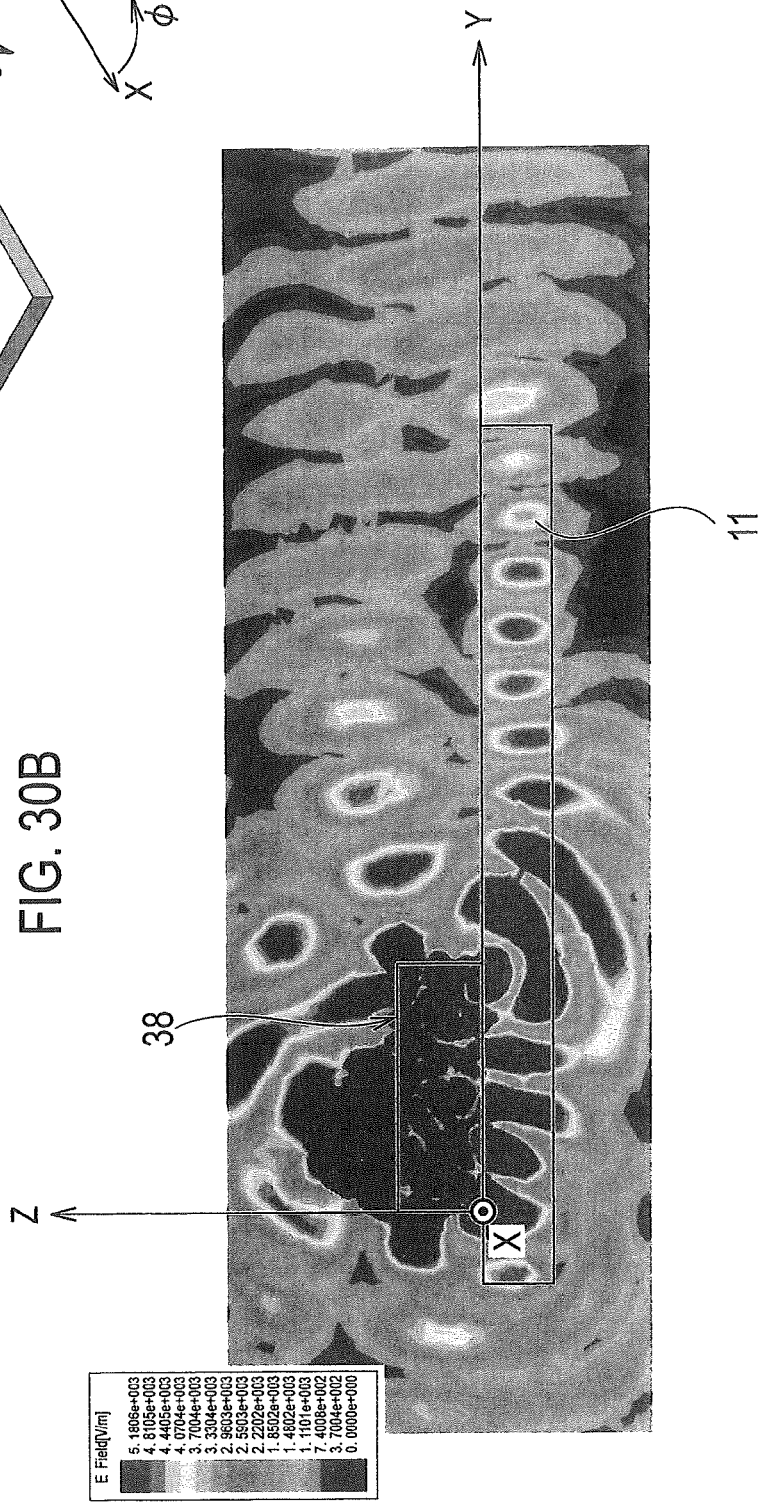
FIG. 30B shows a simulation result of a field emission pattern on the Y-Z plane in the case of testing the water with the THz oscillation device shown in FIG. 30A.

FIG. 30A illustrates a schematic bird's-eye view structure showing a state where the water is contacted with the THz oscillation device 38 applied to the solution testing equipment 30 according to the first embodiment in the case of forming a 0.6-μm-thick overlay insulating film ($SiO_2$ film) on the surface thereof. FIG. 30B illustrates a simulation result of a field emission pattern on the Y-Z plane in the case of testing the water with the THz oscillation device 38 shown in FIG. 30A.

As shown in FIG. 30B, the THz wave (hv) radiated from the THz oscillation device 38 comparatively strongly propagates particularly in the Y direction through the insulator substrate 11.

As compared with the simulation result of FIG. 26B in the case of not providing the $SiO_2$ film, the THz wave propagates more strongly.

Figure 31A:
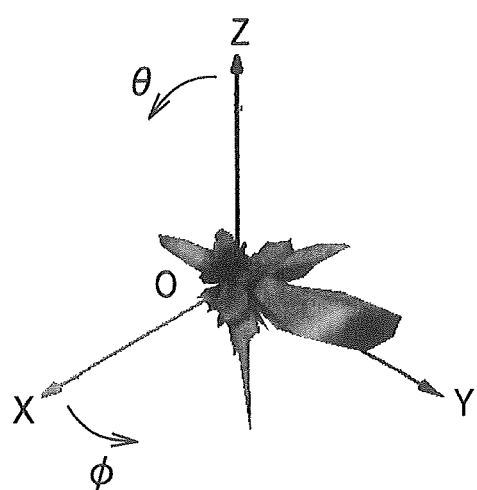
FIG. 31A is a three-dimensional radiation pattern diagram on the X-Y-Z plane, in the electromagnetic field simulation result in the case of testing the water with the THz oscillation device shown in FIG. 30A.
Figure 31B:
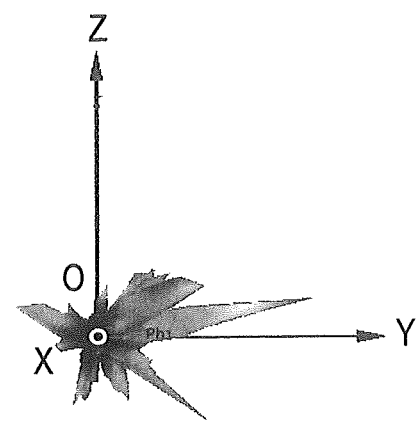
FIG. 31B is a two-dimensional radiation pattern diagram on the Y-Z plane, in the electromagnetic field simulation result in the case of testing the water with the THz oscillation device shown in FIG. 30A.
Figure 31C:
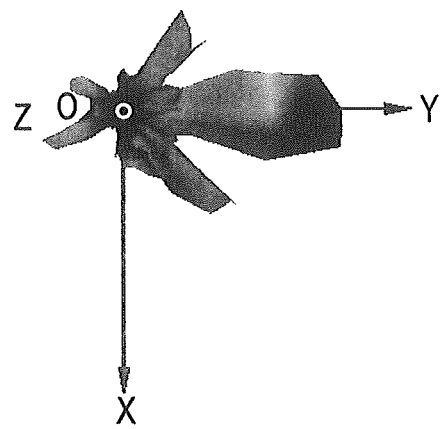
FIG. 31C is a two-dimensional radiation pattern diagram on the X-Y plane, in the electromagnetic field simulation result in the case of testing the water with the THz oscillation device shown in FIG. 30A.
Figure 31D:
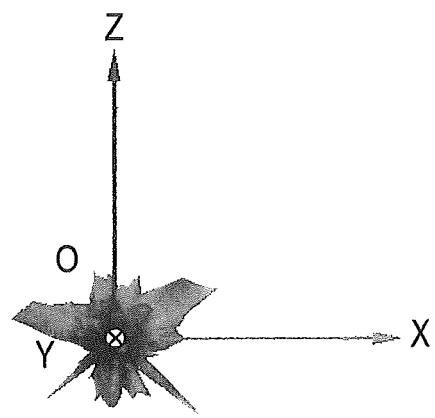
FIG. 31D is a two-dimensional radiation pattern diagram on the X-X plane, in the electromagnetic field simulation result in the case of testing the water with the THz oscillation device shown in FIG. 30A.

In an electromagnetic field simulation result in the case of testing the water with the THz oscillation device 38 shown in FIG. 30A, FIG. 21A illustrates a three-dimensional radiation pattern on an X-Y-Z plane, FIG. 31B illustrates a two-dimensional radiation pattern on the Y-Z plane, FIG. 31C illustrates a two-dimensional radiation pattern on the X-Y plane, and FIG. 31D illustrates a two-dimensional radiation pattern on the X-Z plane.

As shown in FIGS. 31A, 31B, 31C and 31D, the THz wave is comparatively strongly radiated in the Y direction. The radiation pattern varies more greatly, as compared with the electromagnetic field simulation result of FIGS. 25A, 25B, 25C and 25D in the state where the water 12 is not contacted therewith.

The variation of the radiation patterns in the case of providing the 0.6-μm-thick $SiO_2$ film 18 on the surface thereof (FIGS. 29 and 31) is more greatly, as compared with the variations of the radiation patterns in the case of not providing the overlay insulating film in the surface thereof (FIGS. 25 and 27).

Thus, since the variation patterns of the THz wave corresponding to the existence or nonexistence of the solution to be contacted therewith are more apparent in the case of providing such a 0.6-μm-thick $SiO_2$ film on the surface thereof, it becomes possible to grasp the test result more definitely, thereby improving the testing accuracy.

Figure 32:
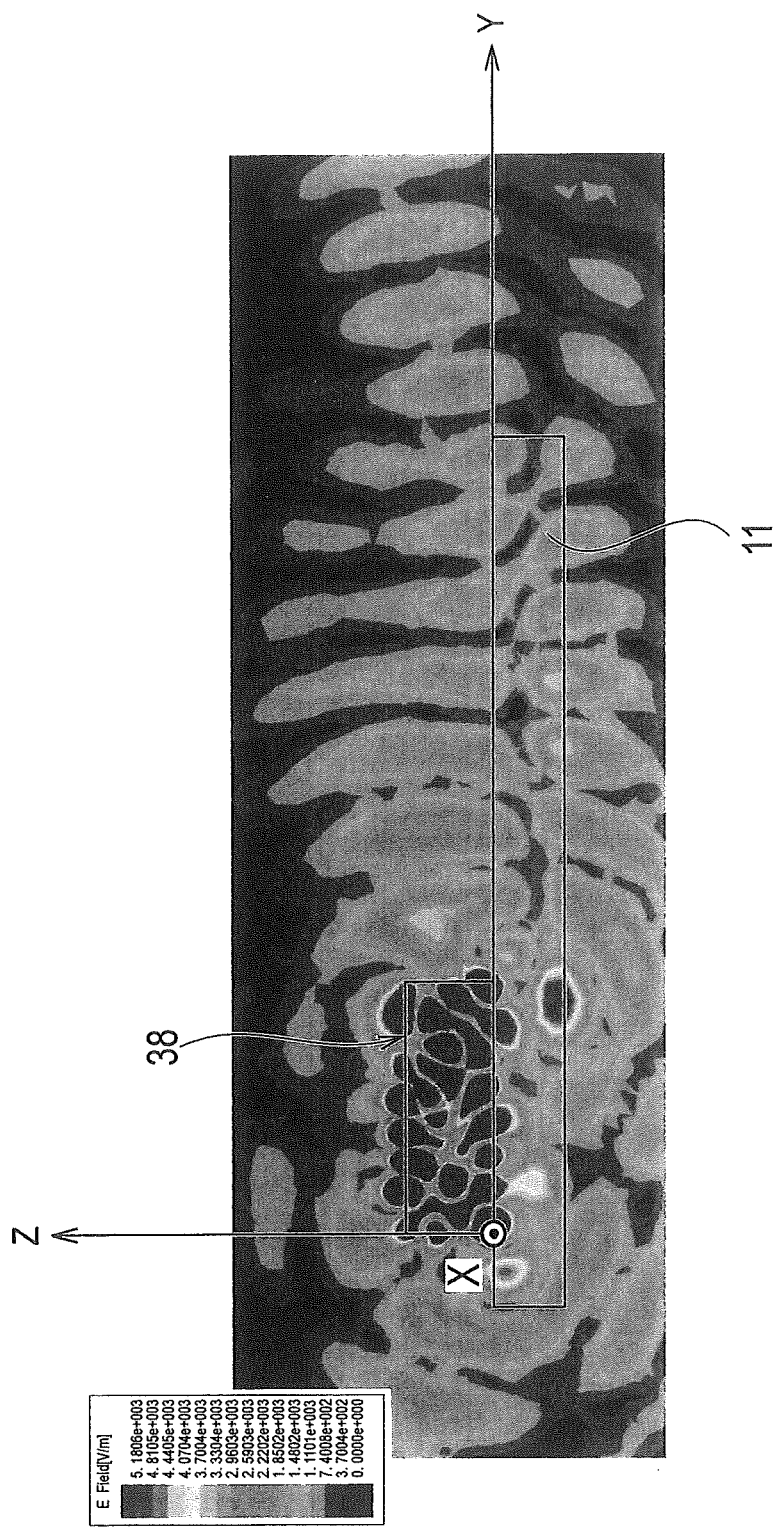
FIG. 32 shows a simulation result of a field emission pattern on the Y-Z plane in the case of radiating the THz wave (hv) from the THz oscillation device applied to the solution testing equipment according to the first embodiment, in the case of forming a 5-µm-thick overlay insulating film ($SiO_2$ film) on the surface thereof.

FIG. 32 illustrates a simulation result of a field emission pattern on the Y-Z plane in the case of radiating the THz wave (hv) from the THz oscillation device 38 applied to the solution testing equipment 30 according to the first embodiment, in the case of forming a 5-μm-thick overlay insulating film ($SiO_2$ film) on the surface thereof.

As shown in FIG. 32, the THz wave radiated from the THz oscillation device 38 comparatively strongly propagates particularly in the Y direction through the insulator substrate 11.

Figure 21B:
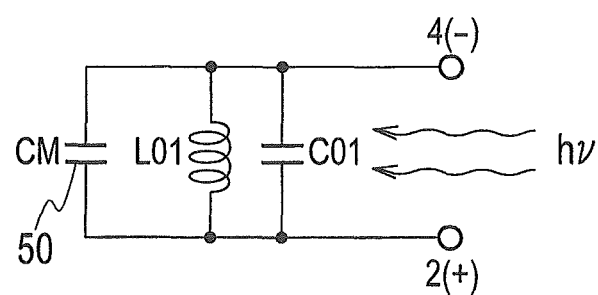
FIG. 21B is a simplified equivalent circuit configuration diagram of the THz detection device applied to the solution testing equipment according to the first embodiment.
Figure 33A:
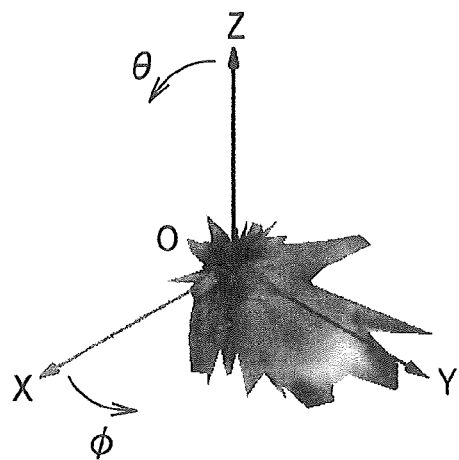
FIG. 33A shows a three-dimensional radiation pattern diagram on the X-Y-Z plane, in the electromagnetic field simulation result in the case of radiating the THz wave from the THz oscillation device shown in FIG. 32.
Figure 33B:
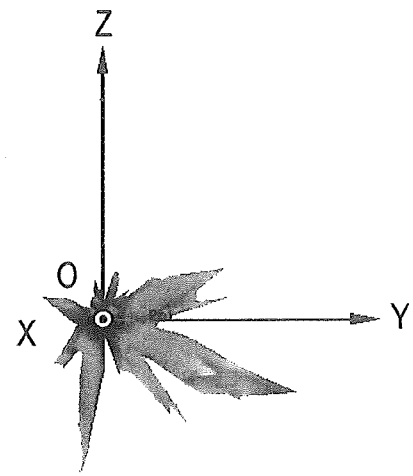
FIG. 33B shows a two-dimensional radiation pattern diagram on the X-Z plane, in the electromagnetic field simulation result in the case of radiating the THz wave from the THz oscillation device shown in FIG. 32.
Figure 33C:
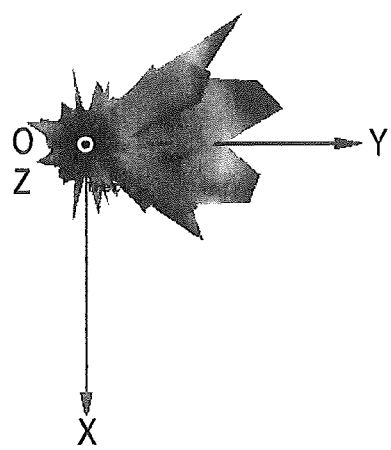
FIG. 33C shows a two-dimensional radiation pattern diagram on the X-Y plane, in the electromagnetic field simulation result in the case of radiating the THz wave from the THz oscillation device shown in FIG. 32.
Figure 33D:
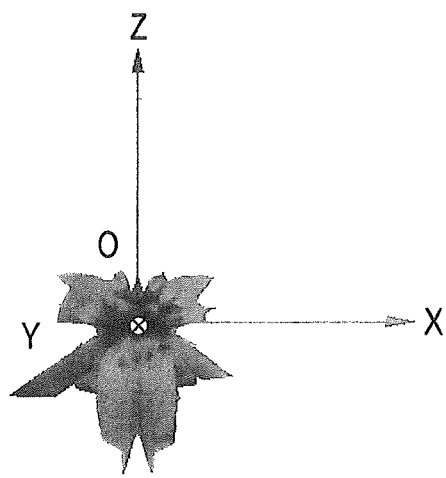
FIG. 33D shows a two-dimensional radiation pattern diagram on the X-Z plane, in the electromagnetic field simulation result in the case of radiating the THz wave from the THz oscillation device shown in FIG. 32.

In an electromagnetic field simulation result in the case of radiating the THz wave from the THz oscillation device 38 shown in FIG. 21, FIG. 33A illustrates a three-dimensional radiation pattern on the X-Y-Z plane, FIG. 33B illustrates a two-dimensional radiation pattern on the Y-Z plane, FIG. 33C illustrates a two-dimensional radiation pattern on the X-Y plane, and FIG. 33D illustrates a two-dimensional radiation pattern on the X-Z plane.

According to the radiation patterns shown in FIGS. 33A, 33B, 33C and 33D, the THz wave (hv) is comparatively strongly radiated particularly in the Y direction.

Figure 34:
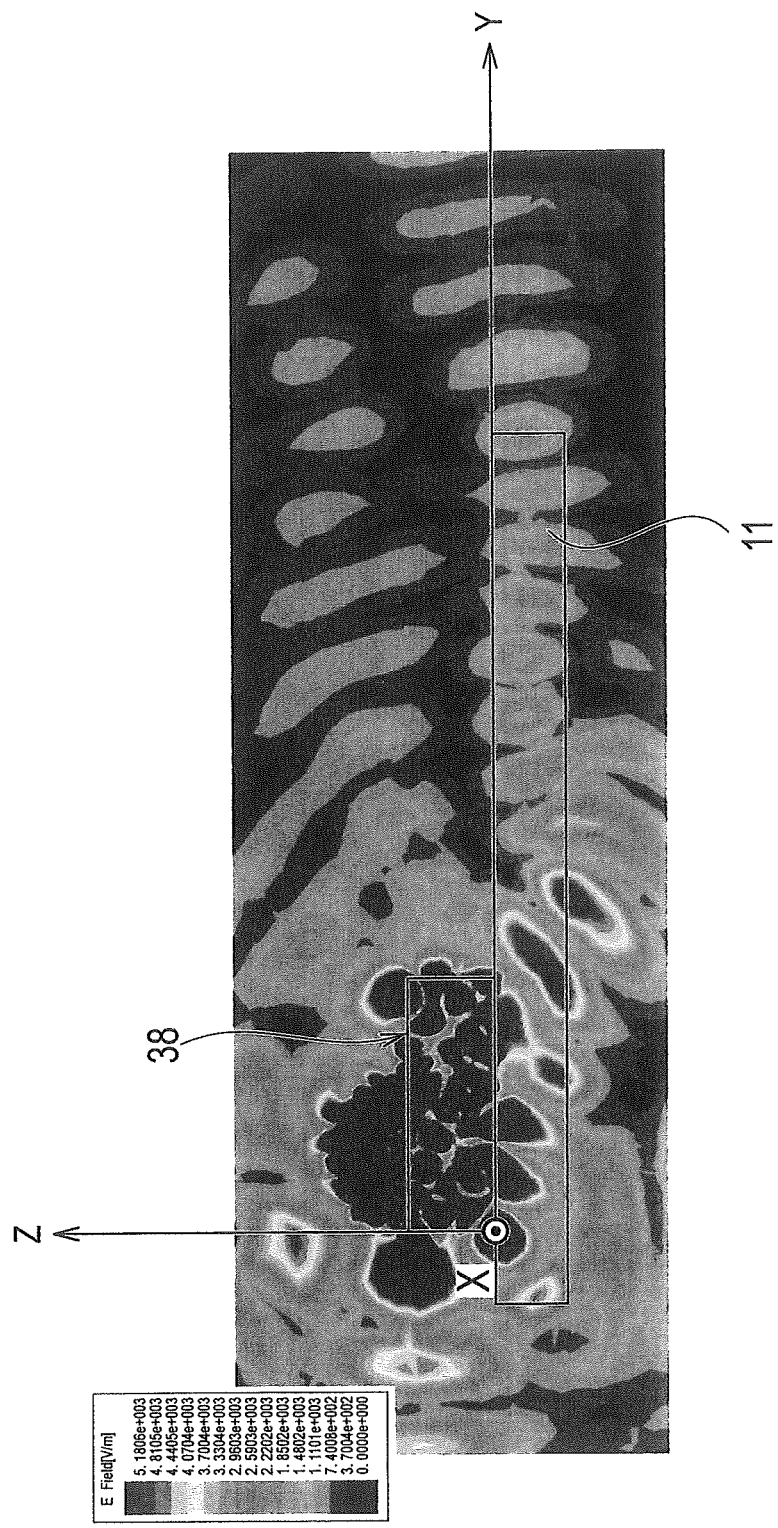
FIG. 34 shows a simulation result of a field emission pattern on the Y-Z plane in the case of testing the water with the THz oscillation device applied to the solution testing equipment according to the first embodiment, in the case of forming a 5-µm-thick overlay insulating film ($SiO_2$ film) on the surface thereof.

FIG. 34 illustrates a simulation result of a field emission pattern on the Y-Z plane in the case of testing the water 12 with the THz oscillation device 38 applied to the solution testing equipment 30 according to the first embodiment, in the case of forming a 5-μm-thick overlay insulating film ($SiO_2$ film) on the surface thereof.

As shown in FIG. 34, the THz wave radiated from the THz oscillation device 38 comparatively strongly propagates particularly in the Y direction through the insulator substrate 11.

The field emission pattern shown in FIG. 34 varies more greatly, as compared with the simulation result (FIG. 32) of the field emission pattern in the state where the water 12 as a test object is not contacted therewith.

Figure 35A:
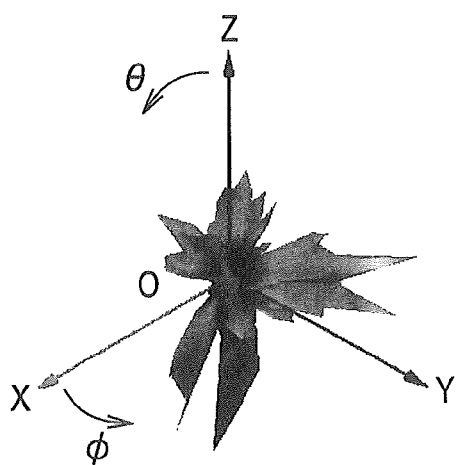
FIG. 35A is a three-dimensional radiation pattern diagram on the X-Y-Z plane, in the electromagnetic field simulation result in the case of testing the water with the THz oscillation device shown in FIG. 34.
Figure 35B:
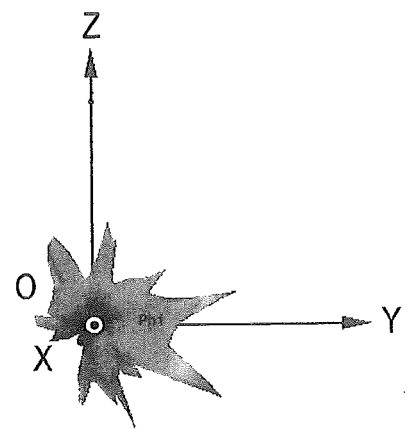
FIG. 35B is a two-dimensional radiation pattern diagram on the Y-Z plane, in the electromagnetic field simulation result in the case of testing the water with the THz oscillation device shown in FIG. 34.
Figure 35C:
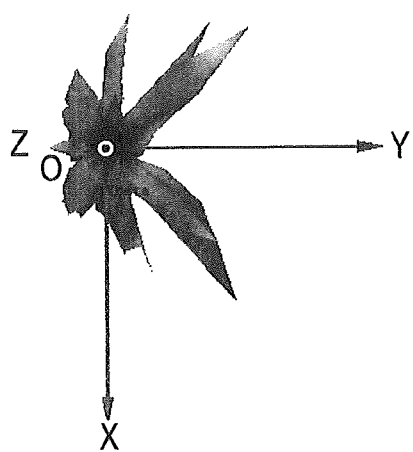
FIG. 35C is a two-dimensional radiation pattern diagram on the X-Y plane, in the electromagnetic field simulation result in the case of testing the water with the THz oscillation device shown in FIG. 34.
Figure 35D:
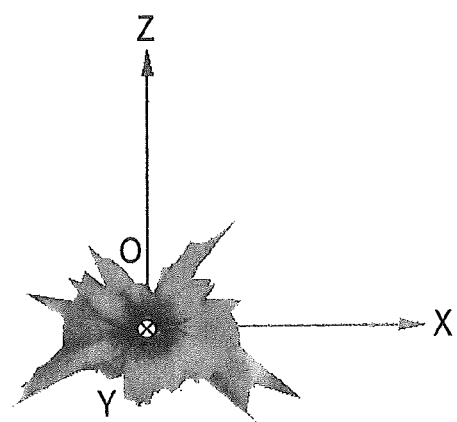
FIG. 35D is a two-dimensional radiation pattern diagram on the X-Z plane, in the electromagnetic field simulation result in the case of testing the water with the THz oscillation device shown in FIG. 34.

In an electromagnetic field simulation result in the case of testing the water 12 with the THz oscillation device 38 shown in FIG. 34A, FIG. 35A illustrates a three-dimensional radiation pattern on an X-Y-Z plane, FIG. 35B illustrates a two-dimensional radiation pattern on the Y-Z plane, FIG. 35C illustrates a two-dimensional radiation pattern on the X-Y plane, and FIG. 35D illustrates a two-dimensional radiation pattern on the X-Z plane.

As shown in FIGS. 35A, 35B, 35C and 35D, the THz wave (hv) is comparatively strongly radiated in the Y direction.

The radiation patterns shown in FIG. 35 vary more greatly, as compared with the electromagnetic field simulation result of FIGS. 33A, 33B, 33C and 33D in the state where the water 12 is not contacted therewith.

The variation of the radiation patterns in the case of providing the 5-μm-thick SiO₂ film 18 on the surface thereof (FIGS. 33 and 35) is more greatly, as compared with the variations of the radiation patterns in the case of not providing the 0.6-μm-thick SiO₂ film 18 in the surface thereof (FIGS. 29 and 31).

Thus, since the variation patterns of the THz wave corresponding to the existence or nonexistence of the solution to be contacted therewith are more apparent in the case of providing such a 5-μm-thick SiO₂ film on the surface thereof, it becomes possible to grasp the test result more definitely, thereby further improving the testing accuracy.

To give further detailed explanation, in the THz oscillation device 38 applied to the solution testing equipment 30 according to the first embodiment, the maximum radiation directions are approximately equivalent to each other (e.g., θ=250 degrees, and φ=−110 degrees), and the emission ratios are also approximately equivalent to each other, in the state where the water 12 is not contacted therewith, regardless of the existence or nonexistence of the overlay insulating film 18, and regardless of the thickness of the overlay insulating film 18. On the other hand, in the state of the water 12 is contacted therewith, the radiation ratio in the maximum radiation direction is approximately 0.84, and the variation rate is approximately 16%, if the overlay insulating film 18 is not formed thereon. However, if the overlay insulating film 18 is formed thereon, the radiation ratio in the maximum radiation direction is approximately 0.31 (0.6 μm), and approximately 0.33 (5.0 μm), and the variation rate is greatly varied, i.e., approximately 70%.

(Variation of Antenna Characteristics)

Figure 36:
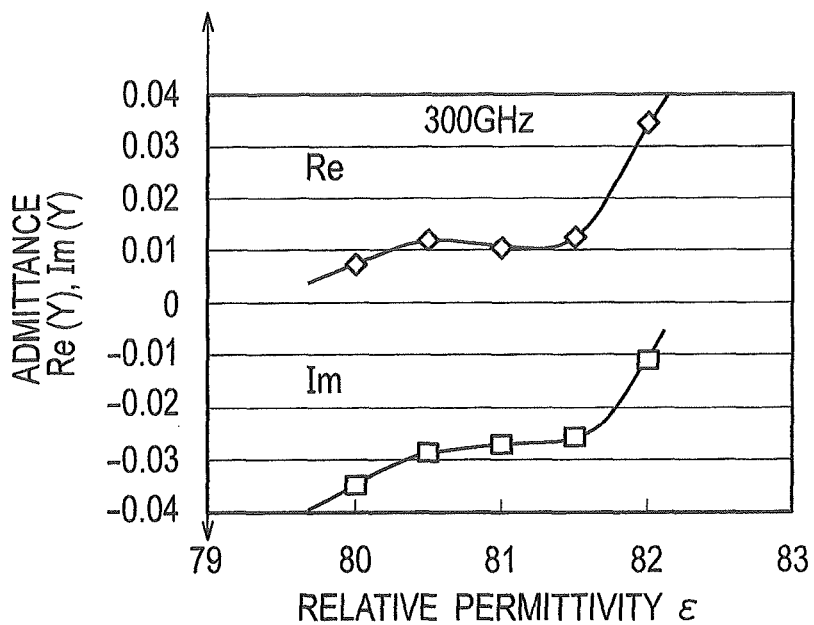
FIG. 36 shows a graphic chart showing a relationship between an admittance (Re (Y), IM (Y)) and a relative permittivity $\in$ at an operational frequency of 300 GHz, in the THz oscillation device applied to the solution testing equipment according to the first embodiment.

FIG. 36 illustrates a relationship between an admittance (Re (Y), IM (Y)) and a relative permittivity ∈ at an operational frequency of 300 GHz, in the THz oscillation device applied to the solution testing equipment according to the first embodiment.

Figure 37:
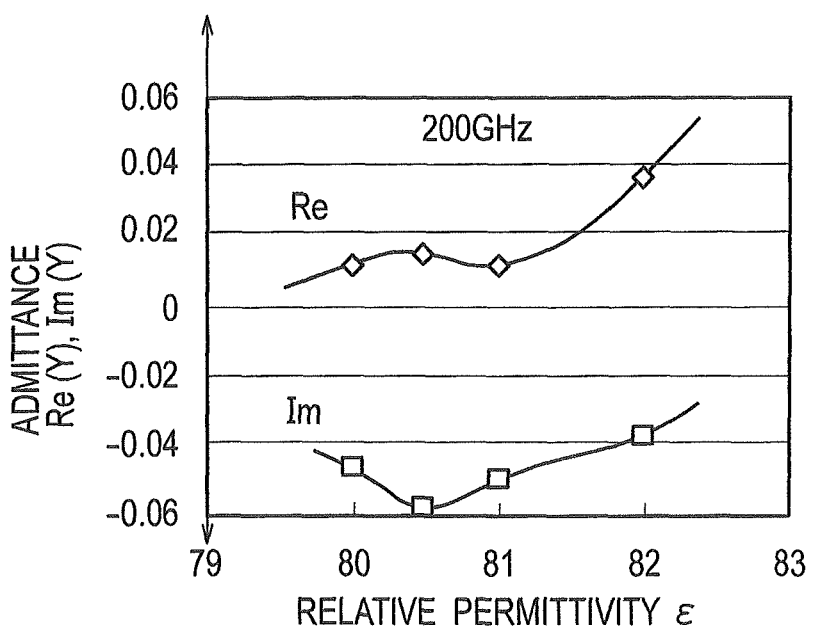
FIG. 37 shows a graphic chart showing a relationship between the admittance (Re (Y), IM (Y)) and the relative permittivity at an operational frequency of 200 GHz, in the THz oscillation device applied to the solution testing equipment according to the first embodiment.

Moreover, FIG. 37 illustrates a relationship between an admittance (Re (Y), IM (Y)) and a relative permittivity ∈ at an operational frequency of 200 GHz, in the THz oscillation device applied to the solution testing equipment according to the first embodiment.

Figure 38:
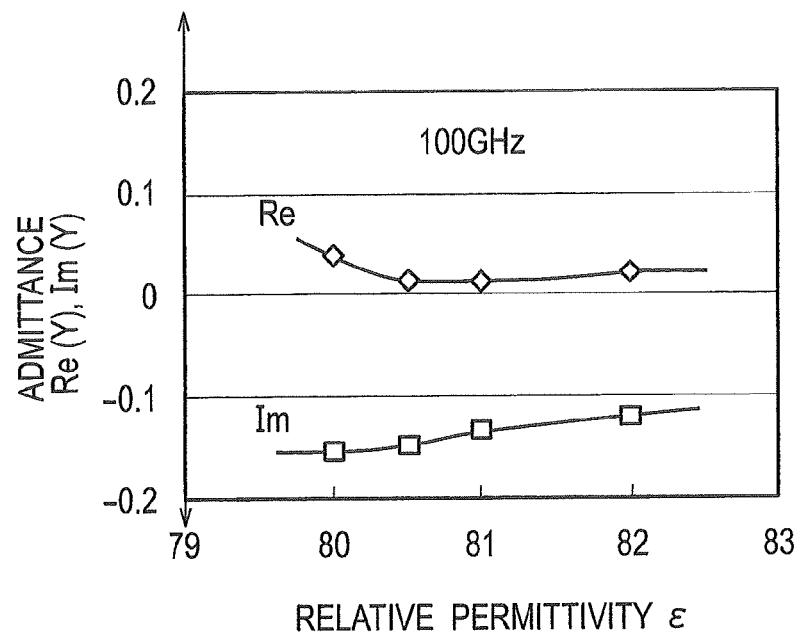
FIG. 38 shows a graphic chart showing a relationship between the admittance (Re (Y), IM (Y)) and the relative permittivity $\in$ at an operational frequency of 100 GHz, in the THz oscillation device applied to the solution testing equipment according to the first embodiment.

Moreover, FIG. 38 illustrates a relationship between an admittance (Re (Y), IM (Y)) and a relative permittivity ∈ at an operational frequency of 100 GHz, in the THz oscillation device applied to the solution testing equipment according to the first embodiment.

In FIGS. 36-38, the Re (Y) denotes the real part of the admittance Y, and the Im (Y) denotes the imaginary part of the admittance Y of the THz oscillation device. In the present embodiment, the unit of the real part Re (Y) of admittance Y, and the unit of the imaginary part Im (Y) are shown with an arbitrary unit.

As shown in FIG. 36, at the operational frequency of 300 GHz, there is a trend that the imaginary part Im (Y) and the real part Re (Y) of the admittance Y increase, as the relative permittivity ∈ becomes higher. In particular, the increase of the relative permittivity ∈ from around 81.5 is remarkable.

As shown in FIG. 37, at the operational frequency of 200 GHz, there is a trend that the real part Re (Y) of the admittance Y increases, as the relative permittivity ∈ becomes higher. In particular, the increase of the relative permittivity ∈ from around 81 is remarkable.

On the other hand, there is a trend that the imaginary part Im (Y) of the admittance Y once decreases at the relative permittivity ∈ around 80-81, but then increases after that.

As shown in FIG. 38, at the operational frequency of 100 GHz, there is a trend that the real part Re (Y) of admittance Y becomes approximately constant after gradually decreasing, as the relative permittivity ∈ becomes higher.

On the other hand, there is a trend that the imaginary part Im (Y) of the admittance gradually increases.

Thus, also at each operational frequency of 100, 200, 300 GHz, the admittance varies in response to the relative permittivity ∈ of the solution 12 to be tested, and the output characteristics vary in response to the relative permittivity ∈ of the solution 12.

Modified Example 1

Figure 39:
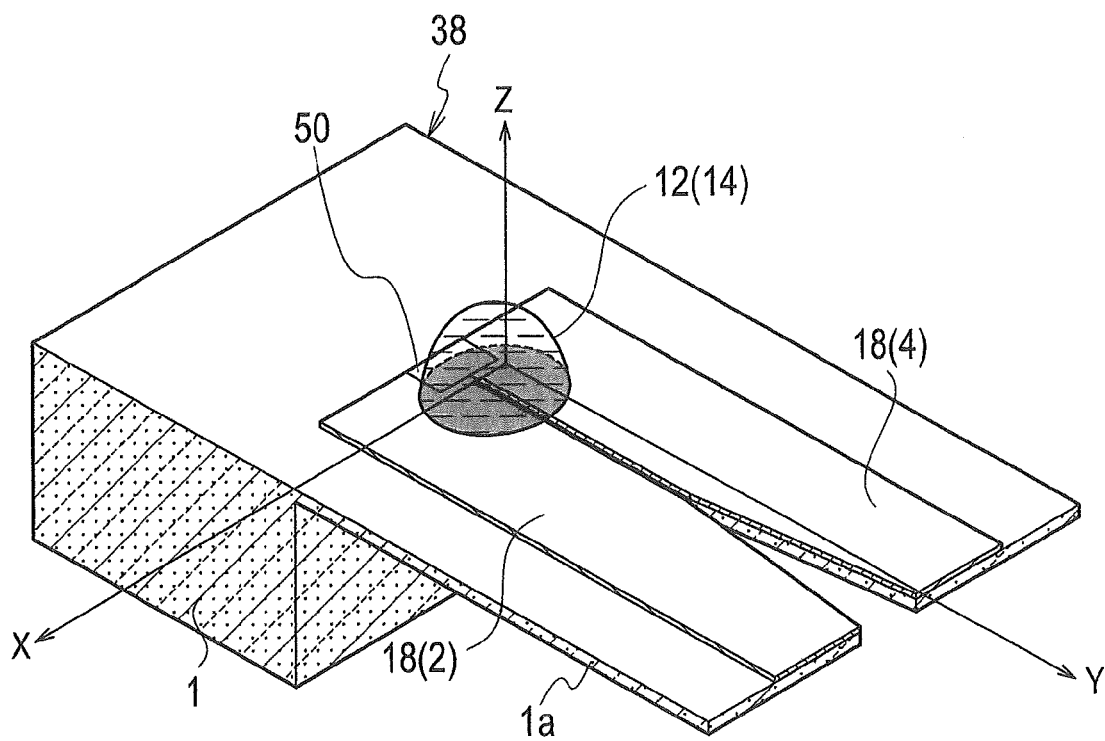
FIG. 39 is a schematic bird's-eye view of a THz oscillation device according to a modified example 1 applicable to the solution testing equipment according to the first embodiment.

FIG. 39 illustrates a schematic bird's-eye view structure of a modified example 1 of the THz oscillation device 38 applied to the solution testing equipment 30 according to the first embodiment.

In the modified example 1, as shown in FIG. 39, the semiconductor substrate 1 is thin-layered at the disposition region of the first electrode 4 and the second electrode 2 forming the resonator 60, the waveguide 70, and the horn apertural area 80. Furthermore, as shown in FIG. 39, the semiconductor substrate 1a portion under the waveguide 70 and the horn apertural area 80 formed between the first electrode 4 and the second electrode 2 may be removed fully.

The overlay insulating film 18 may be formed on the active element 90, the first electrode 4, and the second electrode 2. For example, the overlay insulating film 18 is composed of an SiO₂ film ranging from approximately 0.1 μm to approximately 10 μm in thickness. The overlay insulating film 18 is preferably formed ranging from approximately 0.6 μm to approximately 5 μm in thickness. Since other structures are the same as the structures shown in FIG. 16, the explaining of each part is omitted.

In FIG. 39, the thickness of the thin-layered semiconductor substrate 1a is approximately 20 μm, for example. Moreover, the length of the waveguide 70 is equal to or less than approximately 700 μm, for example, and the length of the horn apertural area 80 is also equal to or less than approximately 700 μm. The whole length of the THz oscillation device according to the modified example 1 including the MIM reflector 50 is equal to or less than approximately 1,600 μm, for example.

According to the THz oscillation device 38 according to the modified example 1, it becomes possible to control the effect of the semiconductor substrate 1 by thin-layering the semiconductor substrate 1, the THz wave can be radiated in the longitudinal direction against the semiconductor substrate 1 with improved directivity at high-efficiency and high-output, and furthermore, the integration is easy.

Modified Example 2

Figure 40:
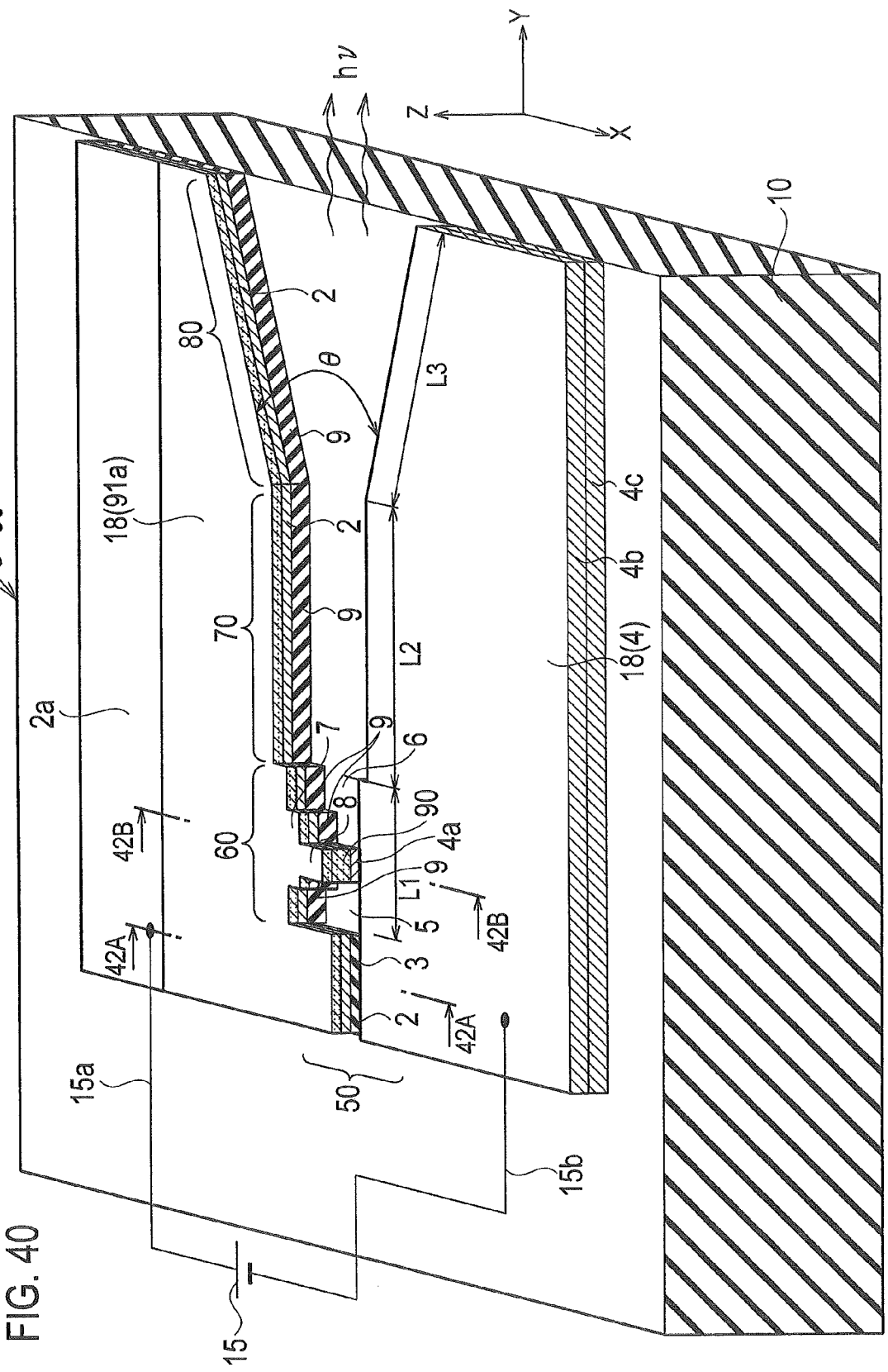
FIG. 40 is a schematic bird's-eye view of a THz oscillation device according to a modified example 2 applicable to the solution testing equipment according to the first embodiment.

FIG. 40 illustrates a schematic bird's-eye view structure of a modified example 2 of the THz oscillation device 38 applied to the solution testing equipment 30 according to the first embodiment. Moreover, FIG. 41 illustrates a schematic top view diagram of a radiation pattern structure composed of the first electrode 4, the second electrode 2a, and the semiconductor layer 91a corresponding to those of FIG. 40. Moreover, FIG. 42A illustrates a schematic cross-sectional structure taken in the line 42A-42A of FIG. 41, and FIG. 42B illustrates a schematic cross-sectional structure taken in the line 42B-42B of FIG. 41.

As shown in FIGS. 40, 41, 42A and 42B, the THz oscillation device 38 according to the modified example 2 includes: an insulator substrate 10; a first electrode 4 (4a, 4b, 4c) disposed on the insulator substrate 10; an inter-electrode insulating layer 3 disposed on the first electrode 4a; an interlayer insulating film 9 disposed on the insulator substrate 10; second electrodes 2, 2a disposed on the interlayer insulating film 9, the second electrodes 2, 2a disposed to be opposite to the first electrode 4a via the inter-electrode insulating layer 3 toward the first electrode 4; a semiconductor layer 91a disposed on the second electrode 2; an MIM reflector 50 formed between the first electrode 4a and the second electrode 2 so that the inter-electrode insulating layer 3 is sandwiched therebetween; a resonator 60 disposed between the first electrode 4 and the second electrode 2 opposite to each other on the insulator substrate 10, the resonator 60 adjacent to the MIM reflector 50; an active element 90 disposed at a substantially central part of the resonator 60; a waveguide 70 disposed between the first electrode 4 and the second electrode 2 opposite to each other on the insulator substrate 10, the waveguide 70 adjacent to the resonator 60; and a horn apertural area 80 disposed between the first electrode 4 and the second electrode 2 opposite to each other on the insulator substrate 10, the horn apertural area 80 adjacent to the waveguide 70.

Figure 42A:
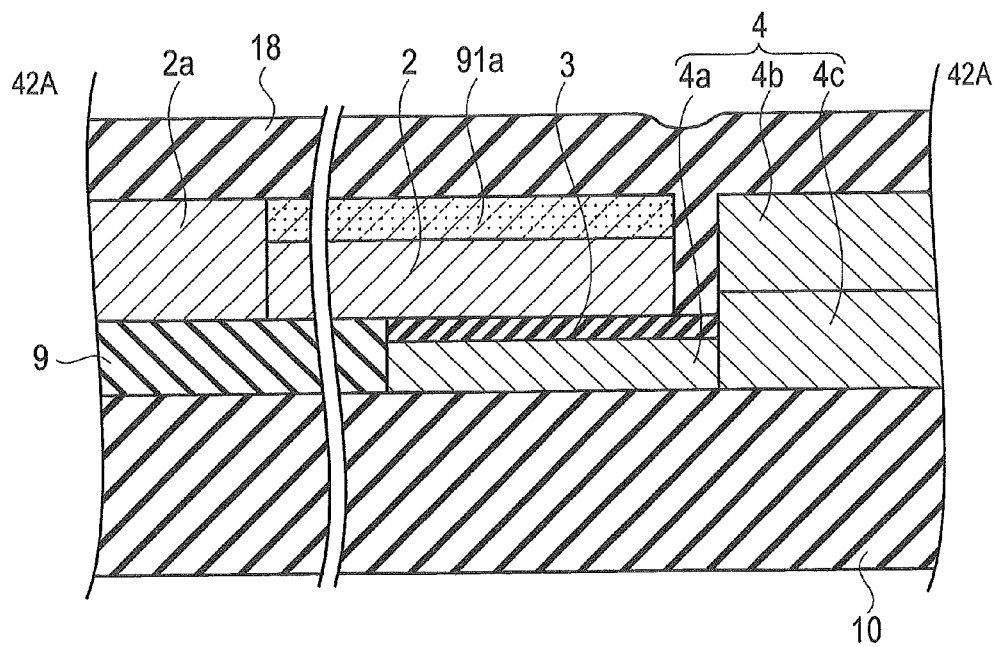
FIG. 42A is a schematic cross-sectional structure diagram taken in the line 42A-42A line of FIGS. 40 and 41.
Figure 42B:
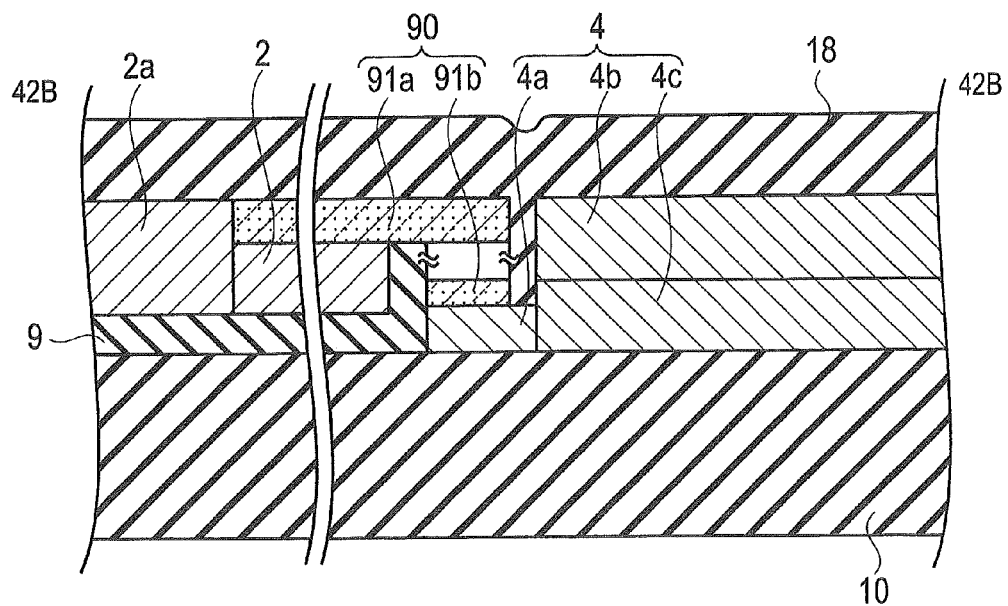
FIG. 42B is a schematic cross-sectional structure diagram taken in the line 42B-42B of FIGS. 40 and 41.

As shown in FIGS. 40, 42A and 42B, an overlay insulating film 18 may be formed on the first electrode 4 (4a, 4b, 4c), the second electrodes 2 and 2a, and the semiconductor layer 91a. For example, the overlay insulating film 18 is composed of an $SiO_2$ film ranging from approximately 0.1 μm to approximately 10 μm in thickness. The overlay insulating film 18 is preferably formed ranging from approximately 0.6 μm to approximately 5 μm in thickness.

The horn apertural area 80 is composed of an aperture horn antenna. The angular aperture θ of the horn apertural area is preferable to set as equal to or less than approximately 10 degrees, for example, from the viewpoint of giving the directional characteristics in the radiation direction of the electromagnetic wave (hv). The length L3 of the horn apertural area 80 is equal to or less than approximately 700 μm, for example. The aperture width in the tip region of the horn apertural area 80 is approximately 160 μm, for example.

The waveguide 70 is disposed at the apertural area of the resonator 60. The length L2 of the waveguide 70 is equal to or less than approximately 700 μm, for example. Moreover, the distance between the first electrode 4 and the second electrode 2 in the waveguide 70 is approximately 24 μm, for example.

In addition, the horn shape of the horn apertural area 80 is a structure required in order to radiate the electromagnetic wave in the air. Because of the horn shape, the electromagnetic wave can be efficiently radiated with sufficient impedance matching property in the air. In addition, the shape of the horn may be not only a linearity shape, but also a nonlinear shape, a curve profile, a secondary curve profile, a parabola shape, a stair-like shape, etc.

Two recessed regions 5, 6 are formed at the resonator 60, and a protruded region 7 is formed to be inserted between the two recessed regions 5, 6. A salient region 8 is formed at the substantially central part of the protruded region 7 of the semiconductor layer 91a, and the active element 90 is disposed at an under side of the salient region 8 so as to be inserted between the salient region 8 and the second electrode 2.

The length L1 of the resonator 60 is equal to or less than approximately 30 μm, for example. The length of the salient region 8 is equal to or less than approximately 6 μm, for example. The width of the recessed regions 5, 6 (distance between the first electrode 4 and the second electrode 2) is approximately 4 μm, for example. The size of the active element 90 is approximately 1.4 μm², for example. However, the size of the active element 90 is not be limited to such a value, and may be equal to or less than approximately 5.3 μm², for example. The size of each part of the resonator 60 is not limited to the above-mentioned size, and is suitably set up on a design according to the frequency of the electromagnetic waves to oscillate.

As shown in FIG. 40, the distance between the first electrode 4 and the second electrode 2 of the part on which the resonator 60 is formed is narrower compared with the distance between the first electrode 4 and the second electrode 2 in the waveguide 70.

The MIM reflector 50 is disposed at the closed area in the opposite side of the apertural area of the resonator 60. Because of the layered structure of the MIM reflector 50 composed of metal/insulator/metal, the first electrode 4 and the second electrode 2 are short-circuited in terms of high frequency. Moreover, the MIM reflector 50 produces an effect to reflect high-frequency waves as it is open in terms of direct current.

Each of the first electrode 4 (4a, 4b, 4c) and the second electrodes 2, 2a is composed of metal layered structure, e.g., Au/Pd/Ti, and the Ti layer is a buffer layer for excellent contact condition with the insulator substrate 10. The thickness of each part of the first electrodes 4a, 4b, 4c and the second electrodes 2, 2a is approximately hundreds of nanometers, for example, and the layered-structure planarized as a whole as shown in FIGS. 42A and 42B is achieved. Each of the first electrode 4 and the second electrode 2 can be formed with a vacuum deposition method or a sputtering technique.

More particularly, the first electrode 4a and the first electrode 4c are composed of Au/Pd/Ti, for example, and the first electrode 4b is composed of Au/Ti, for example. The second electrode 2 is composed of Au/Pd/Ti, for example, and the second electrode 2a is composed of Au/Ti, for example.

Note that when an extraction electrode is formed from a bonding wire 15b, the Ti layer which forms a surface layer of the first electrode 4b is preferable to be removed in order to reduce contact resistance. Similarly, when an extraction electrode is formed from a bonding wire 15a, the Ti layer which forms a surface layer of the second electrode 2a is preferable to be removed in order to reduce contact resistance.

The inter-electrode insulating layer 3 can be formed of an $SiO_2$ film, for example. Other films, e.g. an $Si_3N_4$ film, a SiON film, an $HfO_2$ film, an $Al_2O_3$ film, etc. are also applicable to the inter-electrode insulating layer 3. The thickness of the inter-electrode insulating layer 3 can be determined in consideration of the geometric plane size of the MIM reflector 50 and the required capacitor value on circuit characteristics, for example, and may be tens to hundreds of nanometers. The inter-electrode insulating layer 3 can be formed by using the CVD method or the spattering technique.

Similarly, the interlayer insulating film 9 can be formed of an $SiO_2$ film, for example. Other films, e.g. an $Si_3N_4$ film, a SiON film, an $HfO_2$ film, an $Al_2O_3$ film, etc. are also applicable to the interlayer insulating film 9. Regarding the thickness of the interlayer insulating film 9, as shown in FIG. 42A, the whole thickness of the second electrode 2a and the interlayer insulating film 9 is set up to become the substantially same as the thickness of the first electrode 4. The interlayer insulating film 9 can be formed by using the CVD method or the spattering technique.

It is preferable that the insulator substrate 10 is formed of substrate materials having a lower dielectric constant than that of the semiconductor layer 91a, from a viewpoint of extracting the electric wave efficiently. As the insulator substrate 10 formed of such low dielectric constant materials, a polyimide resin substrate, a Teflon (registered trademark) substrate, etc. are applicable, for example. The thickness of the insulator substrate 10 is approximately 200 µm, for example.

In the THz oscillation device according to the modified example 2, since the air exists on the upper side thereof, the relative permittivity $\in_{air}$ is 1. Since the relative permittivity $\in_{poly}$ of the polyimide resin is 3.5 if the polyimide resin substrate is used as the insulator substrate 10, the ratio of the oscillation output to the lower part of the insulator substrate 10 to the whole oscillation output at the time of operation as an oscillation device is expressed by the equation $\in_{poly}^{3/2}/(\in_{air}^{3/2}+\in_{poly}^{3/2})=0.87$. More specifically, approximately 87% of the whole oscillation outputs are radiated to the insulator substrate 10 side, and therefore the oscillation output radiated in the longitudinal direction thereof from the horn apertural area 80 relatively increases. Similarly, at the time of operation as the detection device, the THz wave is efficiently detectable from the horn apertural area 80 in the longitudinal direction thereof.

Furthermore, since if the Teflon (registered trademark) resin substrate is used as the insulator substrate 10, the relative permittivity $\in_{tef}$ of Teflon (registered trademark) is 2.1, the ratio of the oscillation output to the lower part of the insulator substrate 10 to the whole oscillation output at the time of operation as an oscillation device is expressed by the equation $\in_{tef}^{3/2}/(\in_{air}^{3/2}+\in_{tef}^{3/2})=0.75$. More specifically, at the time of operation as the oscillation device, approximately 75% of the whole oscillation outputs are radiated to the insulator substrate 10 side, and therefore the oscillation output radiated in the longitudinal direction thereof from the horn apertural area 80 relatively increases. Similarly, at the time of operation as the detection device, the THz wave is efficiently detectable from the horn apertural area 80 in the longitudinal direction thereof.

The MIM reflector 50 is formed of a structure in which the inter-electrode insulating layer 3 is inserted between the first electrode 4a and the second electrode 2, as shown in FIG. 42A. Moreover, as clearly from FIG. 42B, the active element 90 composed of the RTD is disposed on the insulator substrate 10 via the first electrode 4a. The first electrode 4a is disposed to be contacted with the n$^+$ GaInAs layer 91b of RTD. The second electrode 2 is disposed to be contacted with the n$^+$ GaInAs layer 91a of RTD. Furthermore, the first electrode 4 (4b, 4c) is disposed to extend on the insulator substrate 10.

Thus, since the first electrode 4 is disposed to extend on the insulator substrate 10, the first electrode 4 and the second electrode 2 are not short-circuited to each other, thereby applying predetermined DC bias voltage between the n$^+$ GaInAs layer 91a and the n$^+$ GaInAs layer 91b of the RTD.

In addition, the bonding wire 15b is connected to the first electrode 4, the bonding wire 15a is connected to the second electrode 2a, and a DC power supply 15 is connected between the first electrode 4 and the second electrode 2a. Moreover, a resistance (not shown) for preventing a parasitic oscillation is connected between the first electrode 4 and the second electrode 2a.

In the structure of the THz oscillation device according to the modified example 2, FIGS. 42A and 42B illustrate the structure which is turned upside down after bonding the insulator substrate 10 directly on the first electrode 4 and on the second electrode 2 via the interlayer insulating film 9, and then removing the semiconductor substrate 1 by etching. As shown in FIGS. 42A and 42B, in the THz oscillation device according to the modified example 2, the semiconductor layer 91a is disposed on the second electrode 2, but the second electrode 2a is also exposed thereto. Accordingly, electrode extraction process, e.g. wire bonding, can be easily performed with respect to the second electrode 2a.

In the fabrication method of the THz oscillation device according to the modified example 2, as shown in FIGS. 17A and 17B, after forming the semiconductor layer 91a on the semiconductor substrate 1, the width of the semiconductor layer 91a is formed narrowly, and the pattern width of the second electrode 2 formed on the semiconductor layer 91a is formed narrowly by patterning. The relative thick second electrode 2a having the predetermined width connected to the second electrode 2 is formed on the remaining portion. As a result, the structure in which the second electrode 2a is contacted with the semiconductor substrate 1 is achieved, as shown in FIGS. 17A and 17B.

Next, as shown in FIGS. 42A and 42B, there is achieved the structure turned upside down after bonding the insulator substrate 10 directly on the first electrode 4 and on the second electrode 2 via the interlayer insulating film 9, and then removing the semiconductor substrate 1 by etching.

Next, as shown in FIG. 40 the bonding wire 15b is connected to the first electrode 4, and the bonding wire 15a is connected to the second electrode 2a, thereby extracting the electrodes.

The semiconductor substrate 1 is formed of a semi insulating InP substrate, for example, and the thickness thereof is approximately 600 µm, for example. A hydrochloric acid based etching solution is applicable, for example, as an etching solution for the InP substrate.

Figure 43:
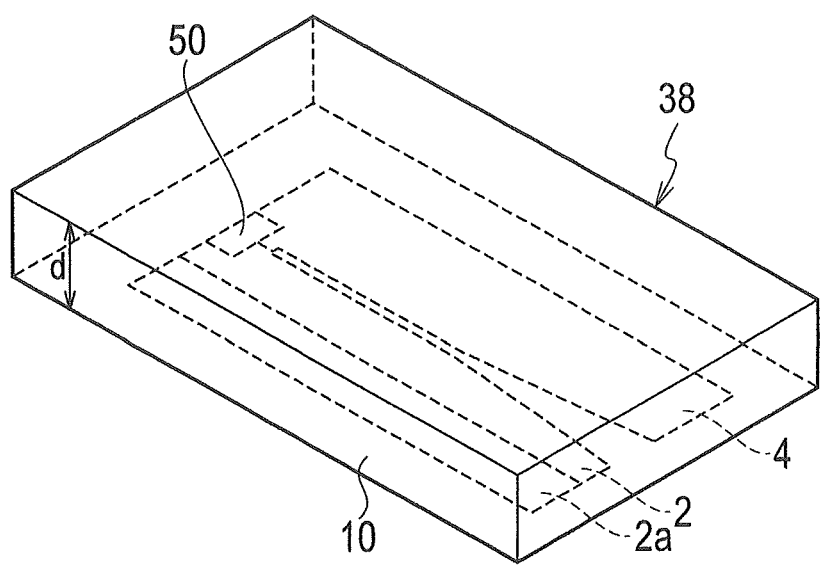
FIG. 43 is a schematic bird's-eye view showing an aspect that an insulator substrate is bonded on a sample surface and then a semiconductor substrate is removed in a THz oscillation device according to a modified example 2.
Figure 44:
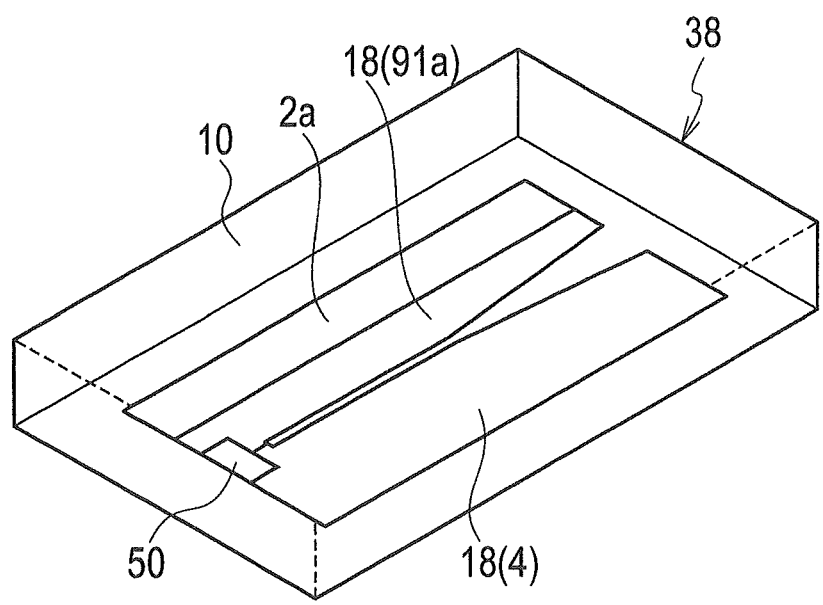
FIG. 44 is a schematic bird's-eye view showing an aspect that the THz oscillation device according to the modified example 2 shown in FIG. 43 is observed from the back side surface thereof.

In the THz oscillation device 38 according to the modified example 2, FIG. 43 illustrates a schematic bird's-eye view structure after the process of bonding the insulator substrate 10 of which the thickness is d on the sample surface, and then removing the semiconductor substrate 1 by etching, and FIG. 44 illustrates a schematic bird's-eye view structure in which the THz oscillation device according to the modified example 2 shown in FIG. 43 observed from the back side surface thereof. As clearly from FIG. 43, the first electrode 4 is directly bonded on the insulator substrate 10. The second electrodes 2, 2a are not shown in FIG. 43, but are bonded on the insulator substrate 10 via the interlayer insulating film 9, as shown in FIGS. 42A and 42B. The detailed structure shown in FIG. 44 corresponds to the structure shown in FIG. 40.

A schematic cross-sectional structure of the RTD is similarly illustrated as FIG. 18A, as the THz oscillation device 38 according to the modified example 2. Moreover, a schematic cross-sectional structure of the modified example is similarly illustrated as FIG. 18B.

FIG. 18A shows a constructional example disposed on the semiconductor substrate 1, but the semiconductor substrate 1 is removed by etching, after bonding the insulator substrate 10 on the first electrode 4a, in the subsequent process. Accordingly, FIG. 18A corresponds to the schematic cross-sectional structure near the active element 90 before the process of bonding the insulator substrate 10.

As mentioned above, the RTD is typical as the active element 90, but the active element 90 can be composed also from diodes or transistors except for the RTD. As other active elements, a TUNNETT diode, an IMPATT diode, a GaAsFET, a GaN baseds FET, HEMT, and HBT, etc. are also applicable, for example.

According to the THz oscillation device according to the modified example 2, the directivity in the longitudinal direction is improved by using the low-permittivity insulator substrate 10, the THz wave can be oscillated with high directivity in the longitudinal direction against the substrate at high-efficiency and high-output, and furthermore, the integration is easy.

In FIGS. 40, 41, 42A, 42B, 43 and 44, the overlay insulating film 18 is composed of an $SiO_2$ film ranging from approximately 0.1 µm to approximately 10 µm in thickness. The overlay insulating film 18 is preferable to be formed ranging from approximately 0.6 µm to approximately 5 µm in thickness. If such an overlay insulating film 18 is formed, a degree of the radiation pattern variation of the THz wave at the time of contacting the solution can be advanced.

Modified Examples 3 and 4

Figures 45A, 45B:
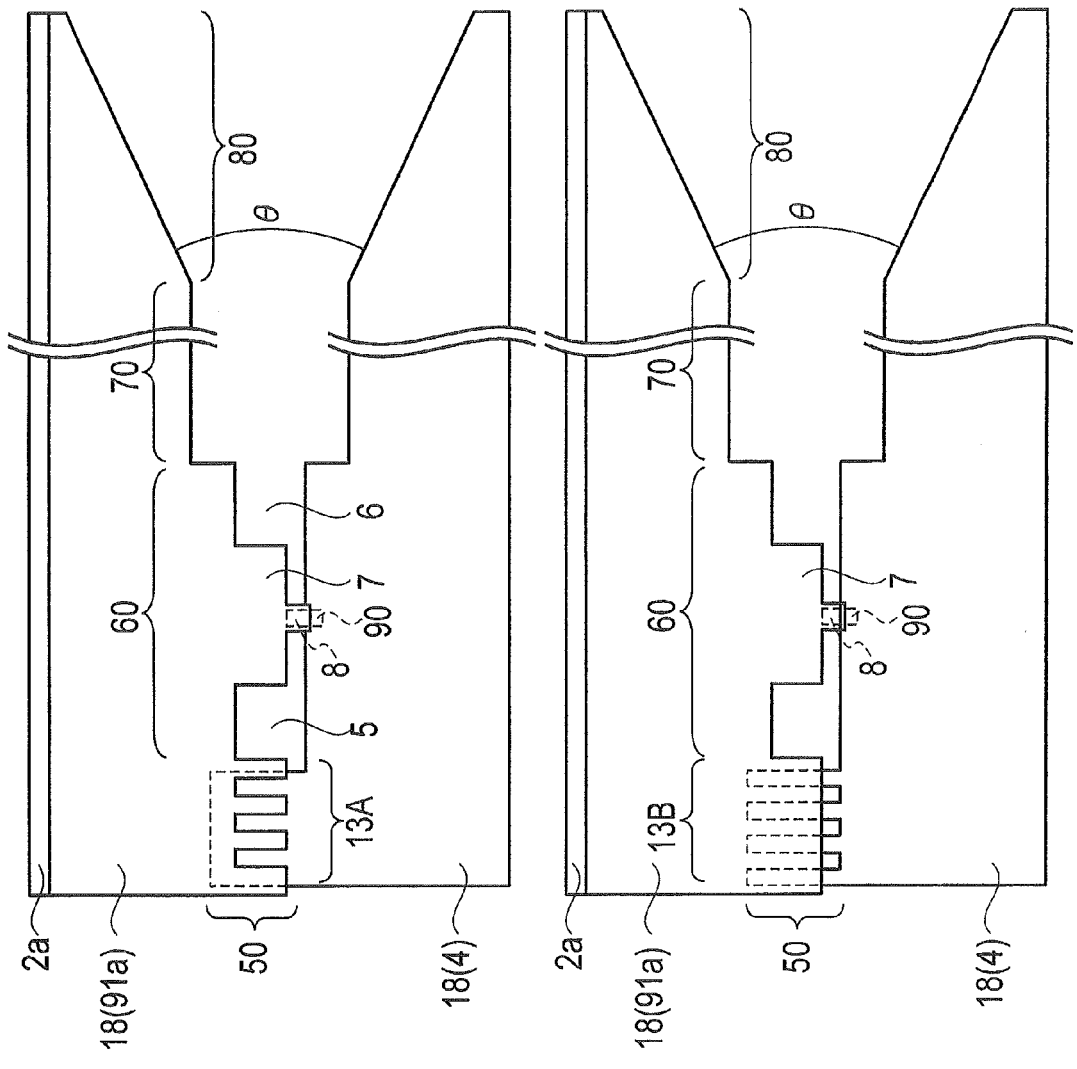
FIG. 45A is a schematic top view diagram of an electrode radiation pattern structure of a THz oscillation device according to a modified example 3 applied to the solution testing equipment according to the first embodiment.
FIG. 45B is a schematic top view diagram of an electrode pattern structure of a THz oscillation device according to a modified example 4 applied to the solution testing equipment according to the first embodiment.

FIG. 45A illustrates an electrode pattern structure of the THz oscillation device according to modified example 3, and FIG. 45B illustrates an electrode pattern structure of the THz oscillation device according to the modified example 4.

The electrode pattern structure of the terahertz oscillation device according to the modified example 3 is an example for providing the second electrode 2 composing the MIM reflector 50 with s stub structure, and the electrode pattern structure of the terahertz oscillation device according to the modified example 4 is an example for providing the first electrode 4 composing the MIM reflector 50 with a stub structure. As clearly from FIG. 42A, although the semiconductor layer 91a is shown in FIGS. 45A and 45B since the semiconductor layer 91a is disposed on the second electrode 2, a pattern of the second electrode 2 is disposed with the same pattern shape as that of the semiconductor layer 91a, under the semiconductor layer 91a.

More specifically, as shown in FIG. 45A, the second electrode 2 is provided with a plurality of the stubs 13A in a portion composing the MIM reflector 50.

Moreover, as shown in FIG. 45B, the first electrode 4 is provided with a plurality of the stubs 13B in a portion composing the MIM reflector 50.

The plurality of the stubs 13A or 13B may be disposed to face the resonator 60 at equal interval, or may be disposed at varying intervals.

Both of the second electrode 2 and the first electrode 4 may be provided with the plurality of the stubs by combining the aforementioned modified examples 3 and 4.

In addition, in the modified example 3, leak electromagnetic waves transmitted to the closed area side are reflected from the stub 13A and the MIM reflector, and are returned to the aperture side. Then, since the reflected electromagnetic waves are radiated as an output, the electromagnetic waves oscillated from the active element 90 become high power.

Since the operation of the stub 13B is the same as that of the stub 13A also in the modified example 4, the duplicated description will be omitted.

Since both side of the second electrode 2 and the first electrode 4 are provided with multi stages of the stubs, an equivalent very high reflection factor can be achieved with the approximately half number of stubs compared with the case of providing only one side therewith. Moreover, since flexibility of design at the time of determining frequency ranges and a center frequency can be improved, it is very effective on the design. The length of, the number of, and the interval of the stub provided to the both sides of the second electrode 2 and the first electrode 4 do not necessarily require to be equal to each other, but can be changed freely in the design.

According to the THz oscillation devices according to the modified examples 3 and 4, the directivity in the longitudinal direction is improved by using the low-permittivity insulator substrate, the THz wave can be oscillated and detected with high directivity in the longitudinal direction against the substrate at high-efficiency and high-output, and furthermore, the integration is easy.

According to the THz oscillation devices according to the modified examples 3 and 4, the directivity in the longitudinal direction is improved by using the low-permittivity insulator substrate, and the THz wave can be oscillated and detected having high directivity in the direction horizontal to the substrate with further efficiently by combining the stub structure with the electrode composing the MIM reflector.

In FIG. 42, the overlay insulating film 18 is composed of an $SiO_2$ film ranging from approximately 0.1 µm to approximately 10 µm in thickness. The overlay insulating film 18 is preferable to be formed ranging from approximately 0.6 µm to approximately 5 µm in thickness. If such an overlay insulating film 18 is formed, a degree of the radiation pattern variation of the THz wave at the time of contacting the solution can be advanced.

Modified Example 5

Figure 46:
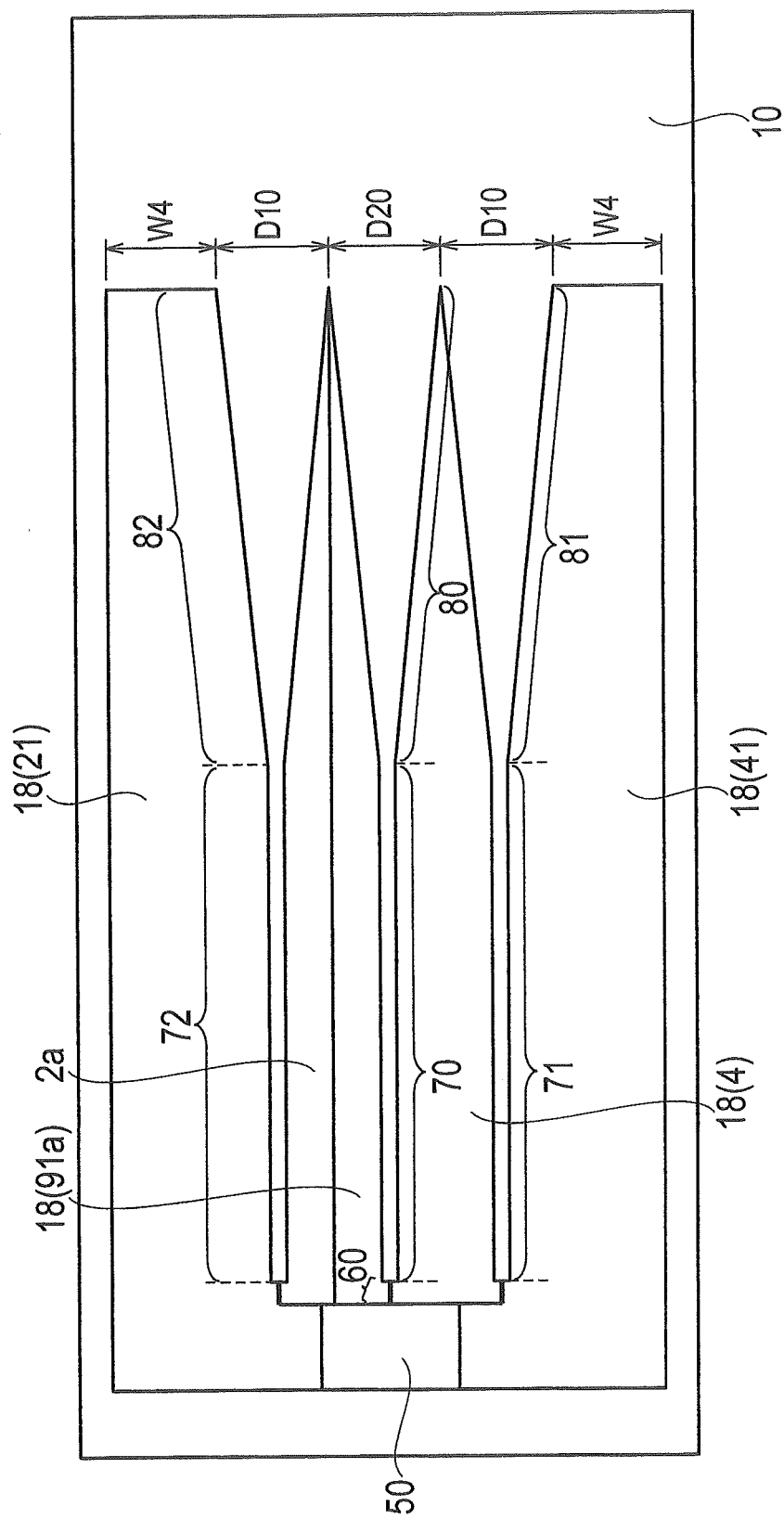
FIG. 46 is a schematic top view diagram of a THz oscillation device according to a modified example 5 applied to the solution testing equipment according to the first embodiment.

FIG. 46 illustrates a schematic plane configuration of an electrode pattern structure of the THz oscillation device 38 according to a modified example 5 applied to the solution testing equipment 30 according to the first embodiment.

Also in the THz oscillation device 38 according to the modified example 5, the duplicated description will be omitted hereinafter, since a structure composed of the first electrode 4 (4a, 4b, 4c), the second electrodes 2, 2a, the MIM reflector 50, the resonator 60, and the active element 90 is the same as that of the modified example 2.

As shown in FIG. 46, the THz oscillation device according to the modified example 5 includes: an insulator substrate 10; a first electrode 4 (4a, 4b, 4c) disposed on the insulator substrate 10: an inter-electrode insulating layer 3 (FIG. 42 A, FIG. 42B) disposed on the first electrode 4a (FIG. 42A, FIG. 42B); an interlayer insulating film 9 (FIG. 42A, FIG. 42B) disposed on the insulator substrate 10; second electrodes 2, 2a disposed on the interlayer insulating film 9, the second electrodes 2, 2a disposed to be opposite to the first electrode 4a via the inter-electrode insulating layer 3 toward the first electrode 4; a semiconductor layer 91a disposed on the second electrode 2; a first slot line electrode 41 disposed on the insulator substrate 10 to be adjacent to the first electrode 4, the first slot line electrode 41 disposed to be opposite to the first electrode 4 in an opposite side of the second electrode 2a; a second slot line electrode 21 disposed on the insulator substrate 10 to be adjacent to the second electrode 2a, the second slot line electrode 21 disposed to be opposite to the second electrode 2a in an opposite side of the first electrode 4; an MIM reflector 50 formed between the first electrode 4a and the second electrode 2 so that the inter-electrode insulating layer 3 is sandwiched therebetween; a resonator 60 disposed between the first electrode 4 and the second electrode 2 opposite to each other on the insulator substrate 10, the resonator 60 adjacent to the MIM reflector 50; an active element 90 disposed at a substantially central part of the resonator 60; a first waveguide 70 disposed between the first electrode 4 and the second electrode 2 opposite to each other on the insulator substrate 10, the first waveguide 70 adjacent to the resonator 60; and a first horn apertural area 80 disposed between the first electrode 4 and the second electrode 2 opposite to each other on the insulator substrate 10, the first horn apertural area 80 adjacent to the first waveguide 70; a second waveguide 71 disposed between the first electrode 4 and the first slot line electrode 41 opposite to each other on the insulator substrate 10; a second horn apertural area 81 disposed between the first electrode 4 and the first slot line electrode 41 opposite to each other on the insulator substrate 10, the second horn apertural area 81 adjacent to the second waveguide 71; a third waveguide 72 disposed between the second electrode 2a and the second slot line electrode 21 opposite to each other on the insulator substrate 10; and a third horn apertural area 82 disposed between the second electrode 2a and the second slot line electrode 21 opposite to each other on the insulator substrate 10, the third horn apertural area 81 adjacent to the third waveguide 72.

In the same manner as the modified example 2, the RTD is typical as the active element 90, but the active element 90 can be composed also from diodes or transistors except for the RTD. As other active elements, a TUNNETT diode, an IMPATT diode, a GaAsFET, a GaN baseds FET, HEMT, and HBT, etc. are also applicable, for example.

The horn apertural areas 80 to 82 compose an aperture horn antenna.

In the THz oscillation device and THz detection device according to the modified example 5, as shown in FIG. 46, the width W4 of the slot line electrodes 21 and 41 in an output terminal is approximately 160 µm, for example. As shown in FIG. 46, the width D20 of the horn apertural area 80, the width D10 of the horn apertural areas 81 and 82, and the width W4 of the slot line electrodes 21 and 41 in the output terminal can be suitably changed.

The waveguide 70 is disposed at the apertural area of the resonator 60.

The MIM reflector 50 is disposed at closed area in an opposite side of the apertural area of the resonator 60.

The second electrode 2 may be provided with a plurality of the stubs as well as the modified example 3 shown in FIG. 45A in a portion which composes the MIM reflector 50. Similarly, in a part which composes the MIM reflector 50, the second electrode 2 may be provided with a plurality of stubs as well as the modified example 4 shown in FIG. 45B.

Moreover, in the structure mentioned above, the plurality of stubs may be disposed at equal intervals facing to the resonator 60, or may be placed at varying intervals.

Moreover, it is preferable that the insulator substrate 10 is formed of substrate materials having a lower dielectric constant than that of the semiconductor layer 91a, from a viewpoint of extracting the electric wave efficiently in a longitudinal direction with high directivity. As the insulator substrate 10 formed of such low dielectric constant materials, a polyimide resin substrate, a Teflon (registered trademark) substrate, etc. are applicable, for example, as well as the first embodiment.

If the polyimide resin substrate is used as the insulator substrate 10, approximately 87% of the whole oscillation outputs are radiated to the insulator substrate 10 side, and therefore the oscillation output radiated in the longitudinal direction thereof from the horn apertural area 80 relatively increases, in the same manner as the modified example 2.

If the Teflon (registered trademark) resin substrate is used as the insulator substrate 10, approximately 75% of the whole oscillation outputs are radiated to the insulator substrate 10 side, and therefore the oscillation output radiated in the longitudinal direction thereof from the horn apertural area 80 relatively increases, in the same manner as the modified example 2.

In the THz oscillation device according to the modified example 5, compared with the modified example 2, the directivity further improves by disposing one pair of the same taper-formed slot line electrodes 21 and 41 at both sides of the tapered slot antenna composed of the first electrode 4 and the second electrode 2 connected to the active element 90.

According to the terahertz oscillation device according to the modified example 5, since one pair of the taper-shaped slot line electrodes 41 and 21 are disposed in parallel on both sides of the tapered slot antenna composed of the first electrode 4 and the second electrode 2, even if the tapered slot antenna is integrated on the insulator substrate 10, the influence of the insulator substrate 10 can be inhibited, and sufficient directivity can be achieved.

The electric fields spreading from the taper slot antenna composed of the first electrode 4 and the second electrode 2 of the central part are pulled in one pair of the slot line electrodes 41 and 21 provided in both sides thereof, and is reflected from the end face of the slot line electrodes 41 and 21, and return to the first electrode 4 and the second electrode 2 of the central part. At this time, the standing wave is formed in the first electrode 4 and the second electrode 2 of the central part, and the slot line electrodes 41 and 21, and the electromagnetic waves are radiated to the outside by the reflected electric fields. The radiation field from the first electrode 4 and the second electrode 1 of the central part, and one pair of slot line electrodes 41 and 21 interfere with each other, thereby improving the directivity.

According to the terahertz oscillation device according to the modified example 5, the directivity in the longitudinal direction is improved by using the low-permittivity insulator substrate, and the slot line electrodes are disposed in parallel to generate the standing wave effectively. Accordingly, the THz wave can be radiated in the longitudinal direction against the substrate at high-efficiency and high-output, and furthermore, the integration is easy.

In FIG. 46, the overlay insulating film 18 is composed of an $SiO_2$ film ranging from approximately 0.1 µm to approximately 10 µm in thickness. The overlay insulating film 18 is preferable to be formed ranging from approximately 0.6 µm to approximately 5 µm in thickness. If such an overlay insulating film 18 is formed, a degree of the radiation pattern variation of the THz wave at the time of contacting the solution can be advanced.

Modified Example 6

Figure 47:
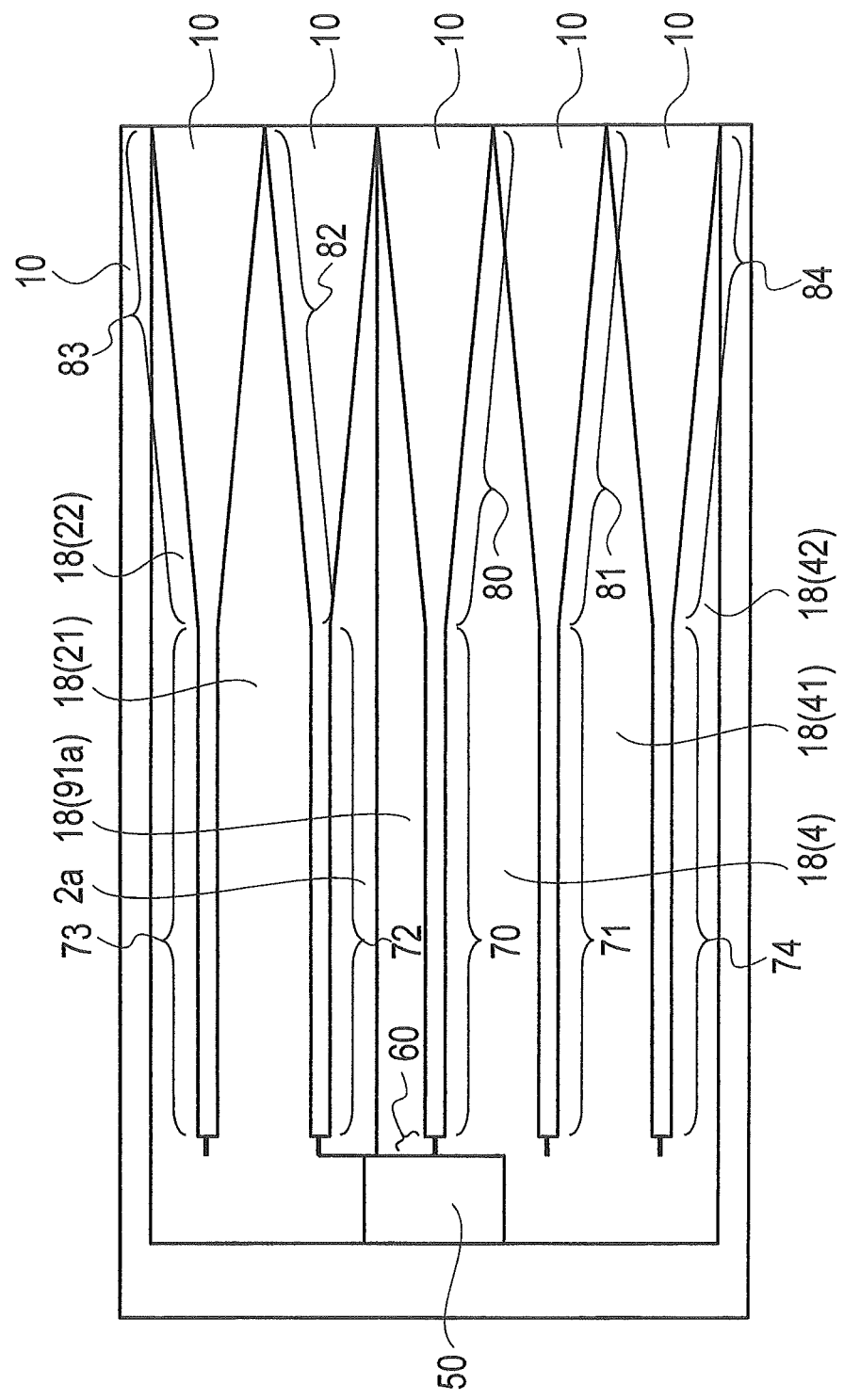
FIG. 47 is a schematic top view diagram of a THz oscillation device according to a modified example 6 applied to the solution testing equipment according to the first embodiment.

FIG. 47 illustrates a schematic plane configuration of an electrode pattern structure of the THz oscillation device 38 according to a modified example 6 applied to the solution testing equipment 30 according to the first embodiment.

Also in the THz oscillation device 38 according to the modified example 6, the duplicated description will be omitted hereinafter, since the structure composed of the first electrode 4, the second electrode 2, the MIM reflector 50, the resonator 60, the active element 90, the first slot line electrode 41, and the second slot line electrode 21 is the same as that of the first embodiment.

In the THz oscillation device 38 according to the modified example 6, as shown in FIG. 47, one pair of the slot line electrodes 22 and 42 are further disposed in parallel in the electrode pattern structure of the modified example 5 shown in FIG. 46. More specifically, the THz oscillation device 38 includes: a third slot line electrode 42 disposed on the insulator substrate 10 to be adjacent to the first slot line electrode 41, the third slot line electrode 42 disposed to be opposite to the first slot line electrode 41 in an opposite side of the first electrode 4; a fourth slot line electrode 22 disposed on the insulator substrate 10 to be adjacent to the second slot line electrode 21, the fourth slot line electrode 22 disposed to be opposite to the second slot line electrode 21 in an opposite side of the second electrode 2a; a fourth waveguide 74 disposed between the first slot line electrode 41 and the third slot line electrode 42 opposite to each other on the insulator substrate 10; a fourth horn apertural area 84 disposed between the first slot line electrode 41 and the third slot line electrode 42 opposite to each other on the insulator substrate 10, the fourth horn apertural area 84 adjacent to the fourth waveguide 77; a fifth waveguide 73 disposed between the second slot line electrode 21 and the fourth slot line electrode 22 opposite to each other on the insulator substrate 10; and a fifth horn apertural area 83 disposed between the second slot line electrode 21 and the fourth slot line electrode 22 opposite to each other on the insulator substrate 10, the fifth horn apertural area 84 adjacent to the fifth waveguide 73.

Moreover, it is preferable that the insulator substrate 10 is formed of substrate materials having a lower dielectric constant than that of the semiconductor layer 91a, from a viewpoint of extracting the electric wave efficiently in a longitudinal direction with high directivity. As the insulator substrate 10 formed of such low dielectric constant materials, a polyimide resin substrate, a Teflon (registered trademark) substrate, etc. are applicable, for example, as well as the first embodiment.

In the structure shown in FIG. 47, one pair of the slot line electrodes 22, 42 are further disposed in parallel on both outsides of the slot line electrodes 21, 41, thereby further improving the directivity.

According to the THz oscillation device 38 according to the modified example 6, the directivity in the longitudinal direction is improved by using the low-permittivity insulator substrate 10, two pair of the slot line electrodes are disposed in parallel to generate the standing wave effectively. Accordingly, the THz wave can be radiated in the longitudinal direction against the substrate at high-efficiency and high-output, and furthermore, the integration is easy.

In FIG. 47, the overlay insulating film 18 is composed of an $SiO_2$ film ranging from approximately 0.1 μm to approximately 10 μm in thickness. The overlay insulating film 18 is preferable to be formed ranging from approximately 0.6 μm to approximately 5 μm in thickness. If such an overlay insulating film 18 is formed, a degree of the radiation pattern variation of the THz wave at the time of contacting the solution can be advanced.

According to the first embodiment, there can be provided the solution testing equipment which can test the ingredient of the solution etc. on the basis of the variation of the radiation pattern of the THz wave in response to the relative permittivity of the solution as a test object.

According to the solution testing equipment according to the first embodiment, since the ingredient of the solution etc. can be tested on the basis of the variation of the radiation pattern of the THz wave in response to the relative permittivity $\in$ of the solution, it becomes possible to perform sensing, e.g. sensing of cells, antigen-antibody reactions, using the solution testing equipment.

According to the solution testing equipment according to the first embodiment, it can obtain information on cells, for example, ranging from approximately 30 μm to approximately 50 μm in width and approximately 2 μm to approximately 3 μm in height by using the (hv) THz wave.

According to the first embodiment, there can be provided solution testing equipment which can detect the output variation of the THz oscillation device using the THz wave (hv) by contacting the liquid or cell on the RTD oscillation device, and can reduce the size and weight thereof.

In addition, in the aforementioned modified examples 1-6 of the first embodiment, although the THz oscillation device has been described, devices having the same structure as the aforementioned THz oscillation device are applicable also as the THz detection device.

[Second Embodiment]

Figure 48:
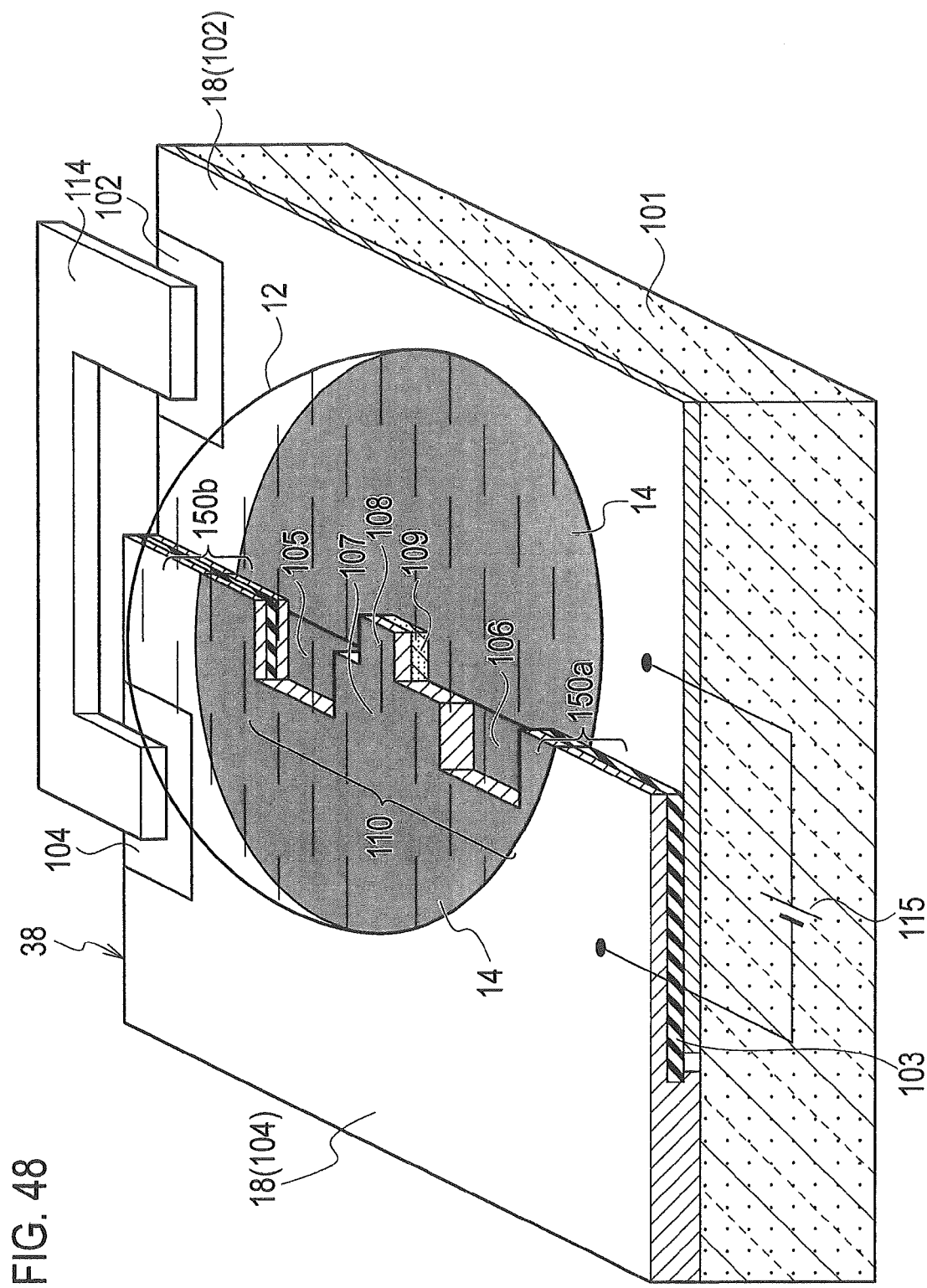
FIG. 48 is a schematic bird's-eye view of a THz oscillation device applied to a solution testing equipment according to the second embodiment.
Figure 49:
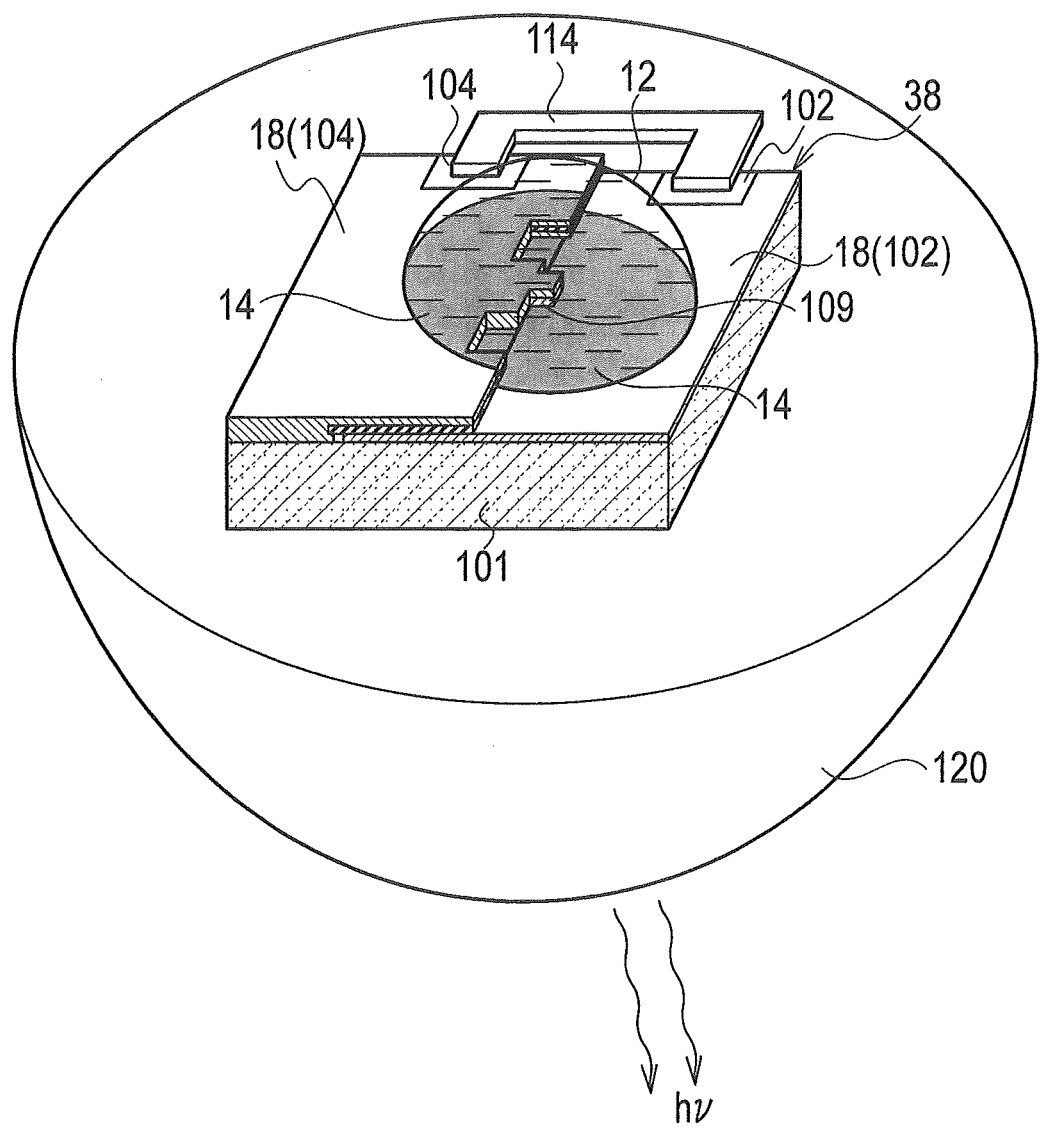
FIG. 49 is a schematic bird's-eye view of the THz oscillation device disposed on a silicon hemispherical lens, applied to the solution testing equipment according to the second embodiment.

FIG. 48 illustrates a schematic bird's-eye view configuration of a THz oscillation device 38 applied to a solution testing equipment 30 according to a second embodiment. FIG. 49 illustrates a schematic bird's-eye view configuration of the THz oscillation device 38 applied to the solution testing equipment 30 according to the second embodiment disposed on a silicon hemispherical lens 120.

More specifically, as shown in FIG. 48, an active element 109 composed of RTD near the center of a slot antenna 110 is disposed, and a layer on which metal and an insulator are layered is formed in both ends of the slot antenna 110. In the present embodiment, the metal layer composes a second electrode 104, and the second electrode 104 short-circuits with a first electrode 102 composed of metal in terms of high frequencies through an inter-electrode insulating layer 103.

Two recessed regions 105, 106 are formed at the central part of the second electrode 104 overlapped with the first electrode 102 via the inter-electrode insulating layer 103, and a convex region 107 is formed at the second electrode 104 to be sandwiched between the two recessed regions 105, 106. Moreover, a salient region 108 is formed at the substantially central part of the protruded region 107 of the second electrode 104, and the active element 109 is disposed at an under side of the salient region 108 so as to be inserted between the salient region 108 and the first electrode 102. In addition, DC power supply 115 is connected to the second electrode 104 and the first electrode 102, and a parasitic oscillation suppression resistance 114 formed with materials, such as bismuth (Bi), is connected to the second electrode 104 and the first electrode 102 in order to prevent a parasitic oscillation.

Semi insulating (SI) InP is used for the semiconductor substrate 101, for example. The slot antenna 110 made in both sides of the active element 109 serves as a resonator and a radiation antenna of electromagnetic waves. The oscillation device 38 has a structure where the electromagnetic waves are radiated to an upward and downward two-way with respect to the semiconductor substrate 101. Accordingly, for example, as shown in FIG. 49, it is necessary to newly provide a silicon hemispherical lens 120 for concentrating the electromagnetic waves (hv) radiated in the upward and downward vertical direction.

In the THz oscillation device 38 applied to the solution testing equipment 30 according to the second embodiment, the active element 109 disposed on the same plane as the insulating layer 103, such as a transistor or a diode, is disposed at the central part of the slot antenna 100, the both ends of slot transmission line is rectangular curved, and then the portion is covered with a layered structure composed of metal/insulator/metal. Accordingly, the portion covered with the layered structure of the metal/insulator/metal composes RF reflection units 150a, 150b, and becomes short circuit condition in terms of high frequencies, thereby composing the slot antenna 100. Since this slot antenna 110 is an opened state in terms of DC, it can supply DC to the active element 109.

In FIGS. 48 and 49, the overlay insulating film 18 is composed of an $SiO_2$ film ranging from approximately 0.1 μm to approximately 10 μm in thickness. The overlay insulating film 18 is preferable to be formed ranging from approximately 0.6 μm to approximately 5 μm in thickness. If such an overlay insulating film 18 is formed, a degree of the radiation pattern variation of the THz wave at the time of contacting the solution can be advanced.

Also in the solution testing equipment 30 according to the second embodiment, a device having the same structure is applicable to each of the THz oscillation device 38 and the THz detection device 44. Accordingly, there can be used the THz oscillation device 38 and the THz detection device 44 each fabricated at the same process, in the same manner as the first embodiment.

According to the second embodiment, there can be provided the solution testing equipment which can test the ingredient of the solution etc., on the basis of the variation of the radiation pattern of the THz wave in response to the relative permittivity ∈ of the solution as a test object.

Furthermore, according to the solution testing equipment according to the second embodiment, since the ingredient of the solution etc. can be tested on the basis of the variation of the radiation pattern of the THz wave in response to the relative permittivity ∈ of the solution, it becomes possible to perform sensing, e.g. sensing of cells, antigen-antibody reactions, using the solution testing equipment.

According to the solution testing equipment according to the second embodiment, it can obtain information on cells, for example, ranging from approximately 30 μm to approximately 50 μm in width and approximately 2 μm to approximately 3 μm in height by using the (hv) THz wave.

As mentioned above, according to the present invention, there can be provided the solution testing equipment which can detect the output variation of the THz oscillation device using the THz wave (hv) by contacting the liquid or cell on the RTD oscillation device, and can reduce the size and weight thereof.

In the aforementioned embodiments, a device having the same structure is applicable to each of the THz oscillation device and the THz detection device. Moreover, as the THz detection device, a Schottky barrier diode etc. are applicable as another device structure, for example.

Moreover, in the aforementioned embodiments, a terahertz (THz) image sensor which can grasp the radiation pattern of the THz wave in two or three dimensions may be composed by providing a plurality of the THz detection devices therein.

[Other Embodiments]

While the solution testing equipments are described in accordance with the embodiments, it should be understood that the description and drawings that configure part of this disclosure are merely instances, and are not intended to limit the present invention. With the disclosure, artisan might easily think up alternative embodiments, embodiment examples, or application techniques.

Thus, the present invention includes various embodiments etc. which have not been described in this specification.

What is claimed is:

1. A solution testing equipment, comprising:
a terahertz (THz) oscillation device configured to radiate a THz wave;
a THz detection device configured to receive the THz wave;
an insulating film disposed so as to cover the THz oscillation device, the insulating film being in contact with the THz oscillation device;
a solution as a test object disposed on the THz oscillation device, the solution being in contact with the insulating film; and
a glass plate disposed at an upper side of the insulating film, wherein
the solution is disposed on the THz oscillation device by interposing the glass plate therebetween, and
the solution is tested on the basis of output characteristics of the THz wave varying in response to a relative permittivity of the solution.

2. The solution testing equipment according to claim 1, wherein the output characteristics of the THz wave are radiation patterns of the THz wave.

3. The solution testing equipment according to claim 1, wherein the overlay insulating film is composed an $SiO_2$ film ranging from 0.1 μm to 10 μm in thickness.

4. The solution testing equipment according to claim 1, wherein a plurality of recesses for accommodating the solution are formed on a surface of the glass plate.

5. The solution testing equipment according to claim 4, further comprising a moving unit for moving one of the glass plate and the solution testing equipment itself in a horizontal direction so that the recesses are positioned on the upper side of the insulating film.

6. The solution testing equipment according to claim 1, further comprising a reflector configured to reflect the THz wave oscillated from the THz oscillation device, wherein
the THz detection device receives the THz wave through the reflector.

7. The solution testing equipment according to claim 1, wherein the THz oscillation device is provided with a resin layer configured to seal the entire THz oscillation device.

8. The solution testing equipment according to claim 1, wherein radiation patterns of the THz wave corresponding to various solutions is previously obtained to be recorded as reference radiation patterns, and
then a radiation pattern, obtained from the output characteristics of the THz wave of the solution, is matched with the reference radiation patterns, thereby identifying the solution.

9. The solution testing equipment according to claim 1, wherein the THz oscillation device comprises a resonant tunneling diode (RTD).

10. The solution testing equipment according to claim 1, wherein the THz detection device comprises a Schottky barrier diode.

11. The solution testing equipment according to claim 1, wherein the THz detection device comprises a resonant tunneling diode (RTD).

12. The solution testing equipment according to claim 11, wherein the THz detection device detects a variation in an amount of current value in an operational point indicating a negative differential resistance of the RTD, thereby detecting a radiation pattern of the THz wave radiated in response to a relative permittivity of the solution.

13. The solution testing equipment according to claim 1, wherein the solution contains
a predetermined solvent, and
predetermined cells diffused into the predetermined solvent.

14. The solution testing equipment according to claim 1, wherein the THz oscillation device comprises:
- a semiconductor substrate;
- a second electrode disposed on the semiconductor substrate;
- an inter-electrode insulating layer disposed on the second electrode;
- a first electrode disposed via the inter-electrode insulating layer toward the second electrode, the first electrode disposed to be opposite to the second electrode on the semiconductor substrate;
- an MIM reflector formed between the first electrode and the second electrode so that the inter-electrode insulating layer is sandwiched therebetween;
- a resonator disposed between the first electrode and the second electrode opposite to each other on the semiconductor substrate, the resonator adjacent to the MIM reflector;
- an active element disposed at a substantially central part of the resonator;
- a waveguide disposed between the first electrode and the second electrode opposite to each other on the semiconductor substrate, the waveguide adjacent to the resonator; and
- a horn apertural area disposed between the first electrode and the second electrode opposite to each other on the semiconductor substrate, the horn apertural area adjacent to the waveguide.

15. A solution testing equipment comprising:
- a terahertz (THz) oscillation device configured to radiate a THz wave;
- a THz detection device configured to receive the THz wave;
- an insulating film disposed so as to cover the THz oscillation device, the insulating film being in contact with the THz oscillation device; and
- a solution as a test object disposed on the THz oscillation device, the solution being in contact with the insulating film, wherein the solution is tested on the basis of output characteristics of the THz wave varying in response to a relative permittivity of the solution, wherein the THz oscillation device comprises:
- an insulator substrate;
- a first electrode disposed on the insulator substrate;
- an inter-electrode insulating layer disposed on the first electrode;
- an interlayer insulating film disposed on the insulator substrate;
- a second electrode disposed on the interlayer insulating film, the second electrode disposed to be opposite to the first electrode via the inter-electrode insulating layer toward the first electrode;
- a semiconductor layer disposed on the second electrode;
- an MIM reflector formed between the first electrode and the second electrode so that the inter-electrode insulating layer is sandwiched therebetween;
- a resonator disposed between the first electrode and the second electrode opposite to each other on the insulator substrate, the resonator being adjacent to the MIM reflector;
- an active element disposed at a substantially central part of the resonator;
- a waveguide disposed between the first electrode and the second electrode opposite to each other on the insulator substrate, the waveguide adjacent to the resonator; and
- a horn apertural area disposed between the first electrode and the second electrode opposite to each other on the insulator substrate, the horn apertural area adjacent to the waveguide.

16. A solution testing equipment comprising:
- a terahertz (THz) oscillation device configured to radiate a THz wave;
- a THz detection device configured to receive the THz wave;
- an insulating film disposed so as to cover the THz oscillation device, the insulating film being in contact with the THz oscillation device; and
- a solution as a test object disposed on the THz oscillation device, the solution being in contact with the insulating film, wherein the solution is tested on the basis of output characteristics of the THz wave varying in response to a relative permittivity of the solution, further wherein the THz oscillation device comprises:
- an insulator substrate;
- a first electrode disposed on the insulator substrate;
- an inter-electrode insulating layer disposed on the first electrode;
- an interlayer insulating film disposed on the insulator substrate;
- a second electrode disposed on the interlayer insulating film, the second electrode disposed to be opposite to the first electrode via the inter-electrode insulating layer toward the first electrode;
- a semiconductor layer disposed on the second electrode;
- a first slot line electrode disposed on the insulator substrate to be adjacent to the first electrode, the first slot line electrode disposed to be opposite to the first electrode in an opposite side of the second electrode;
- a second slot line electrode disposed on the insulator substrate to be adjacent to the second electrode, the second slot line electrode disposed to be opposite to the second electrode in an opposite side of the first electrode;
- an MIM reflector formed between the first electrode and the second electrode so that the inter-electrode insulating layer is sandwiched therebetween;
- a resonator disposed between the first electrode and the second electrode opposite to each other on the insulator substrate, the resonator adjacent to the MIM reflector;
- an active element disposed at a substantially central part of the resonator;
- a first waveguide disposed between the first electrode and the second electrode opposite to each other on the insulator substrate, the first waveguide adjacent to the resonator;
- a first horn apertural area disposed between the first electrode and the second electrode opposite to each other on the insulator substrate, the first horn apertural area adjacent to the first waveguide;
- a second waveguide disposed between the first electrode and the first slot line electrode opposite to each other on the insulator substrate;
- a second horn apertural area disposed between the first electrode and the first slot line electrode opposite to each other on the insulator substrate, the second horn
apertural area adjacent to the second waveguide;
a third waveguide disposed between the second electrode and the second slot line electrode opposite to each other on the insulator substrate; and
a third horn apertural area disposed between the second electrode and the second slot line electrode opposite to each other on the insulator substrate, the third horn apertural area adjacent to the third waveguide.

17. A solution testing equipment comprising:
a terahertz (THz) oscillation device configured to radiate a THz wave;
a THz detection device configured to receive the THz wave;
an insulating film disposed so as to cover the THz oscillation device, the insulating film being in contact with the THz oscillation device; and
a solution as a test object disposed on the THz oscillation device, the solution being in contact with the insulating film, wherein
the solution is tested on the basis of output characteristics of the THz wave varying in response to a relative permittivity of the solution, wherein
the THz oscillation device comprises:
a semiconductor substrate;
a second electrode disposed on the semiconductor substrate;
an inter-electrode insulating layer disposed on the second electrode;
a first electrode disposed via the inter-electrode insulating layer toward the second electrode, the first electrode disposed to be opposite to the second electrode on the semiconductor substrate;
an MIM reflector formed between the first electrode and the second electrode so that the inter-electrode insulating layer is sandwiched therebetween;
a resonator disposed between the first electrode and the second electrode opposite to each other on the semiconductor substrate, the resonator adjacent to the MIM reflector;
an active element disposed at a substantially central part of the resonator;
a waveguide disposed between the first electrode and the second electrode opposite to each other on the semiconductor substrate, the waveguide adjacent to the resonator; and
a horn apertural area disposed between the first electrode and the second electrode opposite to each other on the semiconductor substrate, the horn apertural area adjacent to the waveguide, wherein
the THz detection device has the same structure as that of the THz oscillation device,
the active element has asymmetrical forward and reverse current voltage characteristics, and
the THz oscillation device operates as an oscillation device at a first operational point indicating negative differential resistance, and the THz detection device operates as a detection device at a second operational point indicating nonlinear characteristics which are not negative resistance regions.

18. The solution testing equipment according to claim 14, wherein the horn apertural area composes an aperture horn antenna.

19. The solution testing equipment according to claim 14, wherein the waveguide is disposed at an apertural area of the resonator.

20. The solution testing equipment according to claim 14, wherein the MIM reflector is disposed at a closed area in an opposite side of an apertural area of the resonator.

21. The solution testing equipment according to claim 14, wherein the second electrode comprises a plurality of stubs in a portion composing the MIM reflector.

22. The solution testing equipment according to claim 14, wherein the first electrode comprises a plurality of stubs in a portion composing the MIM reflector.

23. The solution testing equipment according to claim 14, wherein the insulating film is disposed on the active element, the first electrode, and the second electrode.

24. The solution testing equipment according to claim 1, wherein the THz detection device includes a plurality of THz detection devices, and a THz image sensor is composed by providing the plurality of the THz detection devices therein.

25. A solution testing equipment comprising:
a terahertz (THz) oscillation device configured to radiate a THz wave;
a THz detection device configured to receive the THz wave;
an insulating film disposed so as to cover the THz oscillation device, the insulating film being in contact with the THz oscillation device; and
a solution as a test object disposed on the THz oscillation device, the solution being in contact with the insulating film, wherein
the solution is tested on the basis of output characteristics of the THz wave varying in response to a relative permittivity of the solution, wherein
the THz oscillation device comprises:
a semiconductor substrate;
a first electrode disposed on the semiconductor substrate;
an active element formed on the first electrode; and
a second electrode formed on the active element, wherein
the insulating film is formed across and in contact with the active element, the first electrode, and the second electrode.

26. A solution testing equipment comprising:
a terahertz (THz) oscillation device configured to radiate a THz wave;
a THz detection device configured to receive the THz wave; and
a solution as a test object disposed on the THz oscillation device, wherein
the solution is tested on the basis of output characteristics of the THz wave varying in response to a relative permittivity of the solution, wherein
the THz oscillation device comprises:
an insulator substrate;
a first electrode disposed on the insulator substrate;
an inter-electrode insulating layer disposed on the first electrode;
an interlayer insulating film disposed on the insulator substrate;
a second electrode disposed on the interlayer insulating film, the second electrode disposed to be opposite to the first electrode via the inter-electrode insulating layer toward the first electrode;
a semiconductor layer disposed on the second electrode;
an MIM reflector formed between the first electrode and the second electrode so that the inter-electrode insulating layer is sandwiched therebetween;

a resonator disposed between the first electrode and the second electrode opposite to each other on the insulator substrate, the resonator adjacent to the MIM reflector;

an active element disposed at a substantially central part of the resonator;

a waveguide disposed between the first electrode and the second electrode opposite to each other on the insulator substrate, the waveguide adjacent to the resonator; and a horn apertural area disposed between the first electrode and the second electrode opposite to each other on the insulator substrate, the horn apertural area adjacent to the waveguide.

27. A solution testing equipment comprising:

a terahertz (THz) oscillation device configured to radiate a THz wave;

a THz detection device configured to receive the THz wave; and a solution as a test object disposed on the THz oscillation device, wherein the solution is tested on the basis of output characteristics of the THz wave varying in response to a relative permittivity of the solution, wherein the THz oscillation device comprises:
  an insulator substrate;
  a first electrode disposed on the insulator substrate;
  an inter-electrode insulating layer disposed on the first electrode;
  an interlayer insulating film disposed on the insulator substrate;
  a second electrode disposed on the interlayer insulating film, the second electrode disposed to be opposite to the first electrode via the inter-electrode insulating layer toward the first electrode;
  a semiconductor layer disposed on the second electrode;
  a first slot line electrode disposed on the insulator substrate to be adjacent to the first electrode, the first slot line electrode disposed to be opposite to the first electrode in an opposite side of the second electrode;
  a second slot line electrode disposed on the insulator substrate to be adjacent to the second electrode, the second slot line electrode disposed to be opposite to the second electrode in an opposite side of the first electrode;
  an MIM reflector formed between the first electrode and the second electrode so that the inter-electrode insulating layer is sandwiched therebetween;
  a resonator disposed between the first electrode and the second electrode opposite to each other on the insulator substrate, the resonator adjacent to the MIM reflector;
  an active element disposed at a substantially central part of the resonator;
  a first waveguide disposed between the first electrode and the second electrode opposite to each other on the insulator substrate, the first waveguide adjacent to the resonator;
  a first horn apertural area disposed between the first electrode and the second electrode opposite to each other on the insulator substrate, the first horn apertural area adjacent to the first waveguide;
  a second waveguide disposed between the first electrode and the first slot line electrode opposite to each other on the insulator substrate;
  a second horn apertural area disposed between the first electrode and the first slot line electrode opposite to each other on the insulator substrate, the second horn apertural area adjacent to the second waveguide;
  a third waveguide disposed between the second electrode and the second slot line electrode opposite to each other on the insulator substrate; and
  a third horn apertural area disposed between the second electrode and the second slot line electrode opposite to each other on the insulator substrate, the third horn apertural area adjacent to the third waveguide.

* * * * *